(12) United States Patent
Manasco et al.

(10) Patent No.: US 11,654,057 B2
(45) Date of Patent: May 23, 2023

(54) DEVICES FOR BLEEDING REDUCTION AND METHODS OF MAKING AND USING THE SAME

(71) Applicant: Bio 54, LLC, Chapel Hill, NC (US)

(72) Inventors: Anton Travis Manasco, Chapel Hill, NC (US); Margaret Booth Powell, Chapel Hill, NC (US)

(73) Assignee: Bio 54, LLC, Chapel Hill, NC (US)

( * ) Notice: Subject to any disclaimer, the term of this patent is extended or adjusted under 35 U.S.C. 154(b) by 0 days.

(21) Appl. No.: 17/522,736

(22) Filed: Nov. 9, 2021

(65) Prior Publication Data

US 2022/0062058 A1 Mar. 3, 2022

Related U.S. Application Data

(63) Continuation of application No. PCT/US2021/053641, filed on Oct. 5, 2021, which is a continuation-in-part of application No. PCT/US2021/026714, filed on Apr. 9, 2021.

(60) Provisional application No. 63/090,768, filed on Oct. 13, 2020, provisional application No. 63/087,532, filed on Oct. 5, 2020, provisional application No. 63/007,543, filed on Apr. 9, 2020.

(51) Int. Cl.
*A61F 13/00* (2006.01)
*A61M 35/00* (2006.01)
*A61K 31/197* (2006.01)

(52) U.S. Cl.
CPC .. *A61F 13/00085* (2013.01); *A61F 13/00042* (2013.01); *A61F 13/00063* (2013.01); *A61K 31/197* (2013.01); *A61F 2013/00285* (2013.01)

(58) Field of Classification Search
CPC .................................................. A61M 35/006
USPC ............................................................ 602/53
See application file for complete search history.

(56) References Cited

U.S. PATENT DOCUMENTS

| | | | |
|---|---|---|---|
| 3,639,626 A | | 2/1972 | Nagasawa et al. |
| 3,950,405 A | | 4/1976 | Okano et al. |
| 4,895,559 A | | 1/1990 | Shippert |
| 4,925,327 A | * | 5/1990 | Wirt ....................... B65D 47/42 604/3 |
| 5,209,251 A | | 5/1993 | Curtis et al. |
| 5,288,159 A | | 2/1994 | Wirt |

(Continued)

FOREIGN PATENT DOCUMENTS

| | | | |
|---|---|---|---|
| CA | 2661353 A1 | | 9/2010 |
| JP | 2001017461 A | * | 1/2001 |

(Continued)

OTHER PUBLICATIONS

Recothrom, Thrombin topical (Recombinant) Package Insert, 2008 https://www.fda.gov/media/75321/download (Year: 2008).*

(Continued)

*Primary Examiner* — Kim M Lewis
(74) *Attorney, Agent, or Firm* — Cooley LLP

(57) ABSTRACT

In some embodiments, a system includes an applicator pad, an application device (e.g., a grip), and a reservoir. The grip can be releasably couplable to the applicator pad and configured to dispose the applicator pad against a wound of a subject such that pressure can be transferred to the wound via the applicator pad to enhance hemostasis. The reservoir can be configured to contain medication to be released to the wound via the applicator pad.

28 Claims, 37 Drawing Sheets

(56) References Cited

U.S. PATENT DOCUMENTS

| | | | |
|---|---|---|---|
| 5,308,180 A | 5/1994 | Pournoor et al. |
| 5,405,360 A | 4/1995 | Tovey |
| 5,445,462 A | 8/1995 | Johnson et al. |
| 6,056,970 A | 5/2000 | Greenawalt et al. |
| 6,786,883 B2 | 9/2004 | Shippert |
| 6,991,394 B2 | 1/2006 | Tufts et al. |
| 7,015,194 B2 | 3/2006 | Kjalke |
| 7,108,706 B2 | 9/2006 | Hogle |
| 7,202,065 B2 | 4/2007 | Romisch et al. |
| 7,449,446 B2 | 11/2008 | Elg |
| 7,531,318 B2 | 5/2009 | Srivastava et al. |
| 7,674,250 B2 | 3/2010 | Freyman et al. |
| 7,799,048 B2 | 9/2010 | Hudson et al. |
| 7,845,536 B2 | 12/2010 | Viola et al. |
| 7,887,837 B2 | 2/2011 | Takeoka et al. |
| 7,931,637 B2 | 4/2011 | Vournakis et al. |
| 7,947,739 B2 | 5/2011 | Moore et al. |
| 8,022,106 B2 | 9/2011 | Moore et al. |
| 8,137,375 B2 | 3/2012 | Hudson et al. |
| 8,152,750 B2 | 4/2012 | Vournakis et al. |
| 8,252,302 B2 | 8/2012 | Macdonald |
| 8,257,701 B2 | 9/2012 | Orbe et al. |
| 8,273,795 B2 | 9/2012 | Moore et al. |
| 8,487,005 B2 | 7/2013 | Moore et al. |
| 8,647,650 B2 | 2/2014 | Miyamoto et al. |
| 8,674,074 B2 | 3/2014 | Oestergaard et al. |
| 8,697,747 B2 | 4/2014 | Nielsen et al. |
| 8,758,785 B2 | 6/2014 | Miyamoto et al. |
| 8,784,876 B2 | 7/2014 | Huey et al. |
| 8,791,160 B2 | 7/2014 | Moore et al. |
| 8,802,083 B2 | 8/2014 | Vournakis et al. |
| 8,802,362 B2 | 8/2014 | Grippi et al. |
| 8,809,394 B2 | 8/2014 | Moore et al. |
| 8,835,408 B2 | 9/2014 | Vournakis et al. |
| 8,858,593 B2 * | 10/2014 | Kerber ............... A61B 17/0057 |
| | | 604/59 |
| 8,858,969 B2 | 10/2014 | Pahari et al. |
| 8,956,065 B2 | 2/2015 | Froimson |
| 8,957,113 B2 | 2/2015 | Moore et al. |
| 8,968,777 B2 | 3/2015 | Heasley et al. |
| 8,992,453 B2 | 3/2015 | Vournakis et al. |
| 9,060,939 B2 | 6/2015 | Moore et al. |
| 9,301,936 B2 | 4/2016 | Buderer et al. |
| 9,320,653 B2 | 4/2016 | Vournakis et al. |
| 9,345,651 B2 | 5/2016 | Kuromiya et al. |
| 9,387,178 B2 | 7/2016 | Joshi et al. |
| 9,408,913 B2 | 8/2016 | Wuollett et al. |
| 9,526,738 B2 | 12/2016 | Stasko et al. |
| 9,526,746 B2 | 12/2016 | Kemp et al. |
| 9,533,069 B2 | 1/2017 | Larsen et al. |
| 9,623,223 B2 | 4/2017 | Steinbaugh et al. |
| 9,717,821 B2 | 8/2017 | Schutte et al. |
| 9,839,716 B1 | 12/2017 | Nowakowski |
| 9,889,154 B2 | 2/2018 | Basadonna et al. |
| 9,950,091 B2 | 4/2018 | Mousa et al. |
| 10,118,930 B2 | 11/2018 | Ellermann et al. |
| 10,195,088 B2 | 2/2019 | Phillips et al. |
| 10,239,342 B2 | 3/2019 | Fehlmann et al. |
| 10,292,955 B2 | 5/2019 | Lee et al. |
| 10,376,610 B2 | 8/2019 | Ertan |
| 10,407,488 B2 | 9/2019 | Griffin et al. |
| 10,420,864 B2 | 9/2019 | Pulapura et al. |
| 10,478,851 B2 | 11/2019 | Ettlin |
| 10,596,360 B2 | 3/2020 | Clarke |
| 10,668,071 B2 | 6/2020 | Hassfeld et al. |
| 10,695,300 B2 | 6/2020 | Lee |
| 10,765,782 B2 | 9/2020 | Pulapura et al. |
| 10,800,905 B2 | 10/2020 | Delli-Santi et al. |
| 10,881,803 B2 | 1/2021 | Mcclellan et al. |
| 10,919,073 B2 | 2/2021 | Phipps et al. |
| 10,933,174 B2 | 3/2021 | Pulapura et al. |
| 10,980,676 B2 | 4/2021 | Clayborne et al. |
| 10,980,740 B2 | 4/2021 | Rangabhatla et al. |
| 11,007,218 B2 | 5/2021 | Basadonna et al. |
| 2002/0176849 A1 | 11/2002 | Slepian |
| 2002/0192271 A1 | 12/2002 | Hedner et al. |
| 2003/0008831 A1 | 1/2003 | Yang et al. |
| 2003/0105483 A1 | 6/2003 | Hudson et al. |
| 2005/0054967 A1 | 3/2005 | Ashe et al. |
| 2005/0181978 A1 | 8/2005 | Rojkjaer et al. |
| 2005/0182011 A1 | 8/2005 | Olson et al. |
| 2005/0267014 A1 | 12/2005 | Rojkjaer et al. |
| 2007/0038245 A1 | 2/2007 | Morris et al. |
| 2007/0218114 A1 | 9/2007 | Duggan et al. |
| 2007/0255238 A1 | 11/2007 | Cochrum et al. |
| 2008/0108926 A1 | 5/2008 | Voegele |
| 2008/0138387 A1 | 6/2008 | Machiraju |
| 2008/0193414 A1 | 8/2008 | Proudfoot et al. |
| 2010/0016880 A1 | 1/2010 | Ashenhurst |
| 2011/0060040 A1 | 3/2011 | Virsik et al. |
| 2011/0184060 A1 | 7/2011 | Harris et al. |
| 2012/0070470 A1 | 3/2012 | Pahari et al. |
| 2012/0302640 A1 | 11/2012 | Macalister |
| 2013/0029030 A1 | 1/2013 | Larsen |
| 2013/0330397 A1 | 12/2013 | Neas et al. |
| 2014/0220130 A1 | 8/2014 | Larsen et al. |
| 2015/0038406 A1 | 2/2015 | Buderer et al. |
| 2015/0119851 A1 | 4/2015 | Hoogenakker et al. |
| 2015/0289861 A1 | 10/2015 | Macphee et al. |
| 2015/0320982 A1 | 11/2015 | Massicotte |
| 2015/0366798 A1 | 12/2015 | Lozinsky et al. |
| 2016/0000823 A1 | 1/2016 | Emanuele et al. |
| 2016/0000863 A1 | 1/2016 | Rodríguez et al. |
| 2016/0206580 A1 | 7/2016 | Los et al. |
| 2016/0220799 A1 | 8/2016 | Tarlow et al. |
| 2016/0346239 A1 | 12/2016 | Korobov |
| 2017/0135926 A1 | 5/2017 | Hu et al. |
| 2017/0319755 A1 | 11/2017 | Pulapura et al. |
| 2018/0064780 A1 | 3/2018 | Ingber et al. |
| 2018/0093010 A1 | 4/2018 | Nur et al. |
| 2018/0093043 A1 | 4/2018 | Mcclellan et al. |
| 2018/0116986 A1 | 5/2018 | Joshi et al. |
| 2018/0125721 A1 | 5/2018 | Hoggarth et al. |
| 2018/0140302 A1 | 5/2018 | Pai et al. |
| 2018/0193874 A1 * | 7/2018 | Pozanc ............... B05C 11/1026 |
| 2018/0207413 A1 | 7/2018 | Skakoon et al. |
| 2018/0236123 A1 | 8/2018 | Manoryk et al. |
| 2018/0243505 A1 | 8/2018 | Genosar |
| 2018/0264243 A1 | 9/2018 | Cordoba et al. |
| 2018/0271898 A1 | 9/2018 | Basadonna et al. |
| 2019/0184052 A1 * | 6/2019 | Ilan ................ A61L 15/425 |
| 2019/0192564 A1 | 6/2019 | Hijazi et al. |
| 2019/0224121 A1 | 7/2019 | Erstad et al. |
| 2020/0046663 A1 | 2/2020 | Murdock |
| 2020/0121871 A1 | 4/2020 | Genosar |
| 2020/0253874 A1 | 8/2020 | Vadelund et al. |
| 2020/0289415 A1 | 9/2020 | Kelm et al. |
| 2020/0360055 A1 | 11/2020 | Hong et al. |
| 2021/0001023 A1 | 1/2021 | Hijazi et al. |
| 2021/0008243 A1 | 1/2021 | Ericson |
| 2021/0038757 A1 | 2/2021 | Ilan et al. |
| 2021/0046121 A1 | 2/2021 | Moskowitz et al. |
| 2021/0228478 A1 | 7/2021 | Rangabhatla |
| 2021/0386984 A1 | 12/2021 | Skakoon et al. |
| 2022/0249292 A1 | 8/2022 | Manasco et al. |

FOREIGN PATENT DOCUMENTS

| | | |
|---|---|---|
| JP | 5128837 B2 | 1/2013 |
| WO | WO 00/09018 A1 | 2/2000 |
| WO | WO 2014/209389 A1 | 12/2014 |
| WO | WO 2015/107139 A1 | 7/2015 |
| WO | WO 2016/178053 A1 | 11/2016 |
| WO | WO 2017/007917 A1 | 1/2017 |
| WO | WO 2018/197946 A1 | 11/2018 |
| WO | WO 2018/232277 A1 | 12/2018 |
| WO | WO 2019/219130 A1 | 11/2019 |
| WO | WO 2020/046769 A1 | 3/2020 |
| WO | WO 2020/176507 A1 | 9/2020 |

(56) References Cited

FOREIGN PATENT DOCUMENTS

| WO | WO 2020/248010 A1 | 12/2020 |
|---|---|---|
| WO | WO 2021/07698 A1 | 10/2021 |

OTHER PUBLICATIONS

Amini, et al., "Topical Tranexamic Acid versus Phenylephrine-lidocaine for the Treatment of Anterior Epistaxis in Patients Taking Aspirin or Clopidogrel; a Randomized Clinical Trial," Archives in Academic Emergency Medicine, 2021, 9(1), e6, 1-7.

Ausen, et al., "Serum Concentrations and Pharmacokinetics of Tranexamic Acid after Two Means of Topical Administration in Massive Weight Loss Skin-Reducing Surgery," Cosmetic, Jun. 2019, 143(6), 1169e-1178e.

Baylis, et al., "Self-propelled dressings containing thrombin and tranexamic acid improve short-term survival in a swine model of lethal junctional hemorrhage," Shock, Sep. 2016, 46(3), 123-128.

Boccio, et al., "Topical Tranexamic Acid for Hemostasis of an Oral Bleed in a Patient on a Direct Oral Anticoagulant," Clinical Practice and Cases in Emergency Medicine, May 2020, IV(2), 146-149.

Borea, et al., "Tranexamic acid as a mouthwash in anticoagulant-treated patients undergoing oral surgery, an alternative method to discontinuing anticoagulant therapy," Oral Surg. Oral Med. Oral Pathol., Jan. 1993, 75, 29-31.

Burns, "Case Report: Topical Tranexamic Acid as Novel Treatment of Refractory Bleeding After Excisional Cervical Procedure [27G]," Saturday Posters, Obstetrics & Gynecology, 2018, 82S.

Carter, et al., "Tranexamic Acid Mouthwash Versus Autologous Fibrin Glue in Patients Taking Warfarin Undergoing Dental Extractions: A Randomized Prospective Clinical Study," J. Oral Maxillofac Surg, 2003, 61, 1432-1435.

Carter, et al., "Current concepts of the management of dental extractions for patients taking warfarin," Australian Dental Journal, 2003, 48(2), 89-96.

Carter, et al., "Tranexamic acid mouthwash—A prospective randomized study of a 2-day regimen vs 5-day regimen to prevent postoperative bleeding in anticoagulated patients requiring dental extractions," Int. J. Oral Maxillofac. Surg., 2003, 32, 504-507.

ClinicalTrials.gov Identifier: NCT02918201, The Effect of Topical Tranexamic Acid on Postoperative Bleeding from Superficial Wounds, last update posted Feb. 1, 2021, 1-8.

Coetzee, "The use of topical crushed tranexamic acid tablets to control bleeding after dental surgery and from skin ulcers in haemophilia," Haemophilia, 2007,13, 443-444.

Condoret, et al., "Industrialized of a supercritical $CO_2$ process for oxidation of cellulose," Université de Toulouse, Laboratoire de Génie Chimique, INP, CNRS, UPS, Tououse, France, CS21, 2015, 1-4.

Cyklokapron ® (tranexamic acid) injection, for intravenous use, Initial U.S. Approval: 1986, revised Mar. 2021, 1-10.

Eikebrokk, et al., "Cytotoxicity and effect on wound re-epithelialization after topical administration of tranexamic acid," BJS Open, 2019, 3, 840-851.

Glineur, et al., "A randomized, controlled trial of Veriset™ hemostatic patch cardiovascular bleeding," Medical Devices: Evidence and Research, 2018, 11, 65-75.

Hydrasorb ® Hydrophilic Urethane Foam Product Data Sheet, Carwild Corp, Jun. 2014, 1 page.

Hydrophilic SAQ, Product Data Sheet, Woodbridge INOAC Technical Products, revised Aug. 2017, 1 page.

International Search Report and Written Opinion issued in PCT/US2021/053641 dated Oct. 29, 2021, 1-23.

International Search Report and Written Opinion issued in PCT/US2021/026714, dated Jul. 28, 2021, 1-9.

Joseph, et al., "Tranexamic acid for patients with nasal haemorrhage (epistax)," Cochrane Database of Systematic Reviews, 2018, 12(CD004328), 1-4.

Joseph, et al., "Does Oral or Topical Tranexamic Acid Control Bleeding from Epistaxis?" Emergency Medicine, Aug. 2019, 74(2), 300-302.

Ker, et al., "Topical application of tranexamic acid for the reduction of bleeding (Review)," Cochrane Database of Systematic Reviews, 2013, 7(CD010562), 1-65.

Liu, et al., "Topical Metered-dosing Dispenser Performance Evaluation," International Journal of Pharmaceutical Compounding, 2016, 20(3), 239-246.

Lysteda™ (tranexamic acid) Tablets, Initial U.S. Approval: 1986, revised: Oct. 2013, Reference ID: 3383847, 1-8.

Montroy, et al., "The efficacy and safety of topical tranexamic acid: A systematic review and meta-analysis," Transfusion Medicine Reviews, 2018, 1-14.

Morgenstern, "NoPAC: No benefit from TXA in epistaxis, TXA for Epistaxis," First10EM, Feb. 2021, 1-9.

Nikoyan, et al., "Epistaxis and hemostatic devices," Oral Maxillofacial Surg. Clin. N. Am., 2012, 24, 219-228.

NHS, "Use of Topical Tranexamic Acid to control surface bleeding from the fungating wounds in the skin," East Lancashire Health Economy Medicines Management Board, review date Nov. 30, 2020, 1 page.

Noble, et al., "Case report: use of topical tranexamic acid to stop localised bleeding," Emerg. Med. J., 2013, 30, 509-510.

Nuvvula, et al., "Efficacy of tranexamic acid mouthwash as an alternative for factor replacement in gingival bleeding during dental scaling in cases of hemophilia: A randomized clinical trial," Contemp Clin. Dent., Jan.-Mar. 2014, 5(1), 49-53.

Patatanian, et al., "Hemostatic Mouthwashes in Anticoagulated Patients Undergoing Dental Extraction," Ann. Pharmacother, 2006, 40, 2205-2210.

Product ID: 4-010-XX, Technical Data Sheet, Superior Felt & Filtration, 2018, 1 page.

PVA Expandacell ® foam for epistaxis management after trauma or surgery, Rhino Rocket ® Nasal Packing, Summit Medical, Shippert Medical, https://summitmedicalusa.com/rhinology/rhinorocket-nasal-packing/, retrieved on Jun. 16, 2021, 1 page.

Question: Can tranexamic acid be applied topically to a bleeding wound? Palliative Meds Info, Dec. 2018, 1-2.

Rapid Rhino Epistaxis Products: Inflatable tamponade designed to create a fast, single treatment solution with a low-profile and self-lubricating properties, Smith & Nephew, Inc., 2015, 1-4.

Reuben, et al., "The Use of Tranexamic Acid to Reduce the Need for Nasal Packing in Epistaxis (NoPAC): Randomized Controlled Trial," Annals of Emergency Medicine, 2021, 1-10.

Reversal strategies DOAC bleeding—UptoDate, "Direct oral anticoagulant-associated bleeding reversal strategies," UptoDate, Inc., 2021, https://www.uptodate.com/contents/image?imageKey=HEME/96230, 1-2.

Siegal, et al., "How I treat target-specific oral anticoagulant-associated bleeding," Blood, Feb. 20, 2014, 123(8), 1152-1156 (7 pages total).

Siegel, et al., "Vorinostat in combination with lenalidomide and dexamethasone in patients with relapsed or refractory multiple myeloma," Blood Cancer Journal, 2014, 4, e182, 1-6.

SM32H, Product Data Sheet, Woodbridge INOAC Technical Products, revised Aug. 2017, 1 page.

Swaminathan, "Topical TXA in Epistaxis," Rebel Em, Dec. 7, 2017, https://rebelem.com/topical-txa-in-epistaxis/, 1-13.

$^{Pr}$Tranexamic Acid Injection, USP. Product Monograph, 100 mg / ml Tranexamic acid injection USP, Sterile Solution Antifibrinolytic agent, Baxter Corporation, Sep. 17, 2020, Control No. 229119, 1-21.

Tranexamic Acid in Sodium Chloride injection, for intravenous use. Initial U.S. Approval: 1986, Revised Apr. 2019, Reference ID: 4419268, 1-8.

UNO Medical Center Guideline, "Tranexamic Acid in Adult Emergency Department Patients," 2019, 1-4.

Utkewicz, et al., "Epistaxis Complicated by Rivaroxaban Managed with Topical Tranexamic Acid: Case Report and Literature Review," American Journal of Emergency Medicine, 2015, 1-11.

(56) References Cited

OTHER PUBLICATIONS

Whitworth, et al., "Comparative effectiveness of topically administered tranexamic acid versus topical oxymetazoline spray for achieving hemostasis in epistaxis," The Journal of Emergency Medicine, 2019, 1-6.

Whitworth, et al., "Data on the hemostasis in epistaxis with Topically Administered TXA Versus Topical Oxymetazoline Spray," Data in brief, 2020, 29(105283), 1-4.

Wound Home Skills Kit: Lacerations & Abrasions, Surgical Patient Education Program, American College of Surgeons Division of Education, Oct. 23, 2017, 1-41.

Zahed, et al., "A new and rapid method for epistaxis treatment using injectable form of tranexamic acid topically: a randomized controlled trial," American Journal of Emergency Medicine, 2013, 31, 1389-1392.

Zahed, et al., CME Information: Topical Tranexamic Acid Compared with Anterior Nasal Packing for Treatment of Epistaxis in Patients taking Antiplatelet Drugs: Randomized Controlled Trial, Society for Academic Emergency Medicine, 2017, 261-266.

Zirk, et al., "Supportive topical tranexamic acid application for hemostasis in oral bleeding events—retrospective cohort study of 542 patients," Journal of Cranio-Maxillo-Facial Surgery, 2018, doi: 10.1016/j.jcms.2018.03.009, 1-25.

Non-Final Office Action for U.S. Appl. No. 17/728,894 dated Jul. 14, 2022, 23 pages.

Final Rejection Office Action for U.S. Appl. No. 17/728,894 dated Nov. 7, 2022, 16 pages.

Mylan, EpiPen 2-Pak (epinephine injection, USP) Auto-Injectors 0.3 mg (package), Nov. 2018, 2 pages.

\* cited by examiner

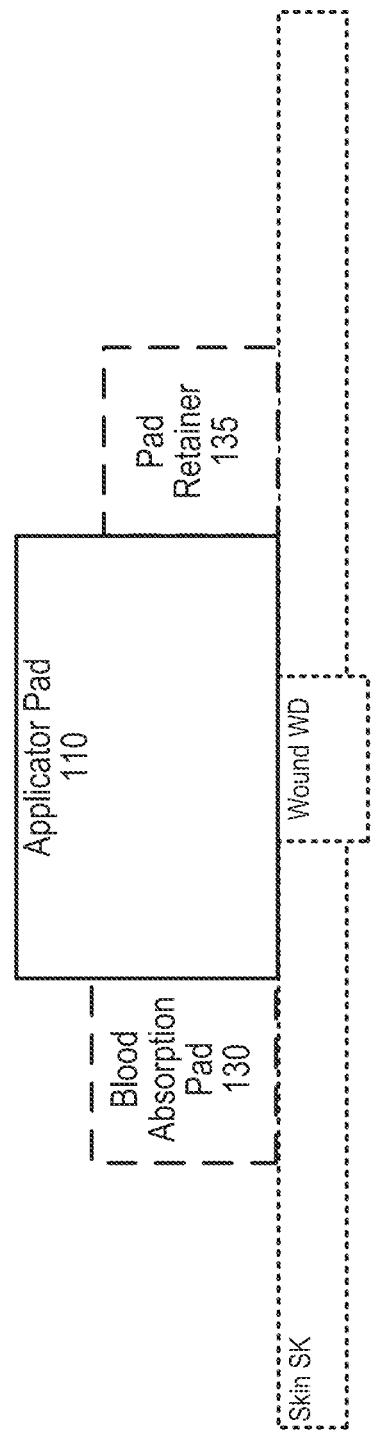

1300

1300

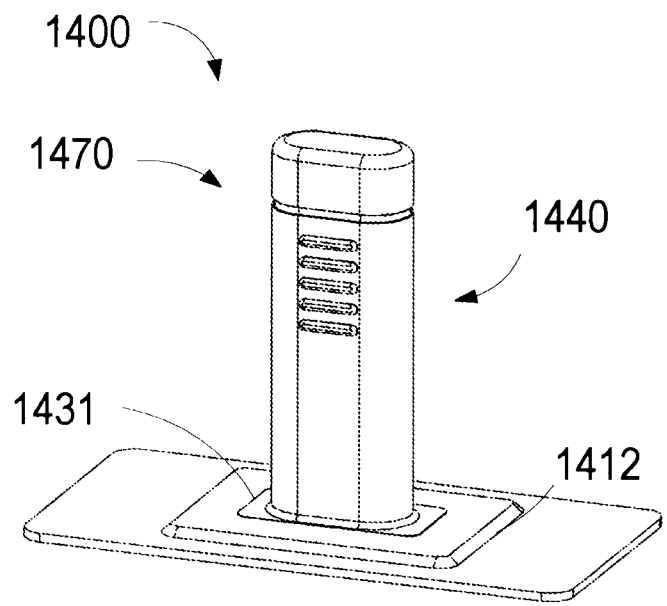
FIG. 16A
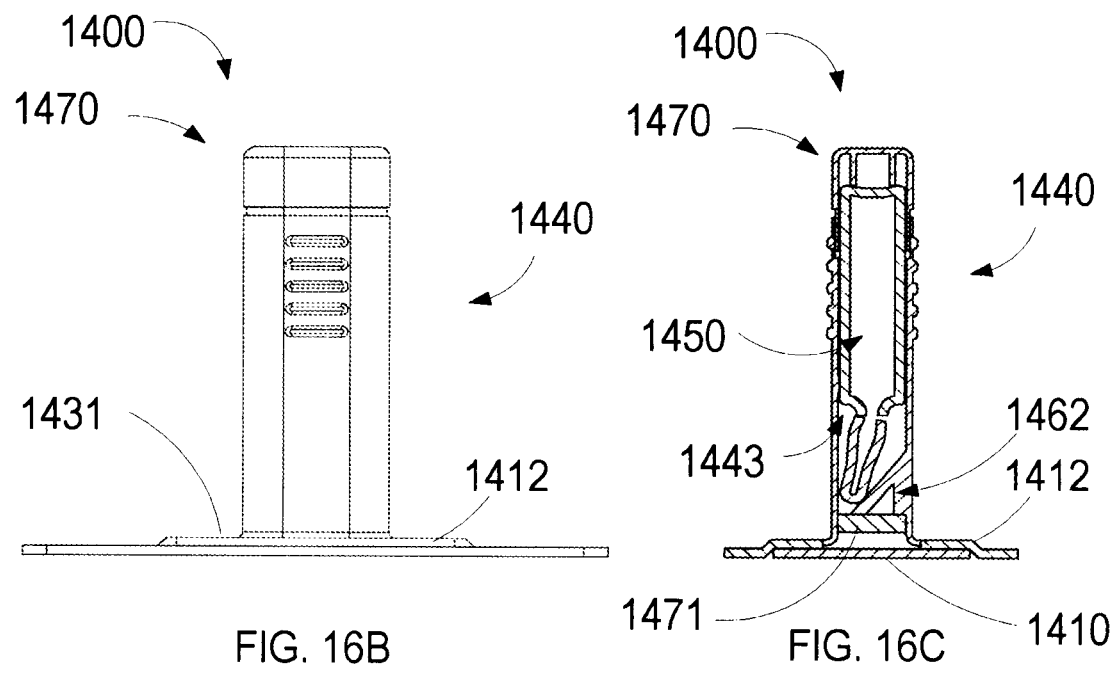
FIG. 16B
FIG. 16C

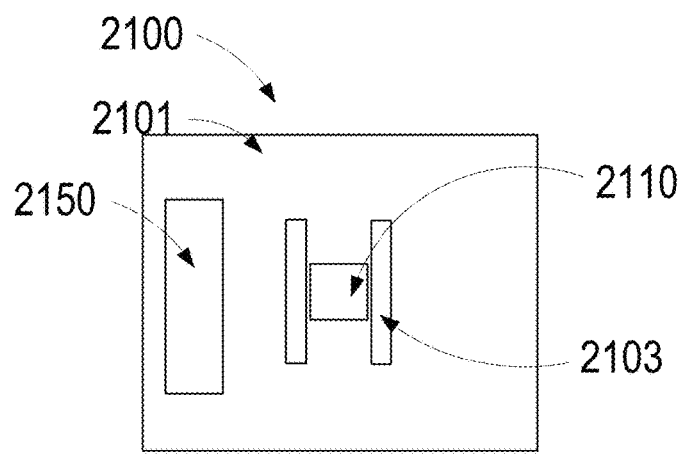
FIG. 25A
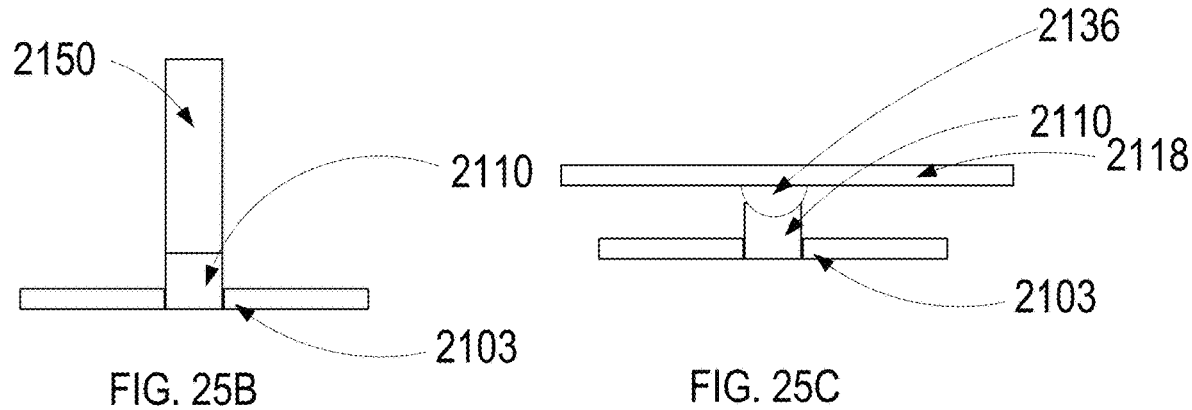
FIG. 25B
FIG. 25C

DEVICES FOR BLEEDING REDUCTION AND METHODS OF MAKING AND USING THE SAME

CROSS-REFERENCE TO RELATED APPLICATIONS

This application is a continuation of International PCT Application No. PCT/US2021/053641, entitled "Devices for Bleeding Reduction and Methods of Making and Using the Same," filed on Oct. 5, 2021, which is a continuation-in-part of International PCT Application No. PCT/US2021/026714, entitled "Devices for Bleeding Reduction and Methods of Making and Using the Same," filed on Apr. 9, 2021, which claims priority to U.S. Provisional Patent Application Ser. No. 63/007,543, entitled "Devices for Bleeding Reduction and Methods of Making and Using the Same," filed on Apr. 9, 2020, the disclosure of each of which is incorporated by reference herein in its entirety.

International PCT Application No. PCT/US2021/053641 also claims priority to U.S. Provisional Patent Application Ser. No. 63/087,532, entitled "Methods for Self-Treatment or Home Care Provider Treatment of Minor Wounds," filed on Oct. 5, 2020 and U.S. Provisional Patent Application Ser. No. 63/090,768, entitled "Methods for Self-Treatment or Care Provider Treatment of Minor Wounds," filed on Oct. 13, 2020, the disclosure of each of which is incorporated by reference herein in its entirety.

BACKGROUND

Patients with minor injuries seek medical attention at primary care clinics, urgent care centers, and hospital emergency rooms. Many urgent care centers are not open twenty-four hours per day and seven days per week (24/7). Rural areas may have limited availability of these urgent care centers. A common type of visit to a hospital emergency room or urgent care center is a wound requiring cessation of bleeding, especially patients on anticoagulant or antiplatelet medications. As the population ages, more patients require these medications for a variety of conditions.

Better methods and devices are needed to allow patients, family members, and/or caretakers to safely treat at home, or at the place of the injury, minor wounds requiring the cessation of bleeding.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Disclosed herein are devices, methods of using devices, and methods of making devices for treatment of bleeding, e.g. from minor wounds. In some embodiments, a system includes an applicator pad, an application device (e.g., a grip), and a reservoir. The grip can be releasably couplable to the applicator pad and configured to dispose the applicator pad against a wound of a subject such that pressure can be transferred to the wound via the applicator pad to enhance hemostasis. The reservoir can be configured to contain medication to be released to the wound via the applicator pad.

Additional features, aspects and/or advantages will be recognized and appreciated upon further review of a detailed description of the illustrative embodiments taken in conjunction with the accompanying drawings.

BRIEF DESCRIPTION OF THE DRAWINGS

FIG. 3C is a schematic illustration of the bleeding treatment device of FIG. 3A with the grip removed.

FIGS. 16A-16C are schematic illustrations of a bleeding treatment system in a wetting configuration, according to an embodiment.

FIGS. 25A-25C are schematic illustrations of a sequence of steps performed using a kit, according to an embodiment.

DETAILED DESCRIPTION

The detailed description herein serves to describe non-limiting embodiments or examples involving various inventive concepts and uses reference numbers for ease of understanding these examples. Common reference numbers between the figures refer to common features and structure having the same or similar functions, as will be understood. While various figures will have common reference numbers referring to such common features and structure, for purposes of conciseness, later figure descriptions will not necessarily repeat a discussion of these features and structure.

Figure 1:
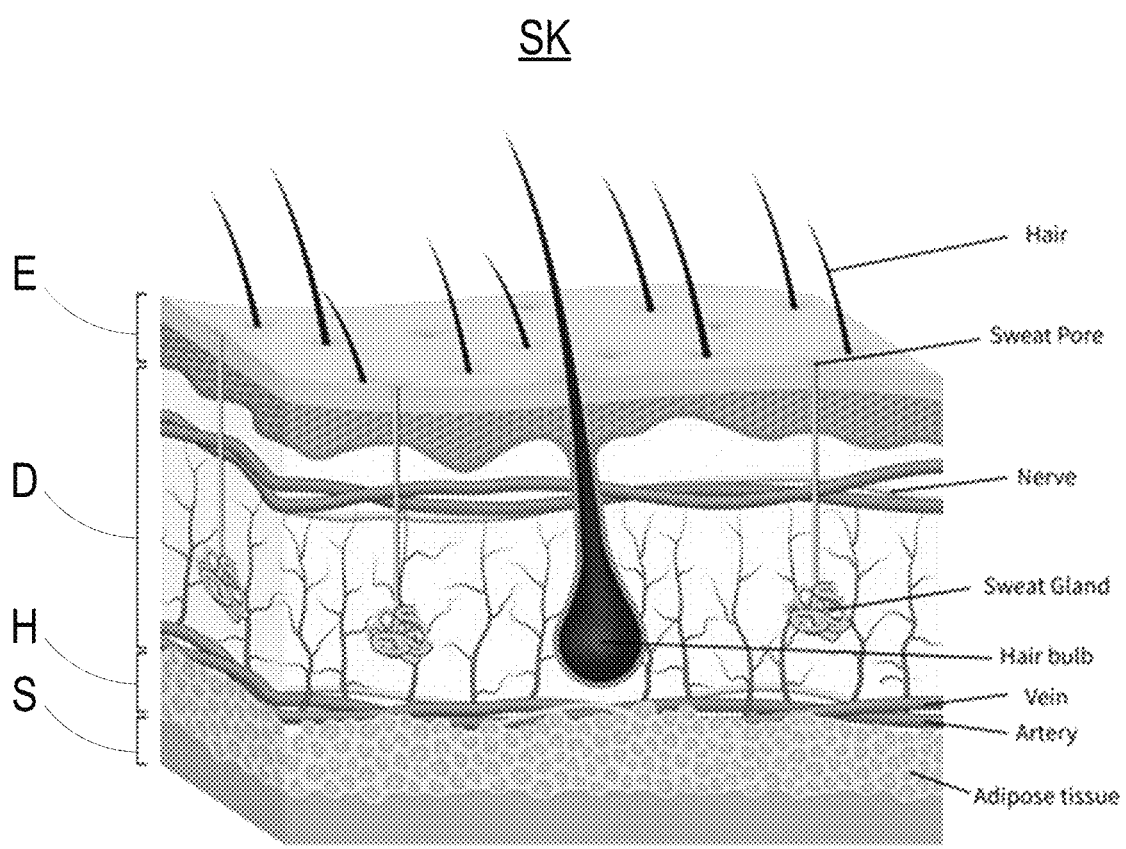
FIG. 1 is a cross-sectional view of a skin portion, showing the structures of the epidermis, derma, hypodermis, and subcutaneous layer.

For reference, FIG. 1 illustrates a cross-sectional view of a skin portion SK of a human, e.g., of a subject to be treated. The skin portion SK includes an epidermis E, a derma D, a hypodermis H, and a subcutaneous layer S.

The systems and methods described herein can be configured to treat a wound and/or assist with cessation of bleeding of a wound that extends through the epidermal and/or dermal layer, is non-arterial, is not resulting in pulsatile bleeding, and has no subcutaneous fat or muscle exposed. In some embodiments, the systems and methods described herein can be self-administered (e.g., the administrator of the system and/or method is also the subject having the wound). In some embodiments, the systems and methods described herein can be administered to a subject having a wound by a person other than the subject, such as a caregiver (e.g., a non-medical home care provider such as a family member) or clinician. In some embodiments, the systems and methods described herein can be administered to a non-human patient such as a pet dog or a pet cat, and the method steps can be performed by a pet owner or veterinarian. In some embodiments, target wounds treatable by the systems and methods described herein may be less than 3 centimeters in length. In some embodiments, target wounds treatable by the systems and methods described herein in a home use setting may be wounds not requiring stitches or sutures to close. In some embodiments, target wounds treatable by the systems and methods described herein in a clinical setting may be wounds for which bleeding can first be attempted to be stopped using the systems and methods described herein before utilizing stitches or sutures if the systems and/or methods described herein are not effective after one use.

Potential patient populations that can be treated by the systems and methods described herein include any person with topical bleeds (i.e., bleeding from the skin). For example, target patient populations can include people with naturally-induced, drug-induced, or procedurally-induced increased susceptibility to bleeding and/or resistance to blood clotting. Naturally-induced susceptibility to bleeding and/or resistance to blood clotting can arise from a chronic condition such as hemophilia, Von Willebrand disease, vascular disorders (e.g., Osler-Weber-Rendu), coagulopathies, kidney failure, liver failure, bone marrow suppression (pathologically or medication-induced) platelet disorders, age (older people can have more friable skin), or conditions (e.g., a genetic condition) that render the person more accident prone or difficult to treat (including age and/or motor or cognitive deficits). Drugs that can induce susceptibility to bleeding and/or resistance to clotting can include: anticoagulation medications such as warfarin, heparin, factor Xa inhibitor, thrombin inhibitors, low-molecular weight heparin, dabigatran, argatorban, hirudin, rivaroxaban, apixaban, edoxaban, fondaparinux, enoxaparin, dalteparin, and bivalirudin; and antiplatelet medications such as platelet aggregation inhibitors such as aspirin (acetylsalicylic acid or ASA), cangrelor, ticagrelor, lopidogrel, prasugrel, cilostazol, clopidogrel, dipyridamole, ticlopidine, glycoprotein platelet inhibitors such as epifibatide, tirofiban, abciximab, and protease-activated receptor-1 antagonists such as vorapaxar. Anticoagulation medications can be taken for a wide variety of indications, such as deep venous thrombosis, pulmonary embolus, and atrial fibrillation. Medical procedures that can induce susceptibility to bleeding and/or resistance to clotting can include renal replacement therapy (e.g., hemodialysis), cardiopulmonary bypass, extra-corporeal membrane oxygenation (ECMO), chemical thrombolysis (with tissue plasminogen activating factor (TPA)), cardiac catheterization, peripheral vascular procedures (e.g., femoral-popliteal bypass, arterial thrombectomy), mechanical thrombectomy, angiography, and other neuro-interventional procedures and interventions.

Figure 2:
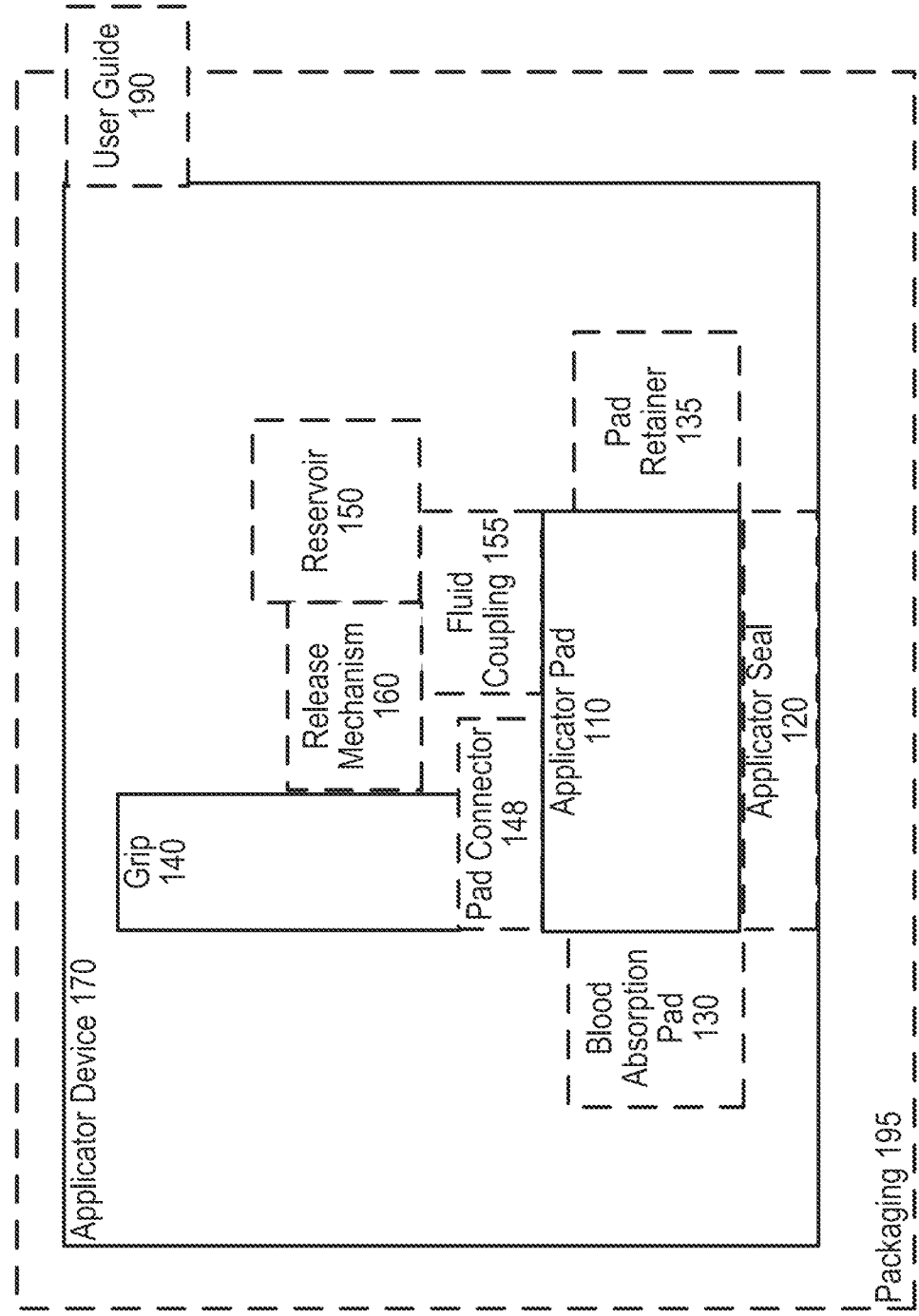
FIG. 2 is a schematic illustration of a bleeding treatment system, according to an embodiment.

A bleeding treatment system 100 that can be used to treat a wound requiring cessation of bleeding is illustrated schematically in FIG. 2. As shown in FIG. 2, the bleeding treatment system 100 includes an applicator pad 110, an optional applicator seal 120 coupled to the applicator pad 110, an optional blood absorption pad 130 coupled to the applicator pad 110, one or more optional reservoirs 150 fluidically coupled to the applicator pad 110 via a fluid coupling 155 and containing one or more medications, an applicator device 170 releasably couplable to the applicator pad 110 and including a grip 140, an optional release mechanism 160 coupled to the reservoir 150, the fluid coupling 155, and the grip 140, an optional pad retainer 135 coupled to the applicator pad 110, an optional user guide 190 associated with the applicator device 170, and optional packaging 195 to contain the other components of the bleeding treatment system 100. The grip 140 can be releasably couplable to the applicator pad 110 via an optional pad connector 148.

The applicator pad 110 (also referred to as a topical applicator pad) is sized, configured, and formed of material, suitable for covering a wound treatable by the system 100. The applicator pad 110 may be formed of any one or more materials having suitable physical properties. For example, the material is preferably capable of absorbing blood. The material may also swell or expand upon absorbing fluid such as blood. The material may also be capable of containing, absorbing, wicking, or otherwise transporting one or more medications for application to a surface of the wound WD and/or the skin SK surrounding the wound. It should be biologically compatible with the skin SK and wound WD. Preferably the one or more materials are also non-reactive, or otherwise compatible with any medication(s) to be transported by the applicator pad 110, e.g., not alter the composition, delivery, or efficacy of the medication(s) or degrade or otherwise lose any of its desired physical properties upon exposure to the medication(s) over the maximum duration of the wound treatment. The material is preferably sufficiently stiff, resilient, etc. to be capable of applying a sufficient amount of pressure against the wound treatment to aid in achieving hemostasis, i.e., function as a hemostat. At least a bottom or distal surface of the applicator pad 110 (e.g., any surface exposed prior to use of the bleeding treatment system 100) can be covered or enclosed by the removable applicator seal 120 to prevent contamination of the applicator pad 110 and/or prevent undesired release of any medication(s) that may be contained in the applicator pad 110. The applicator pad 110 can be formed of a sponge material. The applicator seal 120 can be formed as a film or other thin layer of material non-reactive with the applicator pad 110. The applicator seal 120 can be removed from the applicator pad 110 prior to use (e.g., via peeling).

Suitable materials for the applicator pad 110 include polymers or other compositions, such as polyvinyl alcohol (PVA), polyurethane (hydrophilic or otherwise), polypropylene, which may be formed into foams (open or closed cell) (e.g., a porous expandable foam), natural fibers such as cotton, linen, wool, etc. in woven or non-woven (e.g. felt) form, and/or layered matrices of foam and/or gauze packing. The applicator pad 110 may be formed monolithically of a single material, or may be formed as a composite or other aggregation of different materials. For example, the applicator pad 110 may be primarily formed of one material, and have a relatively thin covering of a second material. The materials may achieve the desired functions in different ways. For example, absorption of blood may be achieved mechanically, e.g. by capillary wicking, and/or chemically, such as by absorption into, for example, molecular sieves or other desiccants, or combination with materials such as clays, e.g. kaolin, bentonite, montmorillonite, saponite, polygorskite, attapulgite, and/or sepiolite. In some embodiments, clay may be dispersed in a liquid medium. In some embodiments, the applicator pad 110 can include a hemostatic patch and a flexible insulating or wicking mechanism (also referred to as a backing portion or layer). In some embodiments, the hemostatic patch can include liquid medication, and the flexible insulating or wicking mechanism can isolate a hand applying pressure to the applicator pad 110 from the wound site and the liquid medication.

As explained in more detail below, the applicator pad 110 may include, incorporate, or embody a reservoir for medication(s), and a different material may be used to form or bound such a reservoir. In some embodiments, the applicator pad 110 can include a reservoir for dry or lipophilized medication that may be made flowable via fluid released from a reservoir of the applicator device 170 and/or blood from the wound. In some embodiments, the applicator pad 110 can define or include internal structures or passages to aid flow of medication through the applicator pad 110 and/or preferentially direct flow toward target wound tissue. In some embodiments, the applicator pad 110 can include a colored dye.

The bleeding treatment system 100 is preferably configured to deliver one or more medications to target wound tissue during treatment, e.g. via the applicator pad 110. The medication(s) may be contained in one or more reservoirs 150 (which, as noted above, may be separate from or incorporated into the applicator pad 110), may be selectively released from the reservoir(s) 150 by one or more release mechanisms 160, and may be conveyed from the reservoir(s) 150 to the applicator pad 110 by one or more fluid couplings 155. For example, the reservoir 150 may be implemented as a container (ampoule or the like) having a volume sufficient to contain a therapeutically effective amount of the medication and formed of material impermeable to, and non-reactive with, the medication or its constituents, such as glass, metal, plastic, polymer (e.g., a rigid polymer such as polyethylene, polypropylene, polyamide, polycarbonate), etc. In some embodiments, the reservoir 150 may be formed of a material that can be broken or punctured to release the contents of the reservoir 150 (e.g., plastic or glass). The reservoir 150 may have an opening through which the medication can be introduced into the reservoir 150 and/or selective selectively released therefrom. In some embodiments, the reservoir 150 can include a vent.

The grip portion 140 can be formed of any suitable material, with at least the distal end (e.g., the optional plate) being formed of a relatively rigid material capable of applying suitable pressure to the applicator pad 110. For example, the grip portion 140 (or at least a body of a first portion of the grip 140) can be formed of a rigid polymer such as polyethylene, polypropylene, polyamide, and/or polycarbonate.

The reservoir 150 may be contained, in whole or in part, within the applicator pad 110, or may be coupled thereto via a fluid coupling 155, such as a tube, wick, etc. The medication(s) may be selectively released from the reservoir 150 so that the medication(s) can be received in the applicator pad 110, e.g. by the release mechanism 160. The release mechanism 160 may be, for example a valve, which may be opened to establish fluidic communication between the reservoir 150 and the applicator pad 110, directly or via fluid coupling 155, and may also be selectively closed to fluidically isolate the medication(s) in the reservoir 150. The release mechanism may be a removable or frangible cap or other closure closing an opening in reservoir 150. The reservoir 150 may itself be frangible, e.g., formed of glass that may be readily broken or at least partially of a material that bursts when the contents of the reservoir 150 are above a threshold pressure, and the medication(s) can be released from the reservoir 150 by causing or allowing the reservoir 150 to be broken. As noted above, in some embodiments the reservoir 150 may be a part of the applicator pad 110. For example, the material of the applicator pad 100 may be soaked or saturated with medication(s), and enclosed with the applicator seal 120 (e.g., a film or other thin layer of material impermeable to and non-reactive with the medication(s)). The medication(s) can be released from the reservoir 150 by removing the applicator seal 120, exposing the surface of the applicator pad 110 so that the medication(s) can be delivered to the wound tissue with which the surface of the applicator pad 110 is placed in contact.

In some embodiments, volume and material of the applicator pad 110 can be selected such that the amount of medication(s) contained in one or more reservoirs 150, whether separate from the applicator pad 110 or incorporated into the applicator pad 110, or the amount of medication(s) can be pre-soaked into the applicator pad 110 such that the applicator pad 110 is about 35% saturated (i.e., contains about 35% of the amount of the medication(s) that it is capable of containing). In some embodiments, the applicator pad 110 can be configured to be between about 67 and about 100% saturated by the amount of medication(s). In some embodiments, the applicator pad 110 is configured to be between about 25 and about 50% saturated by the amount of medication(s). In some embodiments, the applicator pad 110 can be pre-soaked or filled to hold a metered dose of medication. In some embodiments, the applicator pad 110 can be configured such that the volume of medication(s) is effective to treat the wound but such that the medication does not travel across the user's skin outside of the treatment area (e.g., down a user's arm or leg) (e.g., configured to be about 35% saturated or between about 25% and about 50% saturated).

The applicator pad 110 can be any suitable shape and/or size that is, preferably, sufficient to cover the target wound. For example, the perimeter of the applicator pad 110 can be formed as a circle, an oval, an ellipse, a square, a rounded square, a rectangle, a rounded rectangle, a triangle, a pentagon, a hexagon, or any other suitable shape. As described above, target wound sizes to be covered by the applicator pad 110 may be, for example, less than about 3 centimeters in length and/or width. In some embodiments, for example, the applicator pad 110 can have a square perimeter having side lengths of about 1.5 inches. In some embodiments, the applicator pad 110 can have a smaller area. In some embodiments, the applicator pad 110 can have a surface area between about 3.0 $cm^2$ and about 7.0 $cm^2$. In some embodiments, the applicator pad 110 can have a surface area between about 7.0 $cm^2$ and about 12.0 $cm^2$. In some embodiments, the applicator pad 110 can have a surface area of between about 2 $cm^2$ and about 25 $cm^2$. In some embodiments, the applicator pad 110 can have a surface area between about 3 $cm^2$ and about 10 $cm^2$ or between about 10 $cm^2$ and about 20 $cm^2$. For example, the surface area may be about 2 $cm^2$, about 3 $cm^2$, about 4 $cm^2$, about 5 $cm^2$, about 6 $cm^2$, about 7 $cm^2$, about 8 $cm^2$, about 9 $cm^2$, about 10 $cm^2$, about 11 $cm^2$, about 12 $cm^2$, about 13 $cm^2$, about 14 $cm^2$, about 15 $cm^2$, about 16 $cm^2$, about 17 $cm^2$, about 18 $cm^2$, about 19 $cm^2$, about 20 $cm^2$, about 21 $cm^2$, about 22 $cm^2$, about 23 $cm^2$, about 24 $cm^2$, or about 25 $cm^2$.

The applicator device 170 may be any suitable device manipulable by a user to dispose the applicator pad 110 into a desired location, e.g., adjacent a wound WD, and to deposit the applicator pad 110 in the desired location. For example, the applicator device 170 may be a mechanical syringe that includes a barrel having a distal end suitable for attachment to the applicator pad 110 and a proximal end that may be grasped by the user. In some embodiments, the reservoir 150, the release mechanism 160, and/or the fluid coupling 155 can be disposed within the barrel (e.g., between a plunger and the applicator pad 110). In some embodiments, the applicator device 170 can include a plunger movable relative to the barrel and to which a user can apply distally directed force to engage the distal end of the plunger with the reservoir 150 and to cause the contents of the reservoir 150 to be urged distally through the barrel, out of the distal end of the barrel, and into contact with the applicator pad 110. For example, the reservoir 150 can include a breakable neck portion that separates from a body portion of the reservoir 150 to release liquid from the reservoir 150 in response to the reservoir 150 being urged against an internal ramp or incline. As another example, a neck portion of the reservoir 150 can be broken from the reservoir due to engagement between a deformable sidewall of the applicator device 170 and the neck portion due to manipulation of the sidewall by a user.

In some embodiments, the reservoir 150 can include a weakened or pre-scored area (e.g., a circumferential region or sidewall region) configured to preferentially break when a breaking force is applied to the weakened or pre-scored area. For example, in some embodiments, the weakened or pre-scored area can be at a mid-point location of the reservoir 150 along a central axis of the reservoir 150, adjacent a shoulder of the reservoir 150, and/or can be on or near a first (e.g., a distal) or a second (e.g., a proximal) end of the reservoir 150. The reservoir 150 can be configured to break (e.g., at a weakened or pre-scored area) due to a rotational, bending, and/or orthogonal force (relative to or along the central axis of the reservoir 150) applied to the reservoir 150. In some embodiments, such a rotational, bending, and/or orthogonal force can be applied via twisting and/or bending the grip 140 within which the reservoir 150 is disposed. In some embodiments, the breaking force can be applied via displacing (e.g., squeezing) a portion of the grip (e.g., a deformable sidewall portion) into sufficiently forceful contact with a sidewall of the reservoir 150 to break the reservoir 150 and release the contents of the reservoir 150. In some embodiments, the breaking force can be applied via rotating or translating a second portion of the grip 140 relative to a first portion of the grip 140 to apply the breaking force to the reservoir 150.

In some embodiments, the release mechanism 160 can include a force concentrating component (also referred to as a stress concentrating component) (e.g., a ball such as a steel ball or projection such as a convex or sharp tipped projection like a carbide tip) disposed on an inner surface of the grip 140 and configured to be urged toward a sidewall of the reservoir 150 (e.g., as a result of bending of the grip 140, squeezing or pushing an exterior portion of the grip 140 toward the reservoir 150, or rotating a second portion of the grip 140 relative to a first portion of the grip 140) to concentrate a breaking force against a sidewall or end of the reservoir 150 and break (e.g., shatter) the reservoir 150. In some embodiments, the grip 140 can include a notched feature in a sidewall of the grip 140 such that the grip 140 can be more easily bent about a preferential axis or plane including the notched feature.

In some embodiments, the reservoir 150 and/or the grip 140 can be disposed in a vertical orientation during a wetting of the applicator pad 110 with the contents of the reservoir 150 and/or during application of pressure to the applicator pad 110 when disposed on a wound of the subject such that the reservoir 150 is elongated along a longitudinal axis intersecting a plane containing the applicator pad 110 in the initial configuration of the system 100. In some embodiments, the contents of the reservoir 150 can be configured to flow from the reservoir 150 to the applicator pad 110 through an open distal end of the grip 140. In some embodiments, the reservoir 150 and/or the grip 140 can be disposed in a horizontal orientation during a wetting of the applicator pad 110 with the contents of the reservoir 150 and/or during application of pressure to the applicator pad 110 when disposed on a wound of the subject such that the reservoir 150 is elongated along a longitudinal axis disposed substantially parallel to a plane containing the applicator pad 110 in the initial configuration of the system 100. In some embodiments, the contents of the reservoir 150 can be configured to flow from the reservoir 150 to the applicator pad 110 through a sidewall of the grip 140.

In some embodiments, the applicator device 170 can include a filter (not shown) between the reservoir 150 and the applicator pad 110 to prevent unwanted material (e.g., particles above a certain size and/or glass pieces) from reaching the applicator pad 110. In some embodiments, the applicator device 170 may not contain the reservoir 150, the release mechanism 160, and/or the fluid coupling 155, but instead just provide a handle by which the user may hold the applicator pad 110 to be able to apply the applicator pad 110 to the target wound tissue and apply distributed pressure to the applicator pad 110 to maintain pressure between the applicator pad 110 against the target wound tissue.

The grip 140 may be used to provide a distributed force (e.g., a uniformly distributed force) to the applicator pad 110, e.g., to increase the pressure that the applicator pad 110 may apply to target wound tissue during use, to enhance hemostasis. The grip 140 may be implemented in a variety of ways, including those described in specific embodiments below. For example, the grip 140 may include a plate (also referred to herein as a "fixation plate") disposed on a distal end of and extending laterally from a handle portion of the grip 140 and configured to contact and apply a distributed force against the applicator pad 110. In some implementations, the plate can be shaped and sized such that the plate has a larger length and width than the target wound tissue such that the plate can urge a sufficiently large portion of the applicator pad 110 into contact with the target wound tissue and maintain uniformly distributed pressure between the applicator pad 110 and the target wound tissue for a period of time. Thus, the grip 140 can be used to provide a sufficient hemostatic force against the target wound tissue (e.g. to generate sufficient pressure given the stiffness or modulus of the material(s) of which the applicator pad 110 is formed). In some embodiments, the grip 140 or a portion of the grip may be deformable (e.g., squeezable) to urge fluid from the reservoir 150 disposed within the grip.

In some embodiments, the applicator device 170 can selectively release the applicator pad 110. For example, the grip 140 can releasably engage with the applicator pad 110 via the pad connector 148 to apply the applicator pad 110 to a surface of the patient (e.g., to the target wound tissue). The pad connector 148 can disengage from the applicator pad 110 such that the grip 140 and pad connector 148 can be separated from the applicator pad 110, leaving the applicator pad 110 on the surface of the patient. In some embodiments, the pad connector 148 can include one or more adhesive strips configured to couple the grip 140 to the applicator pad 110 and to be removed from the grip 140 and/or the applicator pad 110 when the applicator pad 110 is disposed in contact with the wound of the subject without displacing the applicator pad 110 relative to the wound such that the grip 140 can be separated from the applicator pad 110 without displacing the applicator pad 110 relative to the wound. In some embodiments, the pad connector 148 can include complementary hook-and-loop fastener portions coupled to the grip 140 and the applicator pad 110 such that the grip 140 can be releasably coupled to the applicator pad 110 via decoupling the complementary hook-and-loop fastener portions. In some embodiments, the pad connector 148 can include a first engagement feature coupled to the applicator pad 110 and a second complementary engagement feature coupled to the grip 140. The second complementary engagement feature can be configured to releasably engage with the first engagement feature (e.g., via receiving a portion of the first engagement feature within an opening of the second engagement feature due to, for example, relative rotation between the features, or via receiving a portion of the first engagement feature between opposing arms of the second engagement feature). In some embodiments, the pad connector 148 can include a latch portion disposed on the grip 140 configured to engage with a hook portion disposed on the applicator pad 110.

In some embodiments, the applicator pad 110 can include or be coupled to the pad retainer 135, which can be configured to maintain the applicator pad 110 in contact with the target wound tissue. The pad retainer 135 can include, for example, adhesive on a skin-contacting side of the applicator pad 110 (e.g., disposed around at least a portion of a perimeter of the applicator pad 110). In some embodiments, the pad retainer 135 can include an adhesive foam disposed about a perimeter of the applicator pad 110. In some embodiments, the pad retainer 135 can include adhesive strips having a first portion coupled to an upper surface of the applicator pad 110 and having a second portion configured to be coupled to a subject's skin to retain the applicator pad 110 in place relative to a wound on the skin. In some embodiments, the pad retainer 135 can include a bandage configured to be placed over at least a portion of the applicator pad 110. In some embodiments, the bandage can be formed as a wrap configured to be wrapped around a portion of the subject's body including the wound (e.g., an arm or a leg). In some embodiments, the bandage can be formed as a bandage having an adhesive perimeter greater than the perimeter of the applicator pad 110 and configured to be applied over the top of the applicator pad 110. In some embodiments, the bandage can include a convex portion configured to be aligned with the wound and placed in contact with the upper surface of the applicator pad 110 such that, when the applicator pad 110 is disposed on the wound and the bandage is applied over the applicator pad 110, the convex portion can apply targeted pressure to the wound via the applicator pad 110 that is greater than if the bandage did not include a convex portion. In some embodiments, after a period of time, the convex portion can be removed from the subject, leaving the applicator pad 110 in place in contact with the wound.

In some embodiments, the applicator device 170 can be implemented as a pipette. The pipette may be configured in a manner most suitable for the accuracy and precision needed for the size and location of the wound. For example, the pipette may be configured to be positioned within a patient's nostril.

The bleeding treatment system 100 may include a user guide 190. The user guide 190 may include instructions for operation of the bleeding treatment system 100 to treat a person experiencing a wound requiring cessation of bleeding. The instructions may be in the form of textual and/or graphical information, which may be presented on fixed substrate (e.g. paper) or on a display (e.g. screen), and/or may use other sensory modalities, including audible (spoken instructions) and/or tactile (haptic feedback to the user). The user guide 190 may be disposed on (e.g. printed on) or coupled to (e.g. mechanically attached) any one or more component(s) of the bleeding treatment system 100, including the applicator device 170, the packaging 190, the applicator pad 110, and/or the reservoir 150. The user guide 190 may be separate from any of the components of the bleeding treatment system 100, but may be associated therewith, e.g. disposed in the packaging 195 along with the other components of the bleeding treatment system 100. In some embodiments, the user guide 190 may be implemented in whole or in part in software usable on a device such as smart phone, e.g. may be the form of an "app" that can be downloaded onto the smart phone and launched by a user in preparation for using the bleeding treatment system 100.

In some embodiments, the user guide 190 or another informational label disposed on or included with the system 100 can include an information label including user instructions such as: "Only apply only to superficial bleeding areas less than 1 inch. Press down with the topical applicator pad over the wound for 5 minutes. Place an adhesive bandage over the wound. If bleeding does not stop, seek professional medical treatment. If you feel weak or dizzy, call 911 immediately and do not use this device. Not to be used in the mouth. Not to be used on deep wounds. Do not use if you have a history of seizures. Do not use for penetrating wounds or puncture wounds (gunshot, knife, etc.)."

In some embodiments, the user guide 190 or another informational label disposed on or included with the system 100 can include an information label including user instructions such as: "Only apply only to superficial bleeding wounds 3 inches or less in length. Push the release mechanism to break the medication. Allow the medication to fully cover the topical applicator. Press down with the device over the wound for 10 minutes. Place an adhesive bandage over the wound. If bleeding does not stop or if you feel dizzy, weak, or fatigued, seek professional medical treatment IMMEDIATELY. Not to be used in the mouth. Not to be used on deep wounds. Do not use if you have a history of seizures. Do not use for penetrating wounds or puncture wounds (gunshot, knife, etc.). Do not drink this medication. Keep away from children or infants."

In some embodiments, the user guide 190 or another information label disposed on or included with the system 100 can include one or more statements indicating one or more of the following: (i) remove the applicator cap before pressing down with the device over the wound; and (ii) peel the topical applicator from the rest of the device and use an adhesive bandage to keep the topical applicator on the wound.

In some embodiments, the user guide 190 or another informational label or stamp on the system 100 can include an expiration date. For example, the system 100 may have a shelf life from a date of manufacture of three years, more than three years, or less than three years. In some embodiments, the user guide 190 or another informational label or stamp on the system 100 can include a lot number and/or a date of manufacture. In some embodiments, the user guide 190 or another informational label or stamp on the system 100 can include a bar code and/or Quick Response (QR) code.

The packaging 195 may be implemented in the same manner as any known medical device packaging, to contain the other components of the bleeding treatment system 100, to protect the components from the environment, and optionally to preserve sterility of the components. The packaging 195 is preferably configured to be readily opened by a user, e.g. by peeling a cover from a tray, when the user desires to access and use bleeding treatment system 100. The packaging 195 may be implemented in many other ways, including for example a bag or box. The system 100 is preferably intended for a single user and one wound site application. The system 100 is preferably intended to be discarded after use, and may optionally include a container for safe disposal. In some embodiments, the system 100 can be originally supplied to the user in the packaging 195 that can also be used for disposal. In some embodiments, the packaging 195 and/or disposal container can be a re-sealable bag and/or can include a biohazard label and/or disposal instructions.

The medication(s) described herein may be any medication that would be desirable to deliver to the patient experiencing a wound requiring cessation of bleeding, preparatory to or as part of treatment of the wound. Categories of medications may include vasoconstrictors, antifibrinolytics, antibiotics, recombinant clotting factor medications, local anesthetics, analgesics, buffering agents, calcium, alcohols/ antiseptics (e.g., a chlorhexidine solution such as a solution of chlorhexidine and isopropyl alcohol and/or ethyl alcohol), or any combination thereof. A vasoconstrictor may be useful to help bleeding vessels constrict prior to or simultaneously with administration of a hemostatic medication such as an antifibrinolytic, and may desirably be delivered to the target wound tissue at or around the site of the bleeding before, during, and/or after application of applicator pad 110 to the target wound tissue. Suitable vasoconstrictors may include phenylephrine, oxymetazoline (Afrin), and epinephrine. An antifibrinolytic agent may be useful to prevent blood clot breakdown, and may also desirably be delivered to the wound tissue at or around the site of the bleeding before, during, and/or after application of applicator pad 110 to the target wound tissue. Suitable antifibrinolytics may include aminocaproic acid, tranexamic acid (TXA) (e.g., dry or lyophilized TXA or a liquid formulation including TXA), aprotinin, protaaminomethylbenzoic acid, and fibrinogen. Protamine, a reversal agent for the anticoagulant heparin could be used before, during, or after use of the above medications. The medication(s) can include, for example, protamine sulfate. As noted above, the bleeding treatment system 100 and medication(s) may be particularly helpful for treatment of patients who are susceptible to bleeding or for whom it may be difficult to achieve hemostasis, such as patients who are taking anticoagulation and/or antiplatelet medications (identified above).

In some embodiments, the medication can include a pharmaceutical composition including a therapeutically effective amount of TXA, one or more antibiotic(s), one or more anesthetic(s), one or more non-steroid anti-inflammatory drug(s), and/or an excipient or carrier that facilitates local administration. For example, in some embodiments, the therapeutically effective amount of tranexamic acid is between 1-70% by weight of the composition. In some embodiments, the one or more antibiotic(s) can include sulfacetamide, mupirocin, erythromycin, clindamycin, sulfadiazine, mafenide, tetracycline, bacitracin, neomycin, and polymyxin B. In some embodiments, the one or more antibiotic(s) can include bacitracin, neomycin, and polymyxin B. In some embodiments, the excipient or carrier permits the composition to remain in contact with a bleeding wound. In some embodiments, the excipient or carrier comprises an ointment, a cream, a liniment, a paste, a lotion, a gel, a hydrogel, a liposome, a spray, an aerosol, a solution, or an emulsion. In some embodiments, the excipient or carrier permits instillation of the composition. In some embodiments, the one or more anesthetic(s) can include lidocaine, proparacaine, procaine, tetracaine and combinations thereof. In some embodiments, the one or more non-steroid anti-inflammatory drug(s) can include ketorolac, ketoprofen, flurbiprofen, bromfenac, diclofenac and/or combinations thereof.

In some embodiments, the medication can include analgesics, including but not limited to, opiates such as codeine, morphine, oxycodone, etc.; acetaminophen; anti-inflammatory agents, including nonsteroidal anti-inflammatory drugs, aspirin, etc.; antibiotics or another antimicrobial drugs or compounds; antihistamines (e.g., cimetidine, chlorpheniramine maleate, diphenhydramine hydrochloride, and promethazine hydrochloride); antifungal agents; ascorbic acid; rutin; thrombin; botanical agents; etc.; and combinations thereof. The medication can also include magnesium sulfate, sodium metaphosphate, calcium chloride, dextrin, and combinations thereof.

In some embodiments, the medication can include sterile water and/or normal saline (which can be included as a carrier). In some embodiments, the medication can include between about 50% and about 100% tranexamic acid and between about 50% and about 0% sterile water or normal saline. In some embodiments, the medication can include between about 10% and about 50% tranexamic acid and between about 90% and about 50% sterile water or normal saline. In some embodiments, the medication can include between about 50% and about 90% tranexamic acid and between about 10% and about 50% sterile water or normal saline. In some embodiments, the medication can include at least one of a liquid and a gel. In some embodiments, the medication can have a viscosity between about 0.75 millipascal-seconds and about 0.98 millipascal-seconds at about +25 degrees Celsius.

In some embodiments, the reservoir 150 can include an activation liquid such as sterile water or saline and the applicator pad 110 can include a dried (e.g., lyophilized) medication configured to be activated by the activation liquid upon release of the activation liquid from the reservoir 150. In some embodiments, the applicator pad 110 can include dried medication configured to be activated by blood flowing from the wound when the applicator pad 110 is disposed in contact with the wound such that activation liquid disposed within the applicator device 170 is not needed or is supplemental. In some embodiments, the applicator pad 110 can include wetting agents to promote dissolution of the dried medication.

In some embodiments, the medication(s) may comprise an antifibrinolytic in an amount of about 50 mg/mL to about 300 mg/mL, including about 50 mg/mL, about 100 mg/mL, about 150 mg/mL, about 200 mg/mL, about 250 mg/mL, or about 300 mg/mL. In some embodiments, the medication(s) may also include a colored dye to indicate that the medication(s) has been dispensed to the wound and is of a composition to be human viewable based on skin color and blood color (before and after clotting). In other embodiments, the medication(s) may not contain a colored dye.

In some embodiments, the amount of medication(s) (e.g., of an antifibrinolytic such as TXA) included in the reservoir and/or provided from the reservoir to the target wound (e.g., the therapeutically effective amount) can be between about 1 mg and about 20 mg, between about 1 mg and about 5 mg, between about 5 mg and about 10 mg, between about 10 mg and about 15 mg, between about 15 mg and about 20 mg, and/or between about 10 mg and about 20 mg. In some embodiments, a larger amount of medication(s) can be included for treatment of larger target wound sizes.

In some embodiments, the reservoir(s) 150 and/or release mechanism 160 are configured such that a metered dose can be provided from the reservoir (e.g., to the applicator pad 110 and/or to the patient). The metered dose (e.g., of IV TXA) can be the amount of liquid disposed within the reservoir(s) 150 prior to use of the system 100. In some embodiments, the metered dose can be between about 1.5 mL and about 2.5 mL, between about 2.5 mL and about 4.5 mL, between about 3 mL and about 10 mL, between about 3 mL and about 7 mL, between about 1 mL and about 20 mL, between about 1 mL and about 1.5 mL, between about 2.5 mL and about 5 mL, between about 5 mL and about 10 mL, between about 10 mL and about 15 mL, or between about 15 mL and about 20 mL. For example, the reservoir 150 can include a metered dose of about 1 mL, or about 2 mL, or about 3 mL, or about 4 mL, or about 5 mL, or about 6 mL, or about 7 mL, or about 8 mL, or about 9 mL, or about 10 mL, or about 11 mL, or about 12 mL, or about 13 mL, or about 14 mL, or about 15 mL, or about 16 mL, or about 17 mL, or about 18 mL, or about 19 mL, or about 20 mL.

Figure 3A:
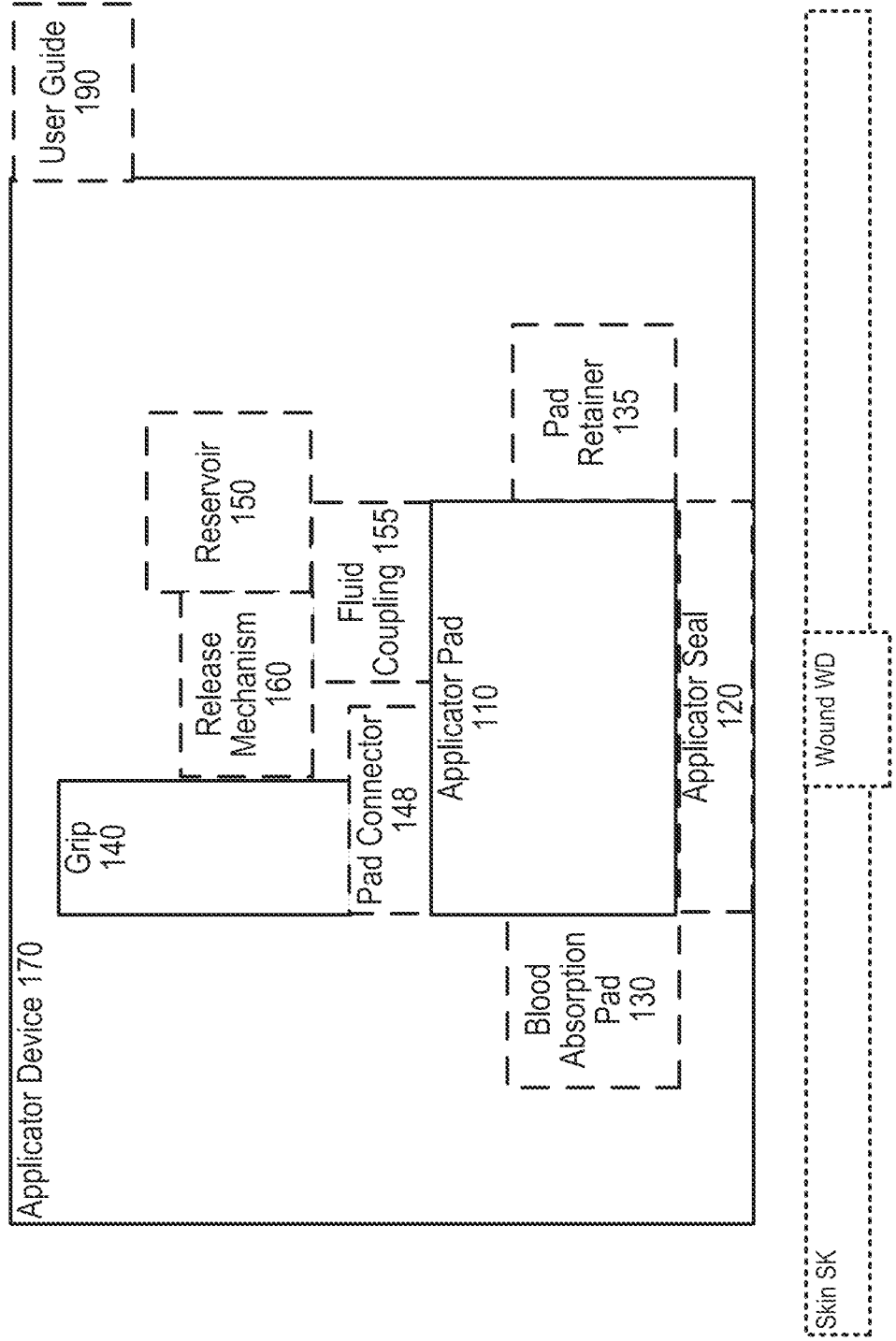
FIG. 3A is a schematic illustration of the bleeding treatment system of FIG. 3, with packaging removed from the bleeding treatment device, shown disposed near a wound on the skin of a patient.
Figure 3B:
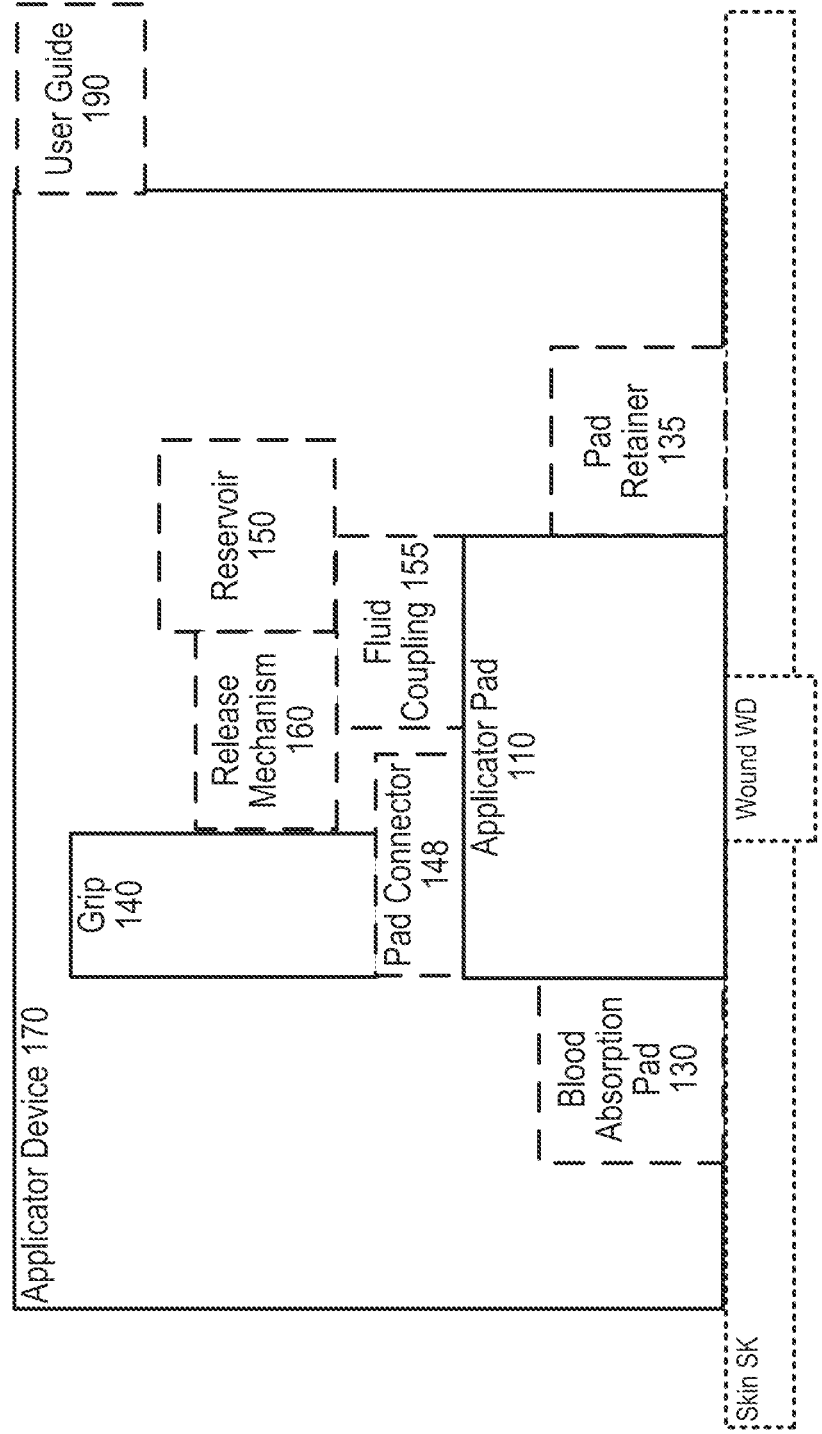
FIG. 3B is a schematic illustration of the bleeding treatment device of FIG. 3A with an optional applicator seal removed, shown with a portion of the bleeding treatment device disposed adjacent to the wound on the skin of the patient.
Figure 3D:
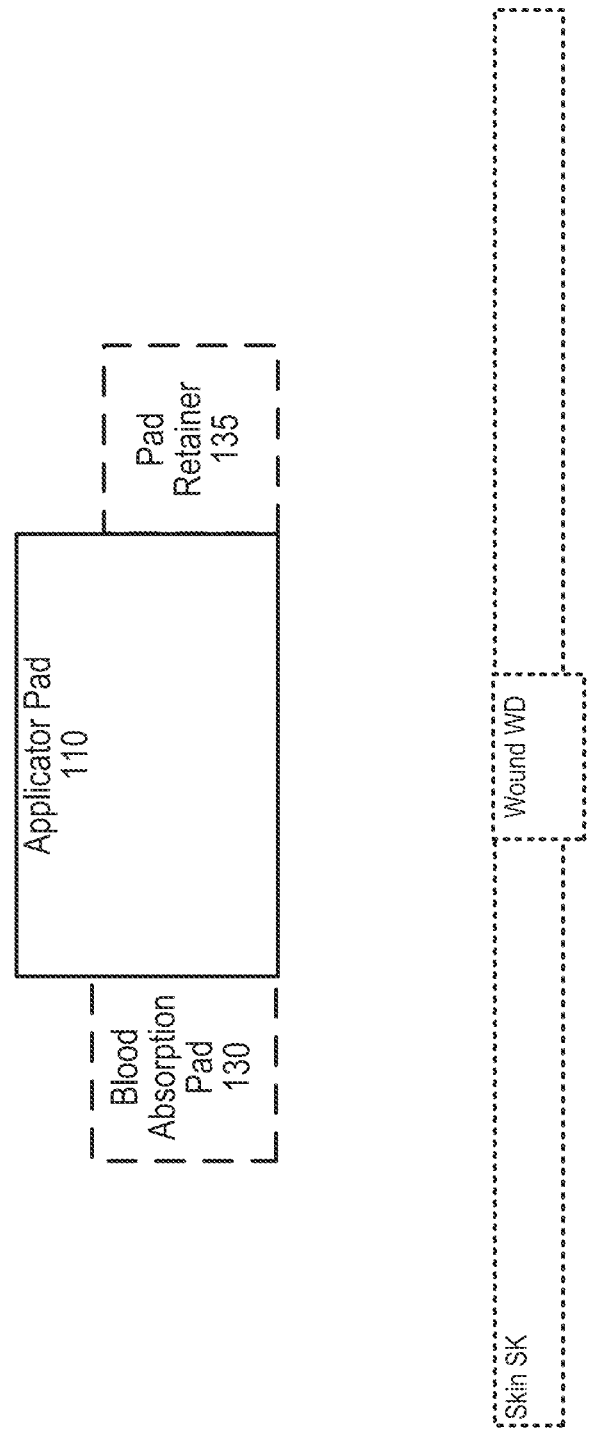
FIG. 3D is a schematic illustration of the bleeding treatment device of FIG. 3A, shown separated from the wound of the patient.
Figure 4:
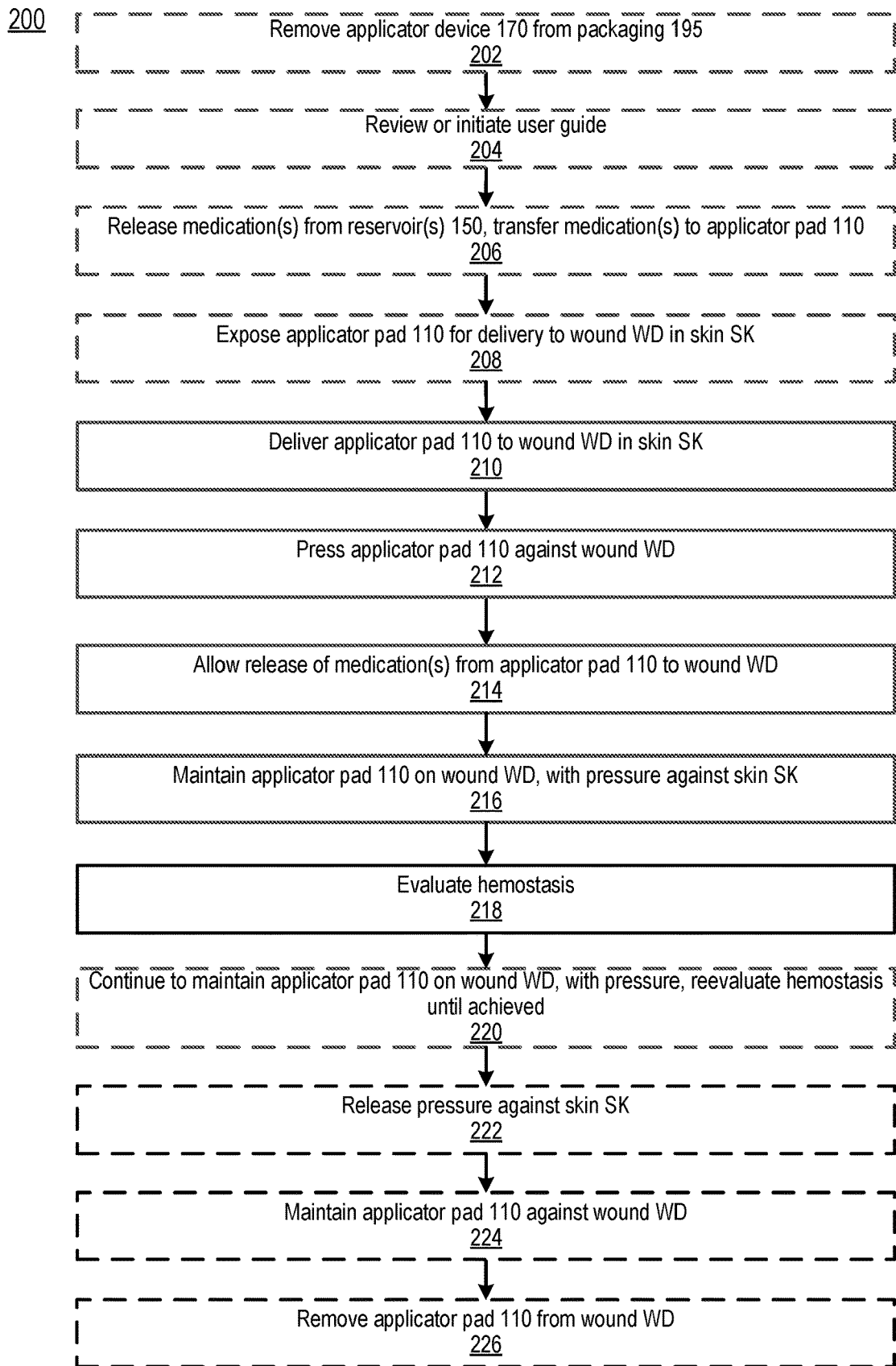
FIG. 4 is a flow chart of a method of using the bleeding treatment system of FIGS. 2 and 3A to 3D to treat a wound requiring cessation of bleeding.

A method of using bleeding treatment system 100 to treat a wound requiring cessation of bleeding is shown in FIG. 4 and illustrated with reference to FIGS. 3A to 3D. In some embodiments, the bleeding treatment system 100 can be operated with one hand (e.g., the hand of the subject having the wound in need of treatment or the hand of a caregiver). As shown in FIG. 4 and illustrated in FIG. 3A, in some embodiments, the applicator device 170 can be removed, at 202, from the packaging 195. The user guide 190 can optionally be reviewed or initiated, at 204. At 206, optionally, medication(s) can be released from the reservoir(s) 150 and transferred to the applicator pad 110. The applicator pad 110 can be exposed, at 208, for delivery to a wound WD in skin SK (e.g., via removal of the optional applicator seal 120).

As shown in the flow chart of a method 200 shown in FIG. 4, and as illustrated in FIG. 3B, the applicator pad 110 can be delivered, at 210, to the wound WD in skin SK. As shown in FIG. 3A and referenced above, in some embodiments, the applicator pad 110 can be delivered to the wound WD in skin SK within, extending from, or coupled to the applicator device 170 such that the applicator pad 110 is in contact with the wound WD and an area of skin SK surrounding the wound WD.

The applicator pad 110 can be pressed, at 212, against the wound WD in the skin SK. For example, the applicator pad 110 can be pressed against the wound WD in the skin SK via applying pressure (e.g., pressure distributed across the wound WD) to the applicator pad 110 using the grip 140. Alternatively or additionally, in some embodiments, the applicator pad 110 can be pressed against the wound WD in the skin SK via the applicator pad 110 via applying pressure to the applicator pad 110 with fingers of the user.

Medication(s) can be allowed to be released, at 214, from the applicator pad 110 to the wound WD. For example, in some embodiments, medication(s) can be released from the reservoir 150 via interaction with the release mechanism 160 such that the medication(s) flow to the applicator pad 110 via the fluid coupling 155 and then from the applicator pad 110 to the wound WD. In some embodiments, as described above, the applicator pad 110 may include medication(s) prior to use of the system 100 (e.g., via being pre-soaked), such that removal of the applicator seal 120 and application of the applicator pad 110 to the wound WD (and/or pressure applied to the applicator pad 110 when in contact with the wound WD) allows or causes medication(s) to travel into contact with the wound WD. In some embodiments, rather than or in addition to releasing medication(s) from the reservoir 150, an activation liquid such as saline can be released from the reservoir 150 to activate medication(s) included in the applicator pad 110 (e.g., in an initial dry state) such that the combination of medication(s) from the applicator pad and the activation liquid can flow into contact with the wound WD. In some embodiments, blood from the wound WD can contact and activate medication(s) in the applicator pad 110 (e.g., in an initial dry state) such that the combination of medication(s) from the applicator pad and the blood can flow into contact with the wound WD.

The applicator pad 110 can be maintained, at 216, against the wound WD with pressure applied by the grip 140 against the wound WD. At 218, hemostasis can be evaluated. For example, a hemostasis condition of the wound WD can be evaluated to determine if the hemostasis condition meets a target hemostasis condition. The hemostasis condition of the wound WD can be evaluated via any suitable method. For example, after a preset period of time (e.g., five or ten to thirty minutes), the applicator pad 110 can be removed and the wound WD checked to determine whether or not hemostasis has been achieved.

In some embodiments, after evaluating hemostasis at 218, the applicator pad 110 can continue to be maintained, at 220, against the wound WD while continuing to apply pressure to the wound WD and hemostasis can be reevaluated until achieved. For example, if the hemostasis condition of the wound WD fails to meet a target hemostasis condition, the applicator pad 110 can be maintained against the wound WD applying pressure to the wound WD for a period of time. The hemostasis condition can then be reevaluated to determine if the target hemostasis condition has been met. Such a cycle can continue until the target hemostasis condition has been met, at which time the applicator pad 110 can be removed from the wound WD.

In some embodiments, as illustrated in FIG. 3C, prior to removal of the applicator pad 110 from the wound WD, pressure can be released, at 222, against the wound WD. For example, in the instance of a grip 140 being used to apply pressure to the applicator pad 110, the grip 140 can be disengaged from the applicator pad 110 to reduce the pressure of the applicator pad 110 against the wound WD. In some embodiments, the applicator pad 110 can be maintained against the wound WD, at 224, after the pressure is released (e.g., after removal of the grip 140). In some embodiments, the applicator pad 110 can be maintained in place against the wound WD by the pad retainer 135. In some embodiments, a bandage or wrap can be applied to the applicator pad 110 to maintain the applicator pad 110 against the wound WD for a period of time. In some embodiments, the applicator pad 110 can continue to apply pressure to the wound WD after removal of the grip 140 (e.g., due to remaining in contact with the wound WD). In some embodiments, the applicator pad 110 can continue to apply pressure to the wound WD at least in part due to swelling of the applicator pad 110 or the blood absorption pad 130 due to liquid (e.g., blood) absorption. As illustrated in FIG. 3D, the applicator pad 110 can be removed, at 226, from the wound WD.

Figure 5:
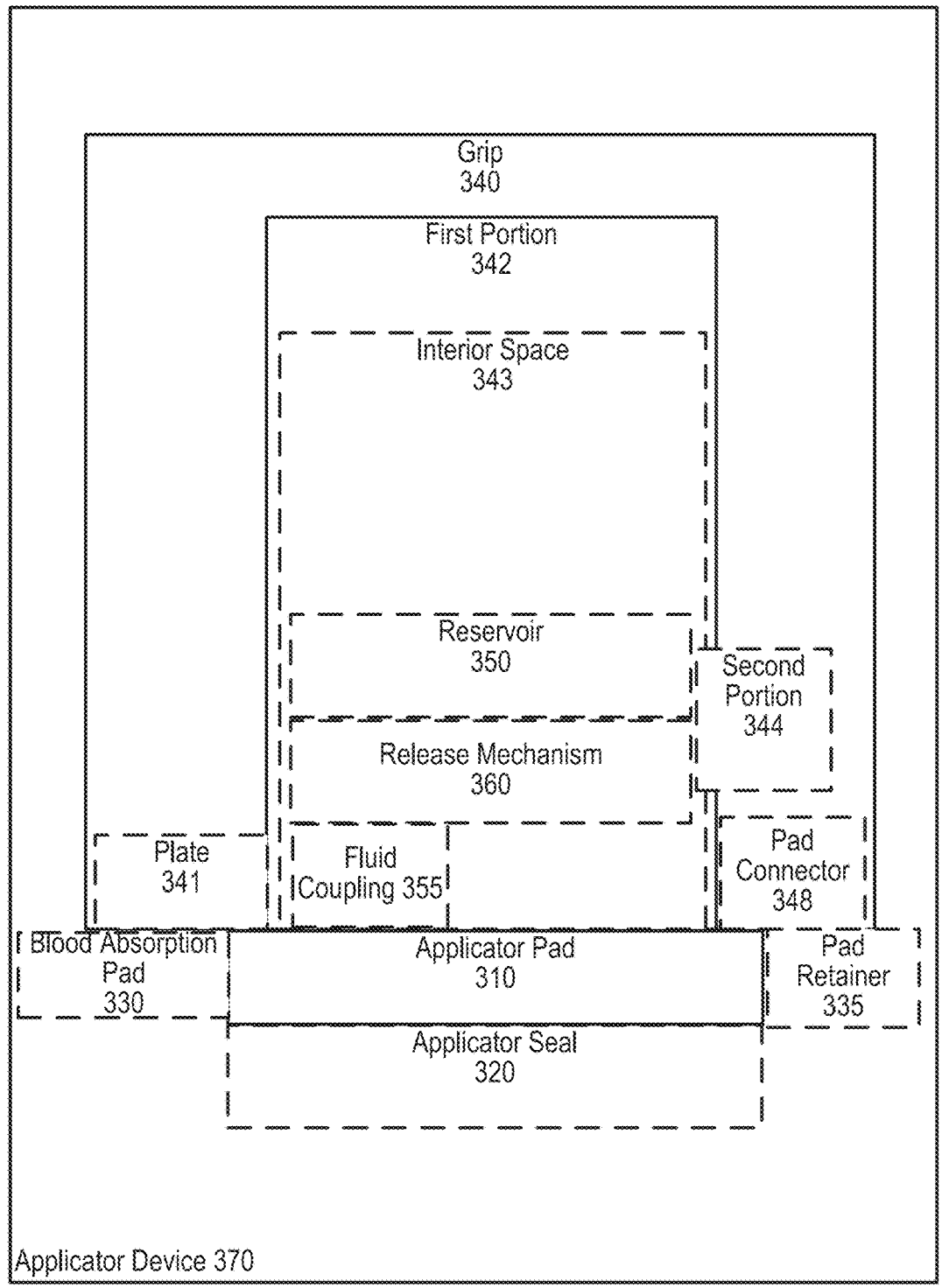
FIG. 5 is a schematic illustration of a bleeding treatment system, according to an embodiment.

FIG. 5 is a schematic illustration of a bleeding treatment system 300. The system 300 can be the same or similar in structure and/or function to any of the bleeding treatment systems described herein. The system 300 includes an applicator device 370, an applicator pad 310, and an optional reservoir 350. The applicator device 370 includes a grip 340 having a first portion 342 (also referred to as a "first section"). The first portion 342 optionally defines an interior space 343. In some embodiments, the first portion 342 optionally defines an open distal end such that the interior space 373 can be fluidically coupled to the applicator pad through the distal end of the first portion 342.

The first portion 342 can be formed in any suitable shape. For example, the first portion 342 can include a cylindrical or tubular housing. In some embodiments, the first portion 342 can include or be coupled to a plate 341 disposed at the distal end of the first portion 342 and configured to apply pressure to the applicator pad 310 and thus a target wound. The plate 341 may form a bottom surface of the grip 340. In some embodiments, such as when the grip 340 does not include a reservoir, the plate 341 can be formed as a continuous plate. In some embodiments, the plate 341 may be formed as a flange (e.g., a circumferential flange) extending from a bottom edge of the first portion 342.

In some embodiments, the grip 340 includes an applicator seal 320 configured to cover at least the distal or skin-contacting surface of the applicator pad 310 to prevent contamination of the applicator pad 310 and, optionally, leakage from or drying of the applicator pad 310 prior to use. The applicator seal 320 can be formed, for example, as a film (e.g., a peelable film). In some embodiments, the applicator seal 320 can be formed of a shrink wrap material covering the distal end of the applicator pad 310 and positioned over at least a portion of the length of the first portion 342.

The applicator pad 310 can be the same or similar in structure and/or function to any of the applicator pads described herein. For example, the applicator pad 310 can include and/or be coupled to an optional blood absorption pad 330 and/or an optional pad retainer 335. The blood absorption pad 330 and the pad retainer 335 can be the same or similar in structure and/or function to any of the blood absorption pads or pad retainers, respectively, described herein.

As shown in FIG. 5, the reservoir 350 can be disposed in the optional interior space 343. In some embodiments, the reservoir 350 can be configured to be displaced and/or pressurized such that liquid (e.g., medication and/or activating liquid such as saline) within the reservoir 350 flows from the reservoir 350 to the applicator pad 310. For example, the reservoir 350 can optionally include a release mechanism 360 and/or a fluid coupling 355 that may be the same or similar in structure and/or function to any of the release mechanisms and/or fluid couplings described herein. In some embodiments, the fluid coupling 355 can be a portion of the interior space 343 defined by the housing of the first portion 342 via which liquid can flow from the reservoir 350 to the applicator pad 310. In some embodiments, the fluid coupling 355 includes a separate tubular member defining a lumen through which liquid can flow from the reservoir 350 to the applicator pad 310.

In some embodiments, the delivery device 370 can include an optional second portion 344 (also referred to as a "second section"). In some embodiments, the second portion 344 can be configured to engage with the reservoir 350 and/or the release mechanism 360 to initiate transfer of liquid from the reservoir 350 to the applicator pad 310. In some embodiments, the second portion 344 can be formed as a plunger and advanced by a user (e.g., a self-administering home user, a caregiver, or a patient) relative to the first portion 342 (e.g., at least partially into the interior space 343 or while in contact with the reservoir 350 to advance the reservoir 350 itself) to apply pressure to the reservoir 350. In some embodiments, the second portion 344 can be disposed on a sidewall of the first portion 342 and configured to be urged laterally into the interior space 343 to apply pressure to the reservoir 350.

In some embodiments, the interior space 343 can be at least partially defined by an inner surface of a sidewall of the grip 340, and can be defined by the first portion 342 and/or the second portion 344. In some embodiments, the inner surface and/or the outer surface of the sidewall of the grip 340 (including the first portion 342 and the second portion 344) can have any suitable shape, such as a circular cylindrical shape, an oval cylindrical shape, an elliptical cylindrical shape, a tubular shape having two opposing flat sides coupled together by two opposing curved sides, and/or a prism shape, including a cube, rounded square prism, rectangular prism, rounded rectangular prism, triangular prism, pentagonal prism, hexagonal prism, etc. In some embodiments, the inner surface of the grip 340 defining the interior space 343 includes one or more rounded or beveled edges. In some embodiments, the inner surface of the grip 340 defining the interior space 343 includes a rounded rectangular prism shape with one or more rounded edges. In some embodiments, the interior space 343 is cylindrical.

In some embodiments, the release mechanism 360 can be coupled to the reservoir 350 and configured to transition from a closed condition to an open condition to allow medication to flow from the reservoir 350 and to the applicator pad 310 via the fluid coupling 355 in response to a pressure above a threshold pressure within the reservoir 350 (e.g., applied by the distal end of the second portion 344). For example, in some embodiments, the release mechanism 360 can include a weakened or frangible portion of a sidewall of the reservoir 350. In some embodiments, the release mechanism 360 includes a valve that transitions from a closed to an open condition upon an internal pressure of the reservoir 350 rising above a threshold pressure. In some embodiments, the release mechanism 360 can be a frangible portion of the reservoir 350 configured to break when pushed against an internal obstruction (not shown) such as a ramp portion within the interior space 343 such that the medication within the reservoir 350 can be released from the reservoir 350. In some embodiments, the first portion 342 can include a filter (not shown) between the reservoir 350 and the applicator pad 310 to prevent unwanted material from reaching the applicator pad 310.

Prior to use, the applicator device 370 can be disposed in an initial configuration. In the initial configuration, the applicator pad 310 can be coupled to the distal end of the grip 340. The applicator seal 320 can cover the applicator pad 310. To use the applicator device 370, the applicator seal 320 can be optionally removed and the grip 340 can be used to apply the applicator pad 310 to a wound. In embodiments including the reservoir 350, the release mechanism 360, and the fluid coupling 355, liquid (e.g., medication and/or activating agent such as saline) can be contained within the reservoir 350 prior to and optionally after applying the applicator pad 310 to the wound. To release the liquid from the reservoir 350 such that the liquid flows to the applicator pad 310, the second portion 344 can be configured to be moved relative to the first portion 342 (e.g., via translation relative to the first portion 342, radial movement relative to the first portion 342, and/or rotational movement relative to the first portion 342) to engage with the reservoir 350 and/or the release mechanism 360.

The applicator pad 310 can optionally be pressed against target wound tissue using the grip 340. The applicator pad 310 can optionally be maintained relative to the wound (e.g., without maintaining the grip 340 against the applicator pad 310) via coupling the applicator pad 310 to the skin via the pad retainer 335. The applicator pad 310 can be optionally separated from the applicator pad 310 via releasing the applicator pad 310 from the pad connector 348.

Figure 6A:
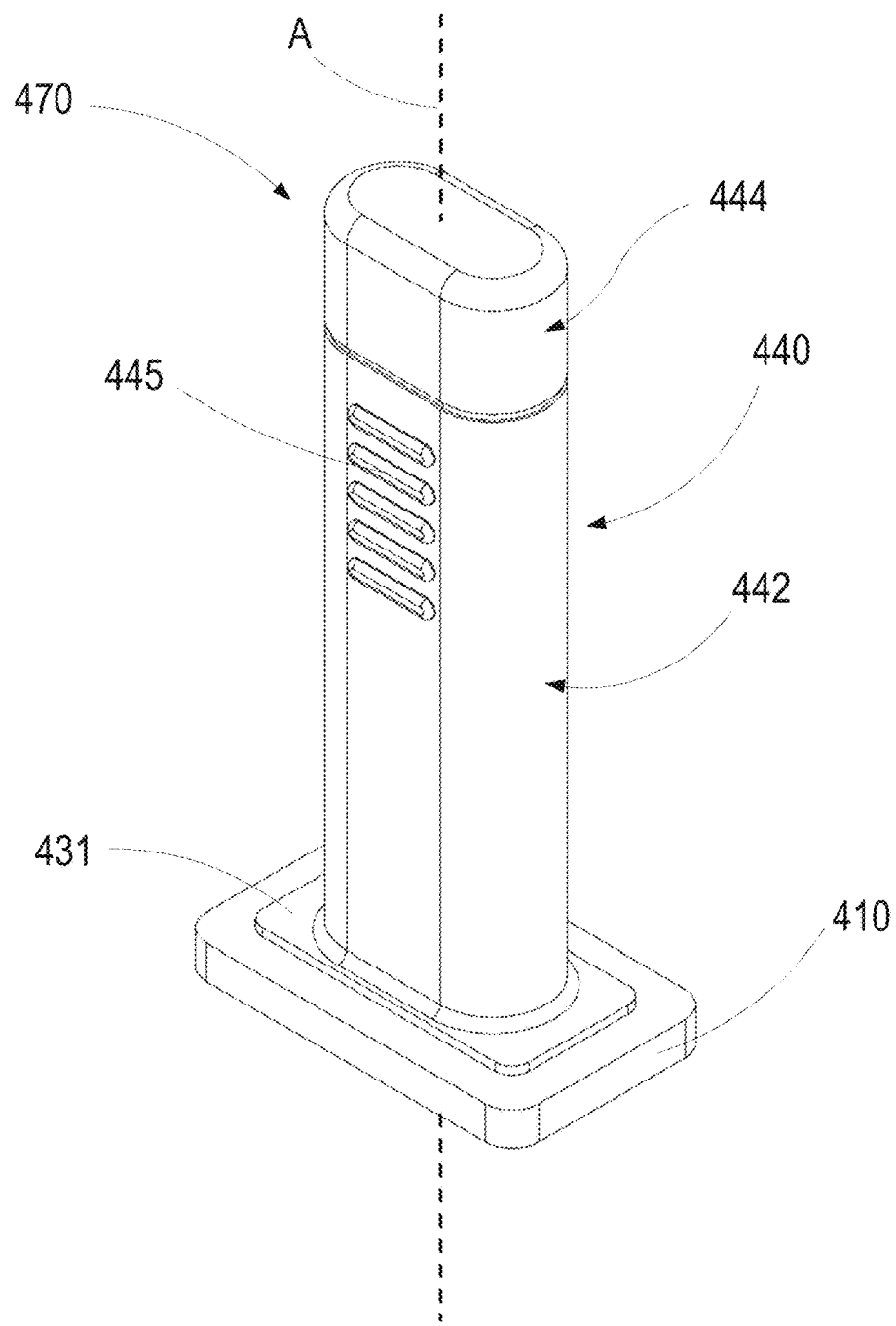
FIGS. 6A-6C are schematic illustrations of a bleeding treatment system, according to an embodiment.
Figure 6B:
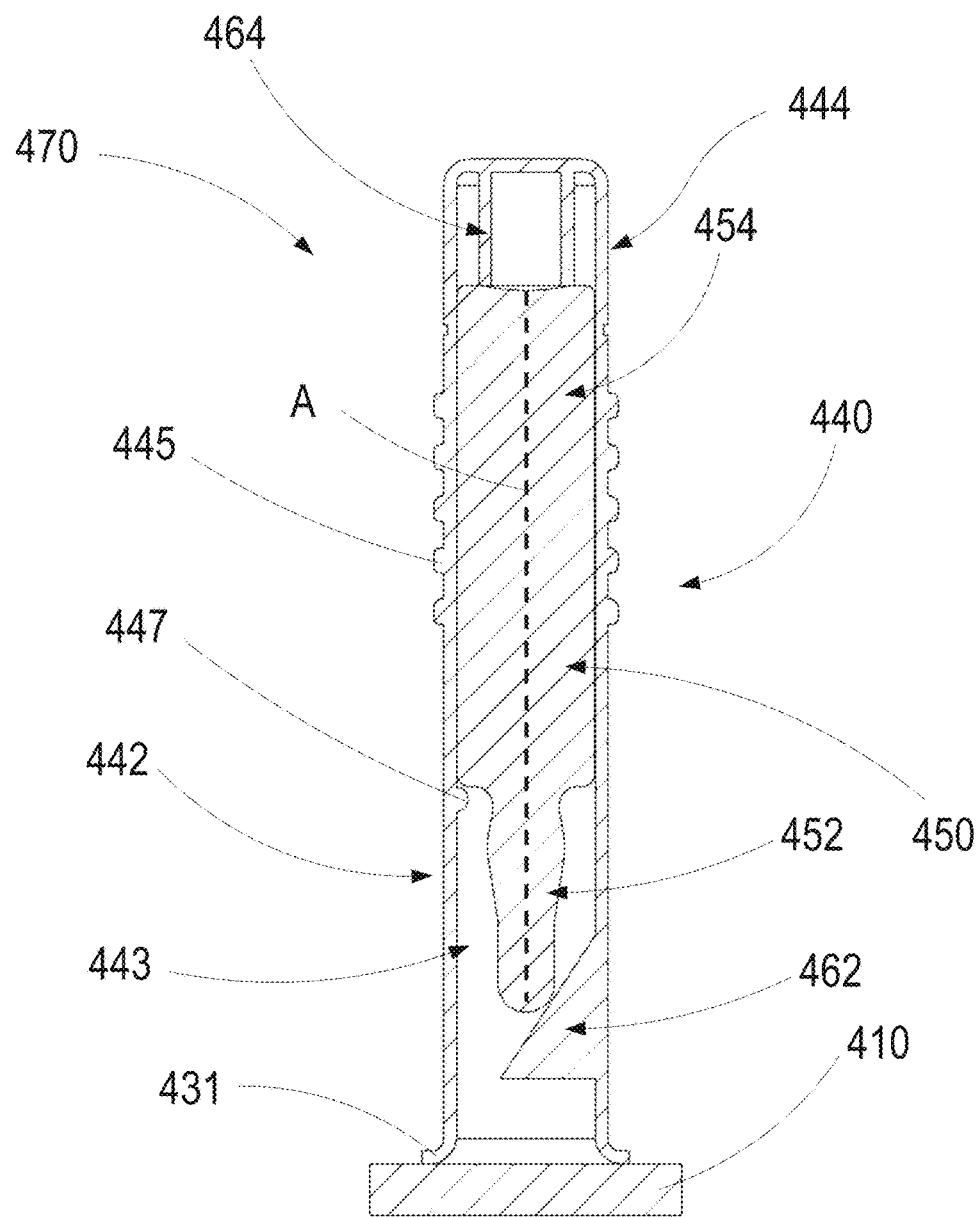
Figure 6C:
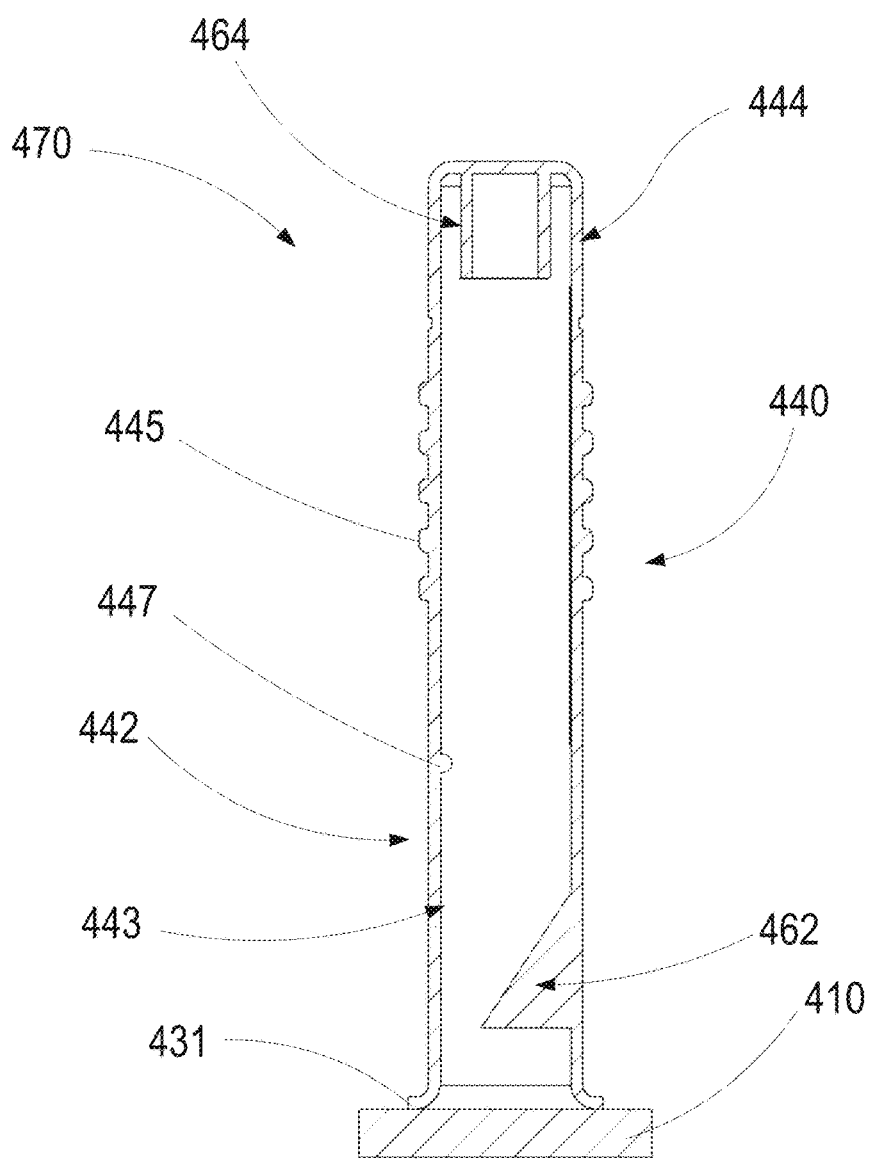
Figure 7A:
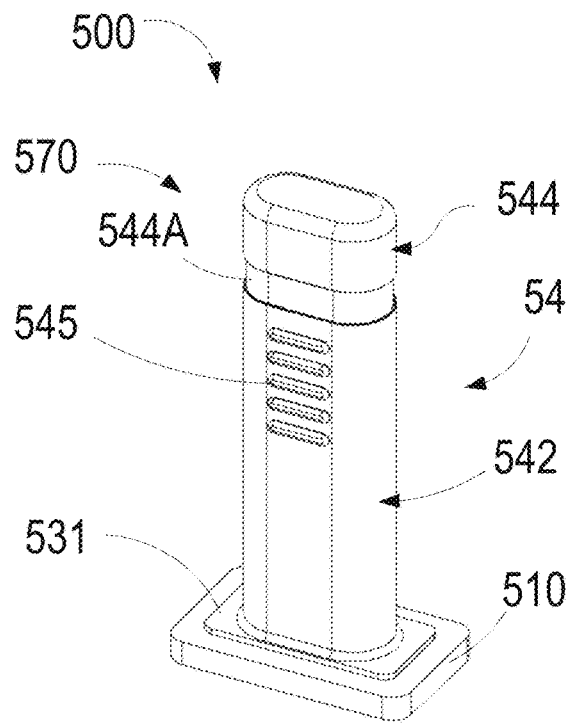
FIGS. 7A-7D are schematic illustrations of a bleeding treatment system, according to an embodiment, in an initial configuration.
Figure 7B:
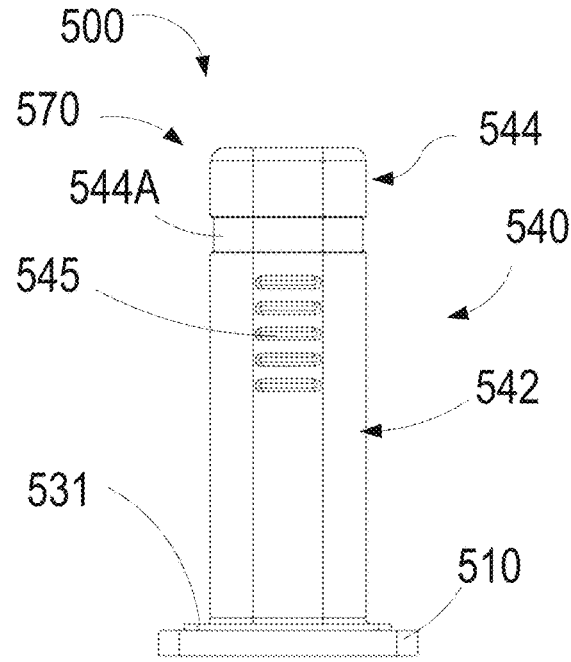
Figure 7C:
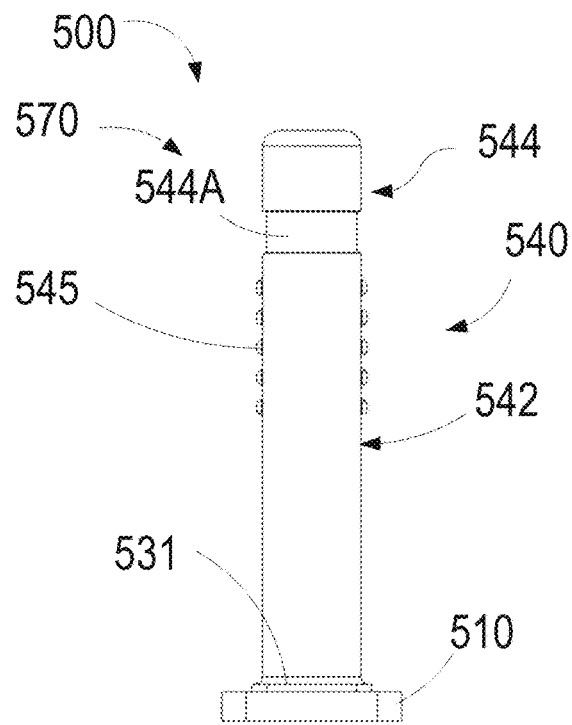
Figure 7D:
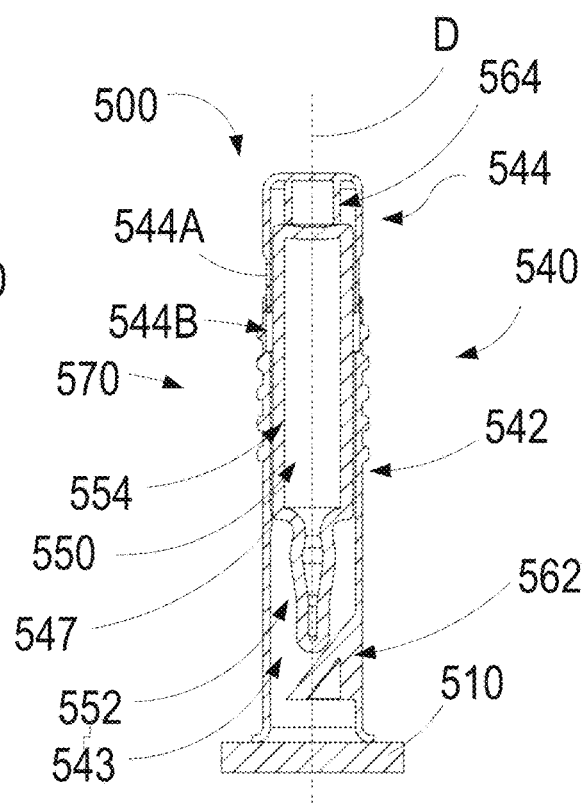
Figure 7E:
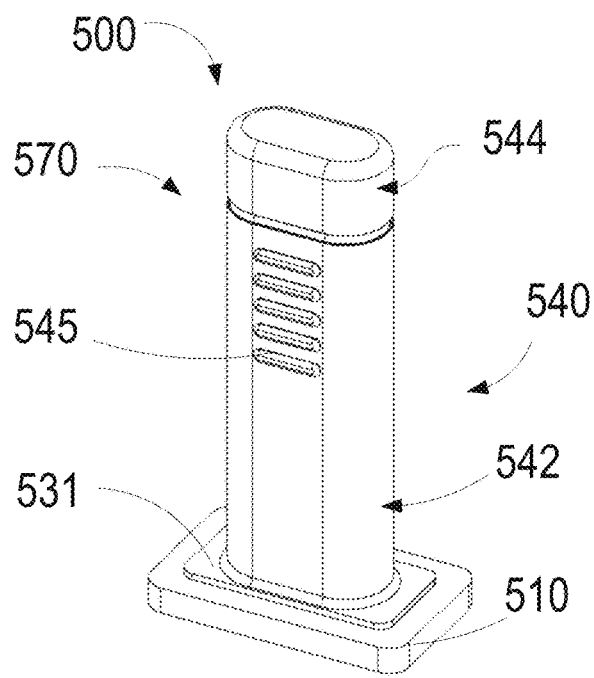
FIGS. 7E-7H are schematic illustrations of a bleeding treatment system in a wetting configuration.
Figure 7F:
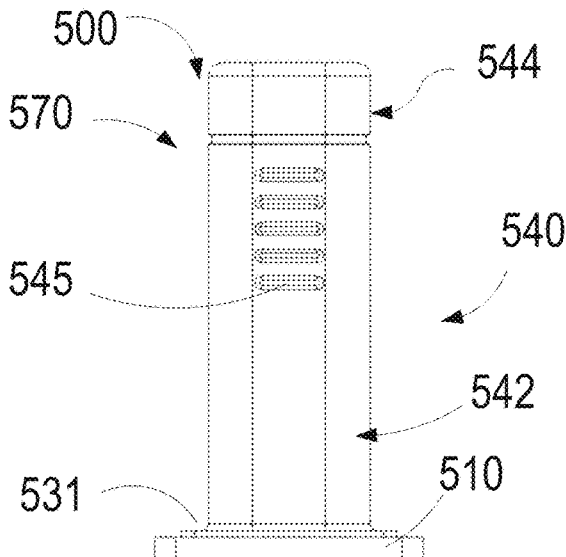
Figure 7G:
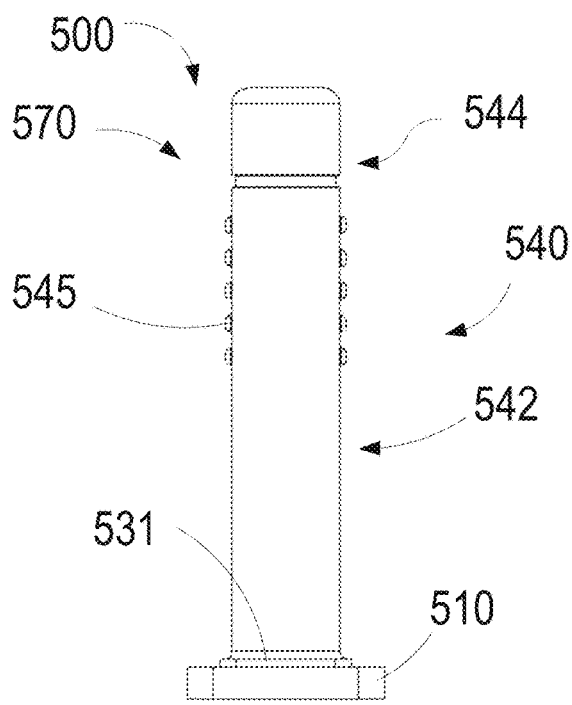
Figure 7H:
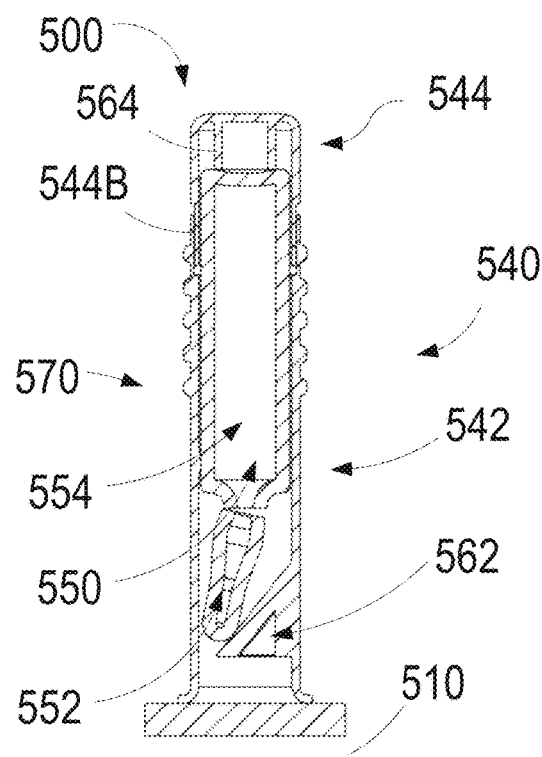

FIGS. 6A and 6B are a perspective view and a cross-sectional view of a bleeding treatment system 400. FIG. 6C is a cross-sectional view of the bleeding treatment system with a reservoir 450 of the bleeding treatment system 400 not shown. The system 400 can be the same or similar in structure and/or function to any of the delivery or treatment systems described herein. For example, the system 400 includes an applicator device 470, a reservoir 450, and an applicator pad 410. The applicator device 470 includes a grip 440 defining an interior space 443 and having an open distal end, a closed proximal end, and extending along a central longitudinal axis A. The grip 440 has a first portion 442 and a second portion 444, the second portion 444 being movable relative to the first portion 442. The reservoir 450 can be formed as an ampoule having a neck portion 452 and a body portion 454. The neck portion 452 can be narrower than the body portion 454 (e.g., can have a smaller diameter). The reservoir 450 can be disposed within the interior space 443 of the grip 440. The reservoir 450 can be oriented such that the neck portion 452 is distal of the body portion 454 and therefore closer to the open end of the grip 440. The interior space 443 can be at least partially defined by an inner surface of a sidewall of the grip 440, and can be defined by the first portion 442 and/or the second portion 444. The grip 440 (e.g., the inner surface and/or the outer surface) can be formed as shown in FIG. 6A, having a tubular shape having two opposing flat sides coupled together by two opposing curved sides. In some embodiments, the grip 440 can have any suitable shape, such as is described above with respect to the grip 340.

The first portion 442 can include a plate 431 having a distal or bottom surface extending laterally relative to the central axis A of the grip 440. The applicator pad 410 can be disposed on a distal end of the first portion 442 (e.g., coupled to the distal surface of the plate 431). The first portion 442 can include a ramp portion 462 (also referred to as a first release mechanism portion) extending partially into the interior space 443 of the first portion 442 such that the neck portion 452 can contact the ramp portion 462. The first portion 442 can also include one or more retaining portions 447 (e.g., flexible tab or bump portions) extending toward the central axis A of the first portion 442 and configured to contact a shoulder of the body portion 454 of the reservoir 450 as shown in FIG. 6B to retain the reservoir 450 in an initial proximal position until sufficient force is applied to a proximal end of the reservoir 450 to advance the reservoir 450 relative to the one or more retaining portions 447. The first portion 442 can also include one or more grip features 445 on an exterior surface of a sidewall of the first portion 442 to improve the grip of the user during handling of the grip 440. The grip features 445 can include any suitable surface feature to increase grip or friction, such as one or more ridges (as shown in FIG. 6A), concave and/or convex curvatures, and/or a textured or course surface.

The second portion 444 can include a projection 464 (also referred to as a second release mechanism portion). The first portion 442 and the second portion 444 can be coupled such that at least a portion of the second portion 444 can be advanced relative to the first portion 442 towards a distal end of the first portion 442. For example, the first portion 442 can be coupled to the second portion 444 via any suitable coupling mechanism, such as, for example, a flexible circumferential portion. To release liquid within the reservoir 450 such that the liquid flows to the applicator pad 410, the second portion 444 can be advanced distally relative to the first portion 442 (e.g., via pressing on a proximal end of the second portion 444) such that the second release mechanism portion 464 applies a force to the proximal end of the reservoir 450 to urge the reservoir 450 distally such that contact between the neck portion 452 of the reservoir 450 and the ramp 462 causes the neck portion 452 to separate (e.g., break) from a remainder of the reservoir 450 and allow liquid to flow from the reservoir 450, out of the distal end of the first portion 442, and to the applicator pad 410, resulting in the applicator pad 410 being wetted with the liquid from the reservoir 450.

In some embodiments, the first portion 442 can include a filter to prevent unwanted material (e.g., particles above a certain size and/or glass pieces) from reaching the applicator pad 410. Before or after wetting the applicator pad 410 with the liquid, the distal surface of the applicator pad 410 can be disposed against a wound of the subject. The grip 440 can then be maintained against the applicator pad 410 such that the plate 431 applies distributed pressure to the applicator pad 410 for a period time, as described with respect to the method 200 above. In some embodiments, the first portion 442 and/or the second portion 444 can be deformable (e.g., squeezable) to urge fluid (e.g., medication) from the reservoir 450. In some embodiments, the bleeding treatment system 400 can be operated with one hand (e.g., the hand of the subject having the wound in need of treatment). For example, the user can place a thumb on the proximal end of the second portion 444 and wrap the remaining fingers of the same hand around the sidewall of the grip 440 (e.g., around the first portion 442), with at least some of the remaining fingers in contact with the grip features 445. While gripping the grip 440 in this configuration, either before or after pressing the applicator pad 410 against the wound, the user can press the second portion 444 toward the applicator pad 410 with the user's thumb to release liquid from the reservoir 450 as described above.

FIGS. 7A-7D are schematic illustrations of a perspective, front, side, and cross-sectional view, respectively, of a bleeding treatment system 500 in an initial configuration. FIGS. 7E-7H are schematic illustrations of a perspective, front, side, and cross-sectional view, respectively, of the bleeding treatment system 500 in wetting configuration. The system 500 can be the same or similar in structure and/or function to any of the delivery or treatment systems described herein, such as, for example, the bleeding treatment system 400. For example, the system 500 includes an applicator device 570, a reservoir 550, and an applicator pad 510. The applicator device 570 includes a grip 540 defining an interior space 543 and having an open distal end, a closed proximal end, and extending along a central longitudinal axis D. The grip 540 has a first portion 542 and a second portion 544, the second portion 544 being movable relative to the first portion 542. The reservoir 550 can be formed as an ampoule having a neck portion 552 and a body portion 554. The neck portion 552 can be narrower than the body portion 554 (e.g., can have a smaller diameter). The reservoir 550 can be disposed within the interior space 543 of the grip 540. The reservoir 550 can be oriented such that the neck portion 552 is distal of the body portion 554 and therefore closer to the open end of the grip 540. The interior space 543 can be partially defined by an inner surface of a sidewall of the first portion 542 and the second portion 544.

The first portion 542 can include a plate 531 having a distal or bottom surface extending laterally relative to the central axis D of the grip 540. The applicator pad 510 can be disposed on a distal end of the first portion 542 (e.g., coupled to the distal surface of the plate 531). The first portion 542 can include a ramp portion 562 (also referred to as a first release mechanism portion) extending partially into the interior space 543 of the first portion 542 such that the neck portion 552 can contact the ramp portion 562. The first portion 542 can also include one or more retaining portions 547 (e.g., flexible tab or bump portions) extending toward the central axis A of the first portion 542 and configured to contact a shoulder of the body portion 554 of the reservoir 550 as shown in FIG. 6B to retain the reservoir 550 in an initial proximal position until sufficient force is applied to a proximal end of the reservoir 550 to advance the reservoir 550 relative to the one or more retaining portions 547. The first portion 542 can also include one or more grip features 545 on an exterior surface of a sidewall of the first portion 542 to improve the grip of the user during handling of the grip 540.

The second portion 544 can include a projection 564 (also referred to as a second release mechanism portion) extending into the interior space 543. The first portion 542 and the second portion 544 can be coupled such that at least a portion of the second portion 544 can be advanced relative to the first portion 542 towards a distal end of the first portion 542. For example, the second portion 544 can include a slidable engagement portion 544A and the first portion 542 can include a receiving portion 544B having a corresponding shape and a larger perimeter than the outer diameter of the slidable engagement portion 544A such that the slidable engagement portion 544A can be translated into the receiving portion 544B (e.g., via pressing on a proximal end of the second portion 544 and/or gripping opposing sidewalls of the second portion 544 and advancing the second portion 544 distally). During the translation of the slidable engagement portion 544A into the receiving portion 544B, the second release mechanism portion 564 can apply a force to the proximal end of the reservoir 550 to urge the reservoir 550 distally such that contact between the neck portion 552 of the reservoir 550 and the ramp 562 causes the neck portion 552 to separate (e.g., break) from a remainder of the reservoir 550 and allow liquid to flow from the reservoir 550, out of the distal end of the first portion 542, and to the applicator pad 510, resulting in the applicator pad 510 being wetted with the liquid from the reservoir 550.

In some embodiments, the first portion 542 can include a filter (e.g., disposed between the ramp 562 and the distal opening of the grip 540) to prevent unwanted material (e.g., particles above a certain size and/or glass pieces) from reaching the applicator pad 510. Before or after wetting the applicator pad 510 with the liquid, the distal surface of the applicator pad 510 can be disposed against a wound of the subject. The grip 540 can then be maintained against the applicator pad 510 such that the plate 531 applies distributed pressure to the applicator pad 510 for a period time, as described with respect to the method 200 above. In some embodiments, the bleeding treatment system 500 can be operated with one hand (e.g., the hand of the subject having the wound in need of treatment). For example, the user can place a thumb on the proximal end of the second portion 544 and wrap the remaining fingers of the same hand around the sidewall of the grip 540 (e.g., around the first portion 542), with at least some of the remaining fingers in contact with the grip features 545. While gripping the grip 540 in this configuration, either before or after pressing the applicator pad 510 against the wound, the user can press the second portion 544 toward the applicator pad 510 with the user's thumb to release liquid from the reservoir 550 as described above.

Figure 8:
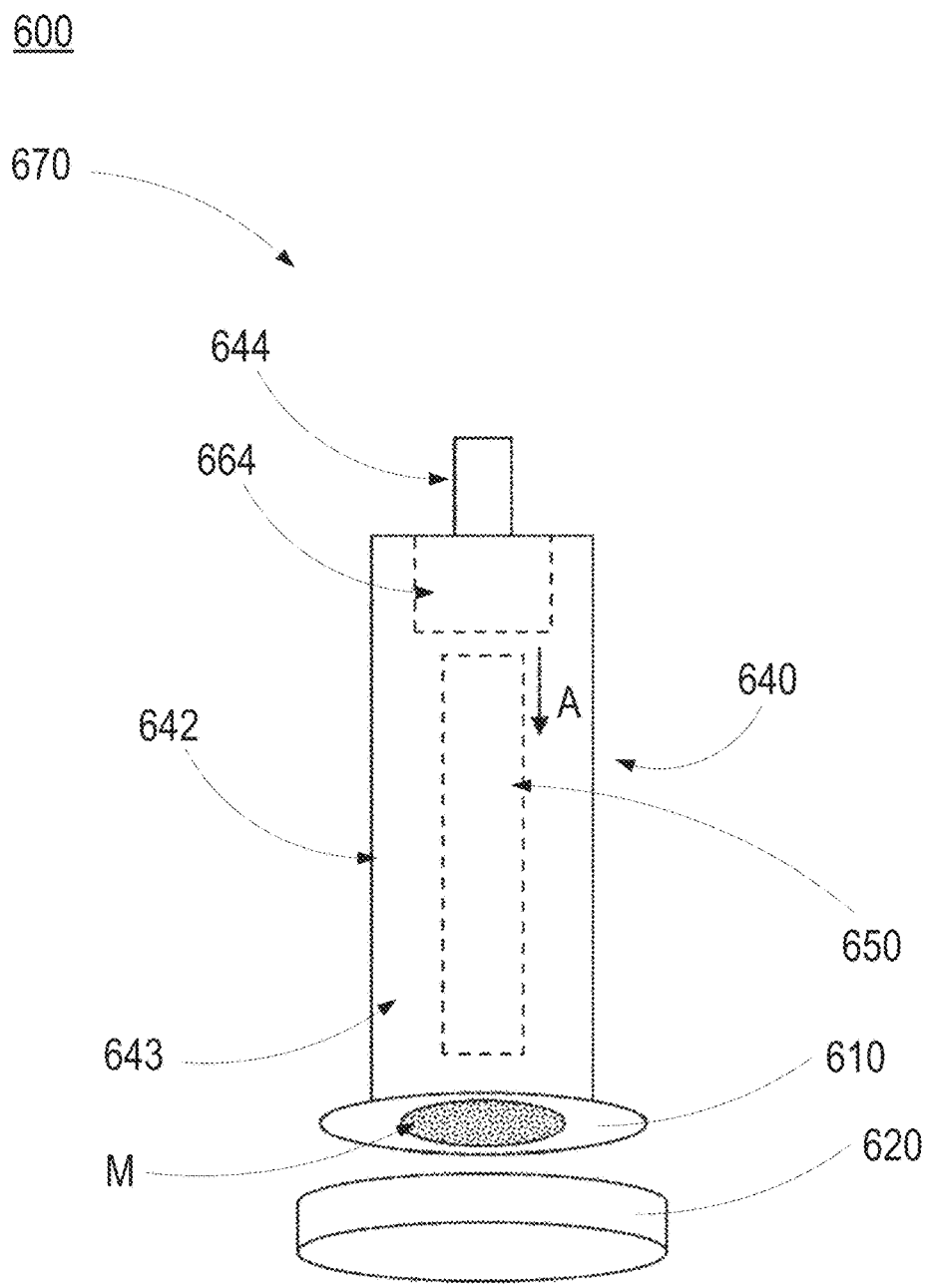
FIG. 8 is a schematic illustration of a bleeding treatment system, according to an embodiment.

FIG. 8 is a schematic illustration of a bleeding treatment system 600. The bleeding treatment system 600 can be the same or similar in structure and/or function to any of the bleeding treatment systems described herein, such as the bleeding treatment system 400 or the bleeding treatment system 500. For example, the bleeding treatment system 600 includes an applicator device 670, a reservoir 650, and an applicator pad 610. The applicator device 670 includes a cover 620 configured to be releasably coupled to the applicator pad 610 and, optionally, to the distal end of the first portion 642. The applicator device 670 includes a grip 640 including a first portion 642 and a second portion 644. The first portion 642 has an open distal end and an open proximal end such that the reservoir 650 can be inserted into the proximal end of the first portion 642 and disposed in the interior space 643. The second portion 644 can then be coupled to the proximal end of the first portion 642. The second portion 644 includes a projection 664 configured to extend into the internal space 643, contact the reservoir 650, and urge the reservoir and/or liquid within the reservoir toward the applicator pad 610 disposed on the distal end of the first portion 642.

To use the bleeding treatment system 600 to treat a wound and cease bleeding of the wound, the reservoir 650 can be inserted into the interior space 643 of the first portion 642. The second portion 644 can be coupled to a proximal end of the first portion 642. The cover 620 can be removed from the applicator pad 610. The second portion 644 can then be advanced distally in the direction of arrow A to apply pressure to the reservoir 650. Using any suitable reservoir and release mechanism structure, such as any of the reservoir and release mechanism structures described herein, liquid can be released from the reservoir 650 and flow to the applicator pad 610 such that medication M is disposed on the applicator pad 610.

Figure 9A:
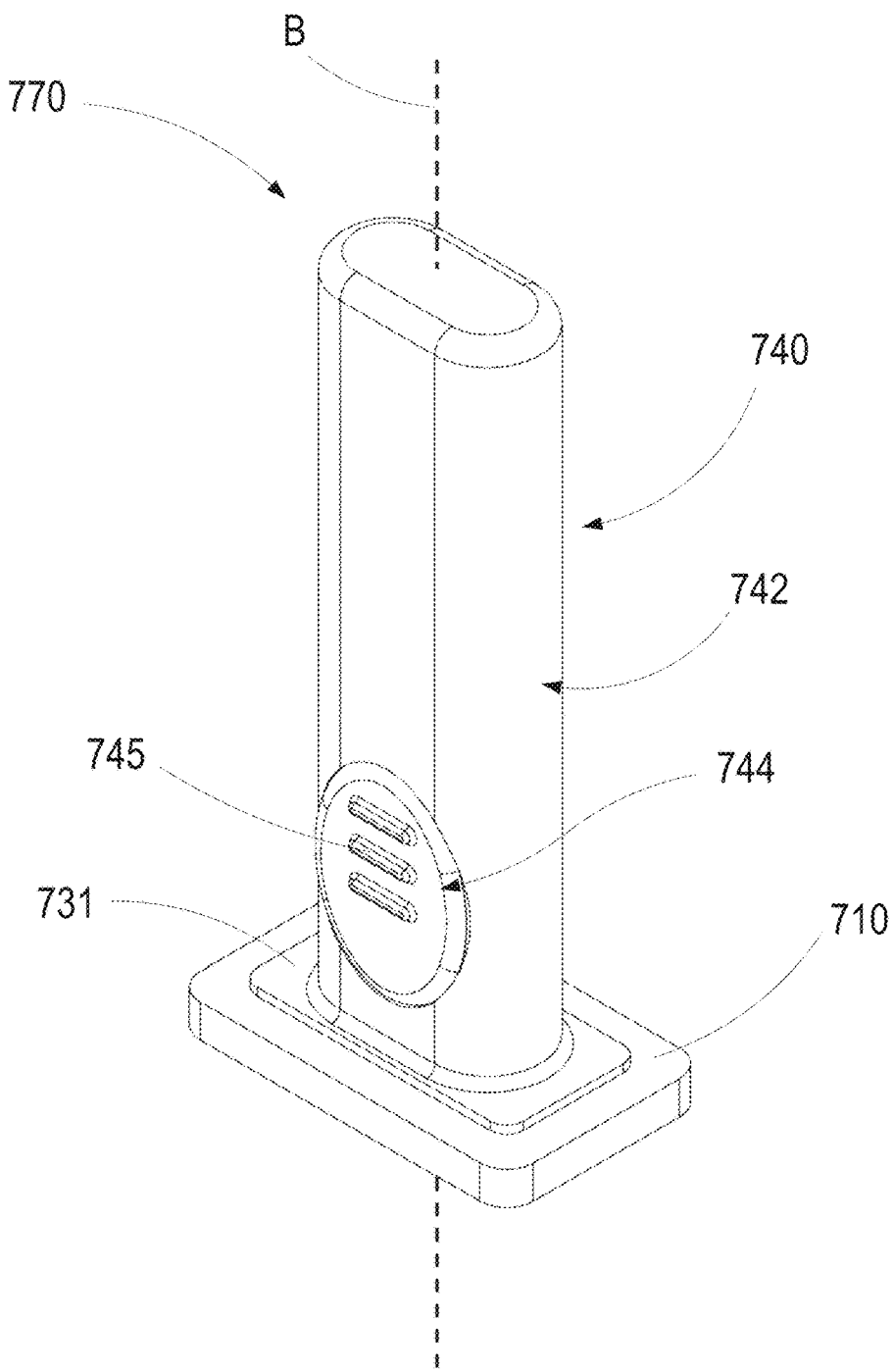
FIGS. 9A-9C are schematic illustrations of a bleeding treatment system, according to an embodiment.
Figure 9B:
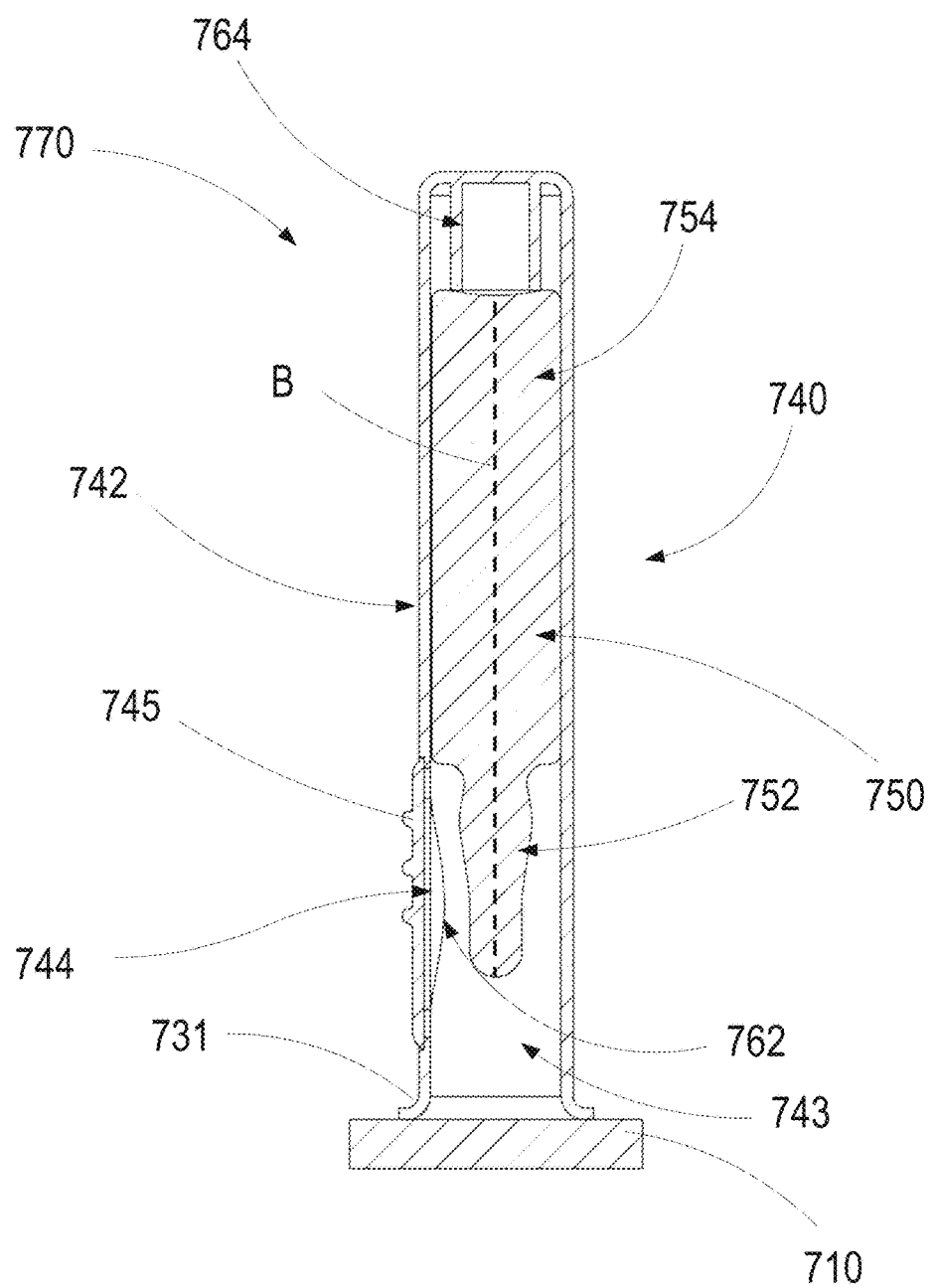
Figure 9C:
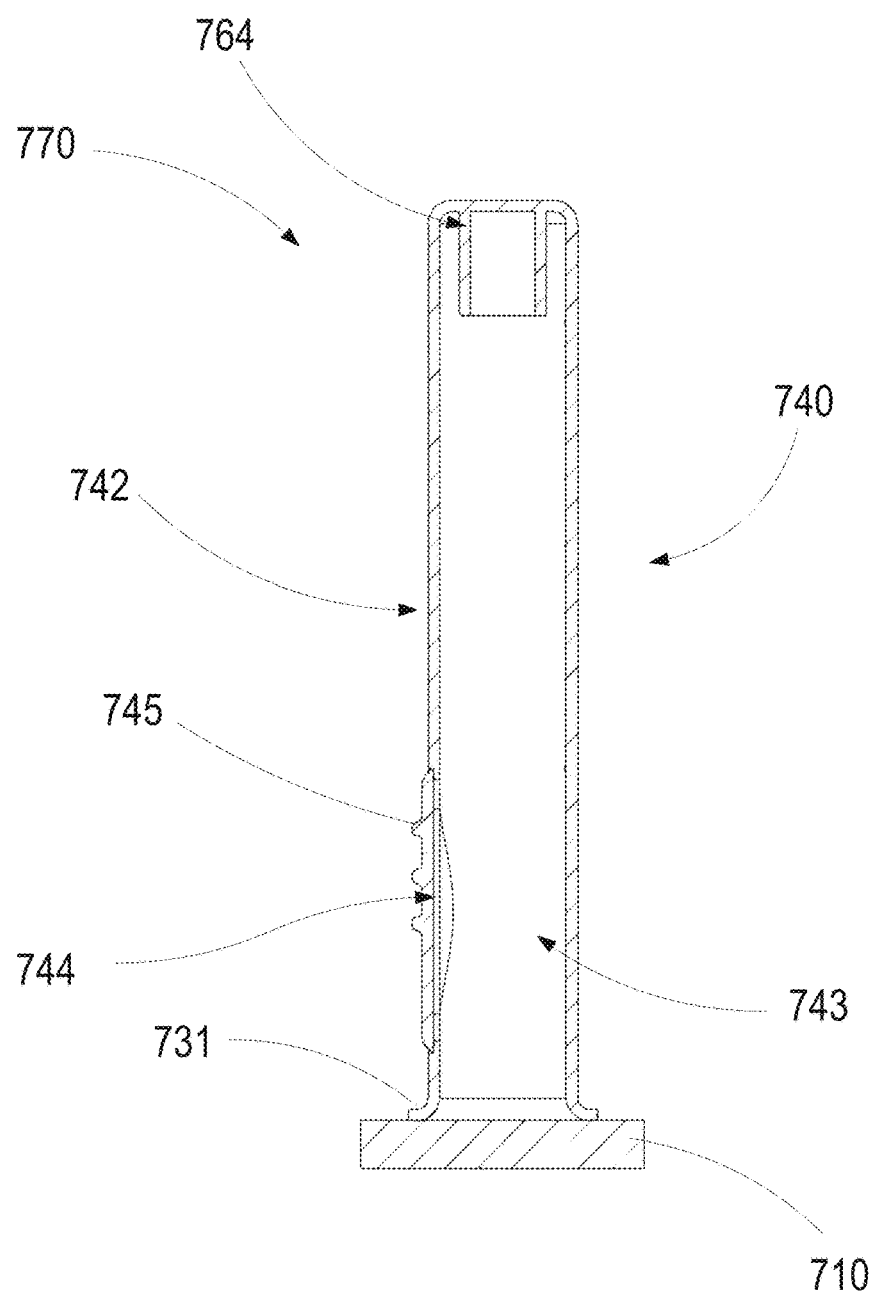

FIGS. 9A and 9B are a perspective view and a cross-sectional view of a bleeding treatment system 700. FIG. 9C is a cross-sectional view of the bleeding treatment system with a reservoir 750 of the bleeding treatment system 700 not shown. The system 700 can be the same or similar in structure and/or function to any of the delivery or treatment systems described herein. For example, the system 700 can include an applicator device 770, a reservoir 750, and an applicator pad 710. The applicator device 770 can include a grip 740 defining an interior space 743 and having an open distal end, a closed proximal end, and extending along a central longitudinal axis B. The grip has a first portion 742 and a second portion 744, the second portion 744 being movable laterally relative to the first portion 742. The reservoir 750 can be formed as an ampoule having a neck portion 752 and a body portion 754. The neck portion 752 can be narrower than the body portion 754 (e.g., can have a smaller diameter). The reservoir 750 can be disposed within the interior space 743 of the grip 740. The reservoir 750 can be oriented such that the neck portion 752 is distal of the body portion 754 and therefore closer to the open end of the grip 740. The interior space 743 can be at least partially defined by an inner surface of a sidewall of the grip 740, and can be defined by a combination of the first portion 742 and the second portion 744. The grip 740 (e.g., the inner surface and/or the outer surface) can be formed as shown in FIG. 8A, having a tubular shape having two opposing flat sides coupled together by two opposing curved sides. In some embodiments, the grip 740 can have any suitable shape, such as is described above with respect to the grip 340.

The first portion 742 can include a plate 731 having a distal or bottom surface extending laterally relative to the central axis B of the grip 740. The applicator pad 710 can be disposed on a distal end of the first portion 742 (e.g., coupled to the distal surface of the plate 431). The first portion 742 can also include one or more retaining portions (not shown) (e.g., flexible tab or bump portions) extending toward the central axis B of the first portion 742 and configured to contact a shoulder of the body portion 754 of the reservoir 750 to retain the reservoir 750 in a proximal position. In some embodiments, rather than or in addition to including one or more retaining portion that contact the shoulder of the body portion 754, the first portion 742 can include retaining portions such as adhesive and/or an inner sidewall in frictional contact with the body portion 754 to retain the body portion 754 in a position in which the neck portion 752 is radially aligned with the second portion 744.

The second portion 744 can be formed as a deformable sidewall portion disposed in an opening defined by the first portion 742. The second portion 744 can optionally include a projecting portion 762 (also referred to as a release mechanism portion) extending and/or deformable laterally toward the central axis B and toward the neck portion 752 of the reservoir 750 in an initial configuration. The second portion 744 can be deformed via being pressed in by a finger of a user such that the projecting portion 762 is urged into sufficient contact with the neck portion 752 to break the neck portion 752 and release the liquid within the reservoir 750. In some embodiments, the second portion 744 can be sufficiently deformable that the second portion 744 can be urged into sufficient contact with the neck portion 752 to break the neck portion 752 such that the second portion 744 operates as the release mechanism portion without including the projecting portion 762. In some embodiments, the second portion 744 can be formed, for example, of silicone or a similar elastomeric material. Although not shown, in some embodiments, the grip 740 can include a ramp portion that can be the same or similar in structure and/or function to ramp portion 562. The ramp portion can be disposed relative to the neck portion 552 and the second portion 744 such that the second portion 744 can be deformed to urge the neck portion 552 into the ramp portion such that the neck portion 552 breaks relative to the body portion 554.

As shown in FIG. 9B, the first portion 742 can include a closed proximal end and an open distal end. The first portion 742 can optionally include a projecting portion 764 coupled to a flexible end of the first portion 742 and configured to contact a proximal end of the reservoir 750 and urge the reservoir 750 distally (or urge liquid to flow from the reservoir 750) when pressed by a user's finger.

To release liquid within the reservoir 750 such that the liquid flows to the applicator pad 710, the second portion 744 can be deformed laterally relative to the neck portion 752 (e.g., via pressing on the second portion 744 with a finger of the user such as a thumb) such that the contact between the second portion 744 and the neck portion 752 of the reservoir 750 causes the neck portion 752 to separate (e.g., break) from the body 754 of the reservoir 750 and allows liquid to flow from the reservoir 750, out of the distal end of the first portion 742, and to the applicator pad 710, resulting in the applicator pad 410 being wetted with the liquid from the reservoir 750.

The second portion 744 can include one or more grip features 745 on an exterior surface of the second portion 744 to improve the grip of the user during handling of the grip 740. The grip features 745 can include any suitable surface feature to increase grip or friction, such as one or more ridges (as shown in FIG. 8A), concave and/or convex curvatures, and/or a textured or course surface.

In some embodiments, the first portion 742 can include a filter to prevent unwanted material (e.g., particles above a certain size and/or glass pieces) from reaching the applicator pad 710. Before or after wetting the applicator pad 710 with the liquid, the distal surface of the applicator pad 710 can be disposed against a wound of the subject. The grip 740 can then be maintained against the applicator pad 710 such that the plate 731 applies distributed pressure to the applicator pad 710 for a period time, as described with respect to the method 200 above. In some embodiments, the first portion 742 and/or the second portion 744 can be deformable (e.g., squeezable) to urge the medication from the reservoir 750 (e.g., after the neck portion 752 has been separated from the body portion 750). In some embodiments, the bleeding treatment system 700 can be operated with one hand (e.g., the hand of the subject having the wound in need of treatment). For example, the user can place a thumb on the second portion 744 and wrap the remaining fingers of the same hand around the sidewall of the grip 740 (e.g., around the first portion 742). While gripping the grip 740 in this configuration, either before or after pressing the applicator pad 710 against the wound, the user can press the second portion 744 toward the neck portion 752 with the user's thumb to release liquid from the reservoir 750 as described above.

Figure 10A:
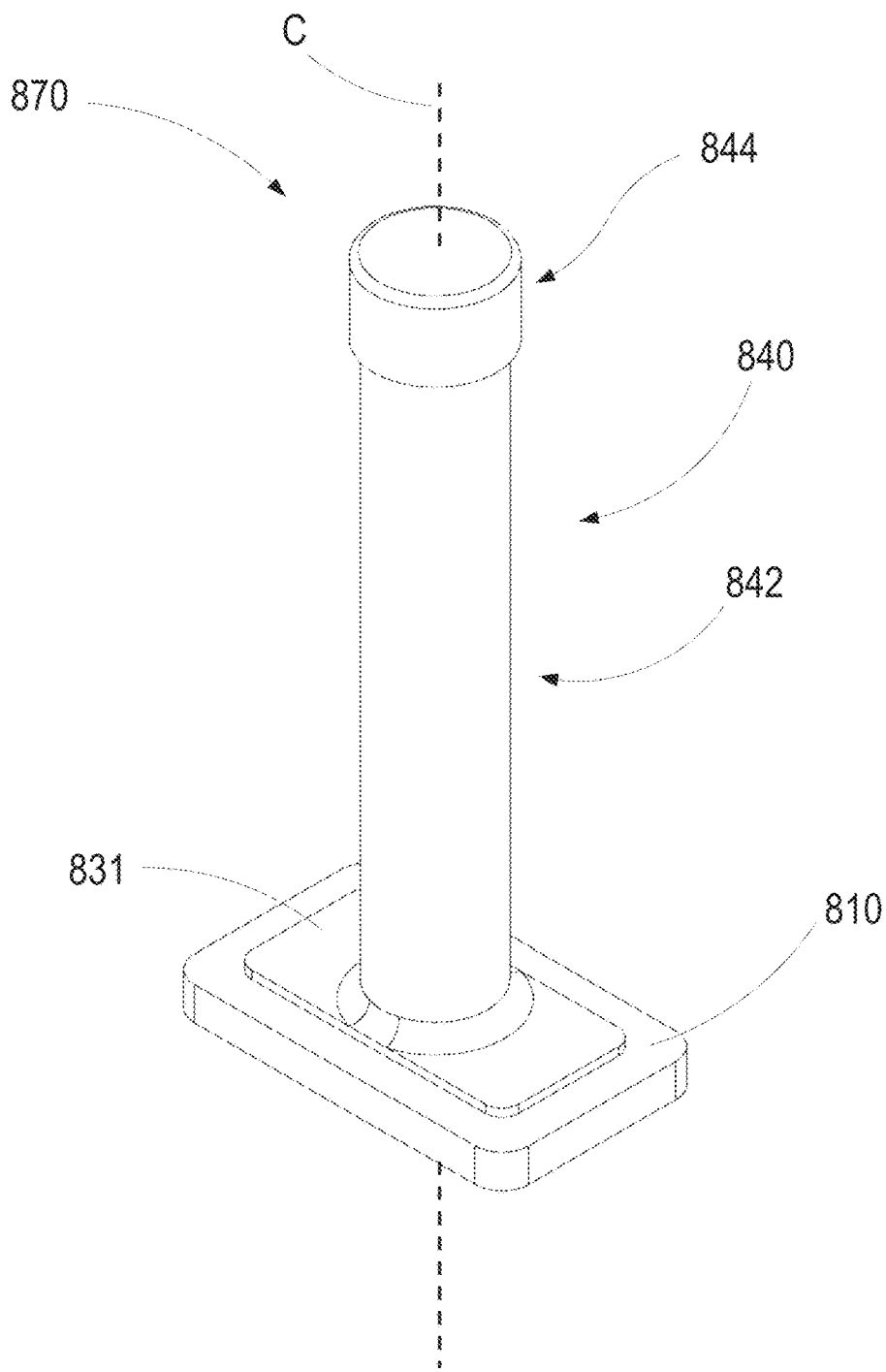
FIGS. 10A-10C are schematic illustrations of a bleeding treatment system, according to an embodiment.
Figure 10B:
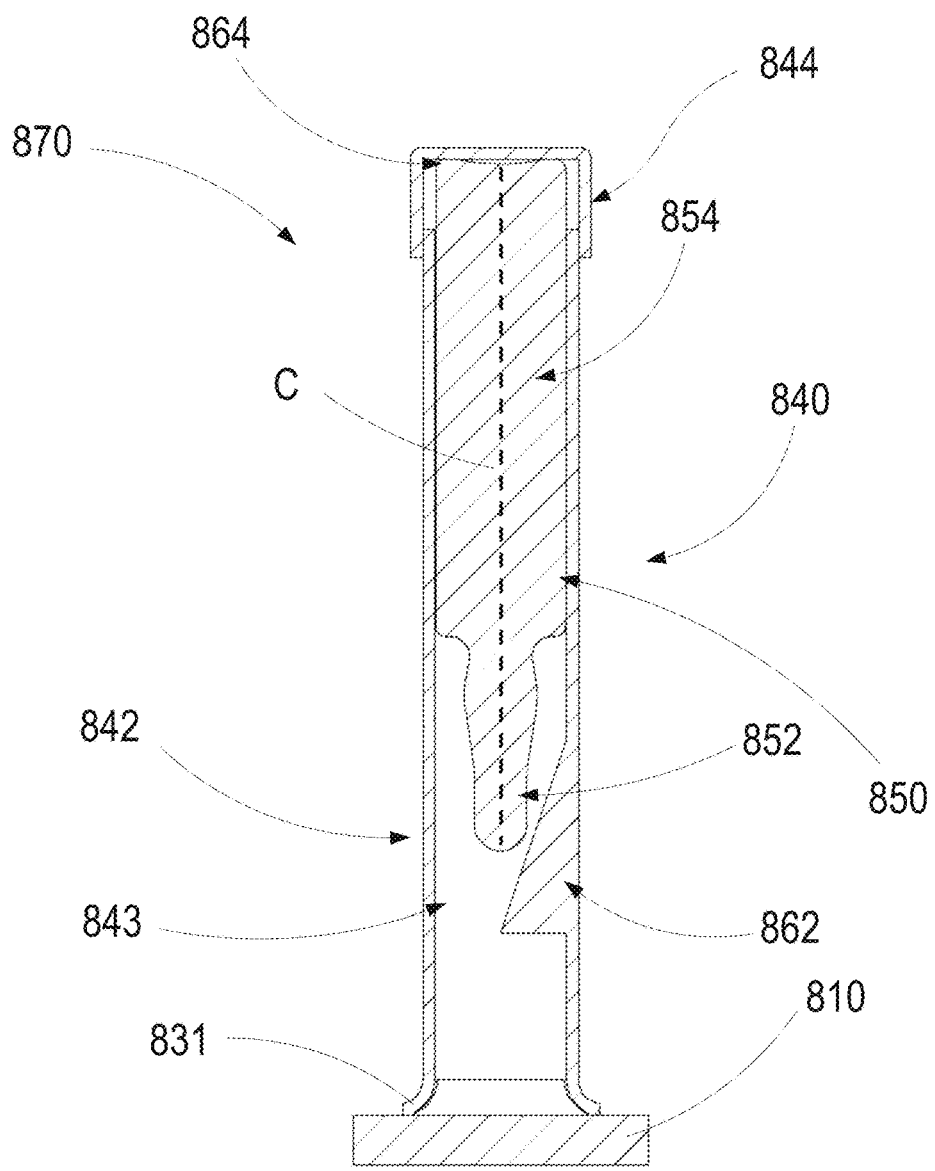
Figure 10C:
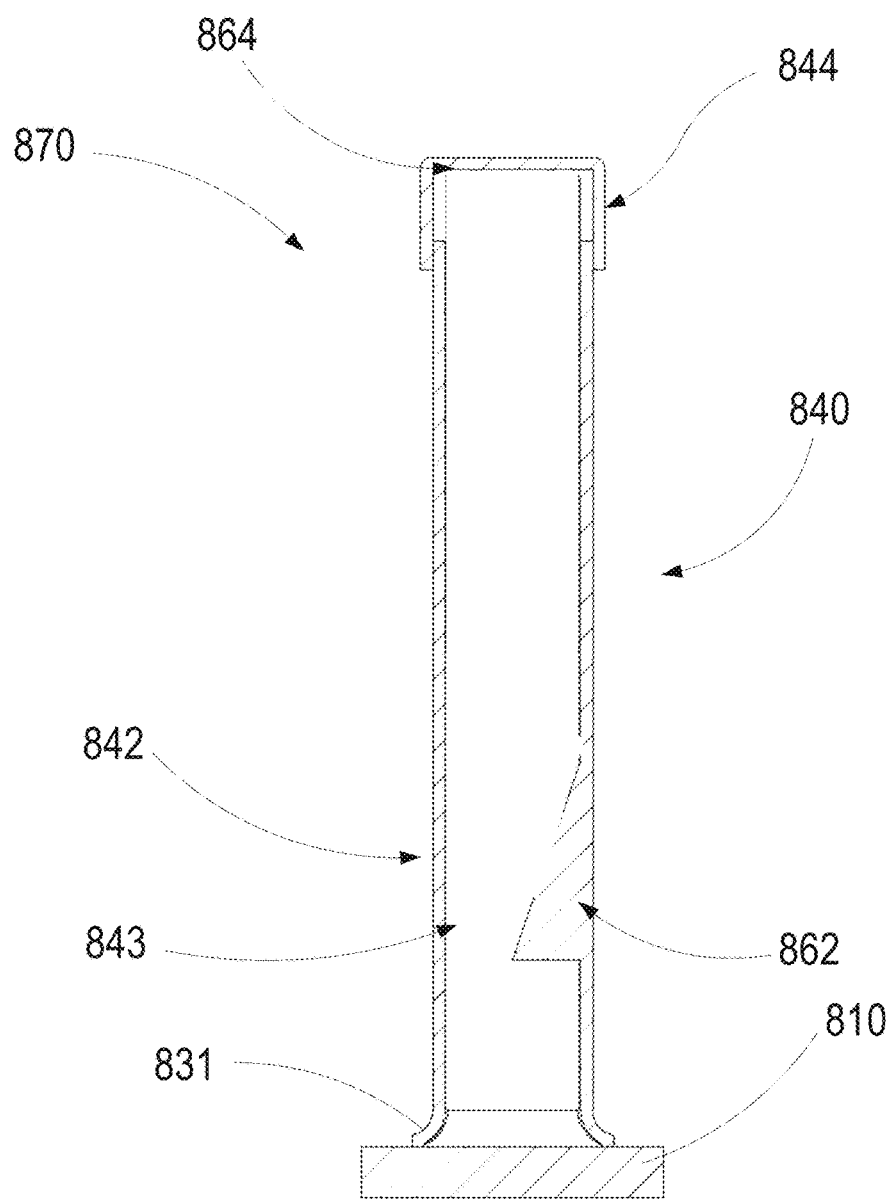

FIGS. 10A and 10B are a perspective view and a cross-sectional view of a bleeding treatment system 800. FIG. 10C is a cross-sectional view of the bleeding treatment system with a reservoir 850 of the bleeding treatment system 800 not shown. The system 800 can be the same or similar in structure and/or function to any of the delivery or treatment systems described herein. For example, the system 800 can include an applicator device 870, a reservoir 850, and an applicator pad 810. The applicator device 870 can include a grip 840 defining an interior space 843 and having an open distal end, a closed proximal end, and extending along a central longitudinal axis C. The grip has a first portion 842 and a second portion 844, the second portion 844 being movable relative to the first portion 842. The reservoir 850 can be formed as an ampoule having a neck portion 852 and a body portion 854. The neck portion 852 can be narrower than the body portion 854 (e.g., can have a smaller diameter). The reservoir 850 can be disposed within the interior space 843 of the grip 840. The reservoir 850 can be oriented such that the neck portion 852 is distal of the body portion 854 and therefore closer to the open end of the grip 840. The interior space 843 can be at least partially defined by an inner surface of a sidewall of the grip 840, and can be defined by the first portion 842 and/or the second portion 844. The grip 840 (e.g., the inner surface and/or the outer surface) can be formed as shown in FIG. 9A, having a cylindrical shape. In some embodiments, the grip 840 can have any suitable shape, such as is described above with respect to the grip 340.

The first portion 842 can include a plate 831 having a distal or bottom surface extending laterally relative to the central axis C of the grip 840. The applicator pad 810 can be disposed on a distal end of the first portion 842 (e.g., coupled to the distal surface of the plate 831). The first portion 842 can include a ramp portion 862 (also referred to as a first release mechanism portion) extending partially into the interior space 843 of the first portion 842 such that the neck portion 852 can contact the ramp portion 862. The first portion 842 can also include one or more retaining portions (not shown) (e.g., flexible tab or bump portions) extending toward the central axis C of the first portion 842 and configured to contact a shoulder of the body portion 854 of the reservoir 850 as shown in FIG. 9B to retain the reservoir 850 in an initial proximal position until sufficient force is applied to a proximal end of the reservoir 850 to advance the reservoir 850 relative to the one or more retaining portions. The first portion 842 can also include one or more grip features (not shown) on an exterior surface of a sidewall of the first portion 842 to improve the grip of the user during handling of the grip 840. The grip features can include any suitable surface feature to increase grip or friction, such as one or more ridges, concave and/or convex curvatures, and/or a textured or course surface.

The second portion 844 can include a distally-facing inner surface 864 (also referred to as a second release mechanism portion). The first portion 842 and the second portion 844 can be coupled such that the second portion 844 can be advanced relative to the first portion 842 towards a distal end of the first portion 842. For example, the first portion 842 can be coupled to the second portion 844 via any suitable coupling mechanism, such as, for example, threads or a slidable friction fit. The second portion 844 can have a larger inner diameter than an outer diameter of the proximal end of the first portion 842 such that the second portion 844 can be disposed in contact with an outer surface of the first portion 842. The reservoir 850 can be disposed in an initial position within the interior space 843 such that the proximal end of the reservoir is near or adjacent to the distally-facing inner surface 864 and can be advanced distally due to the second portion 844 being displaced distally. To release liquid within the reservoir 850 such that the liquid flows to the applicator pad 810, the second portion 844 can be advanced distally relative to the first portion 842 (e.g., via pressing on a proximal end of the second portion 844) such that the inner surface 864 applies a force to the proximal end of the reservoir 850 to urge the reservoir 850 distally such that contact between the neck portion 852 of the reservoir 850 and the ramp 862 causes the neck portion 852 to separate (e.g., break) from a remainder of the reservoir 850 (e.g., the body 854) and allows liquid to flow from the reservoir 850, out of the distal end of the first portion 842, and to the applicator pad 810, resulting in the applicator pad 810 being wetted with the liquid from the reservoir 850.

In some embodiments, the first portion 842 can include a filter to prevent unwanted material (e.g., particles above a certain size and/or glass pieces) from reaching the applicator pad 810. Before or after wetting the applicator pad 810 with the liquid, the distal surface of the applicator pad 810 can be disposed against a wound of the subject. The grip 840 can then be maintained against the applicator pad 810 such that the plate 831 applies distributed pressure to the applicator pad 810 for a period time, as described with respect to the method 200 above. In some embodiments, the first portion 842 and/or the second portion 844 can be deformable (e.g., squeezable) to urge the medication from the reservoir 850. In some embodiments, the bleeding treatment system 800 can be operated with one hand (e.g., the hand of the subject having the wound in need of treatment). For example, the user can place a thumb on the proximal end of the second portion 844 and wrap the remaining fingers of the same hand around the sidewall of the grip 840 (e.g., around the first portion 842). While gripping the grip 840 in this configuration, either before or after pressing the applicator pad 810 against the wound, the user can press the second portion 844 toward the applicator pad 810 with the user's thumb to release liquid from the reservoir 850 as described above.

Figure 11A:
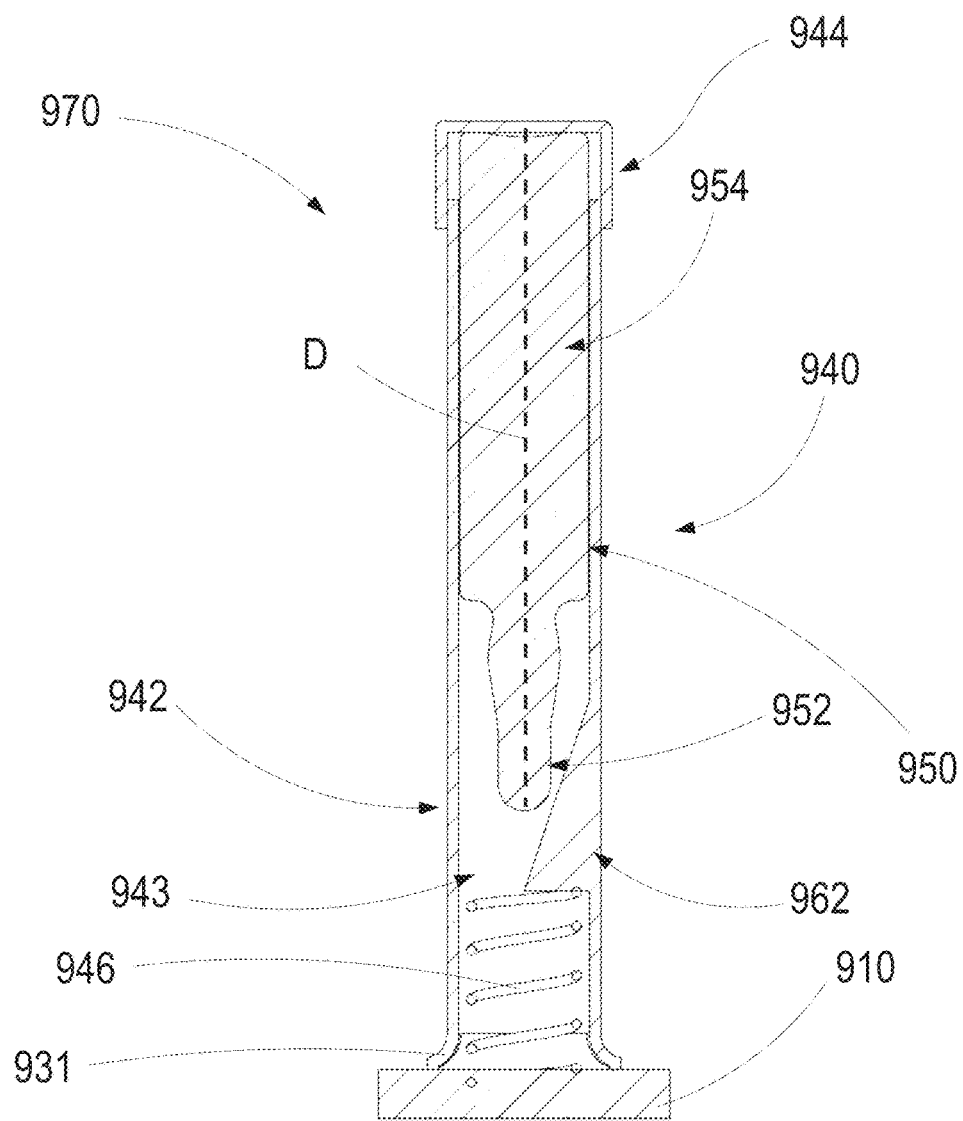
FIGS. 11A and 11B are schematic illustrations of a bleeding treatment system, according to an embodiment.
Figure 11B:
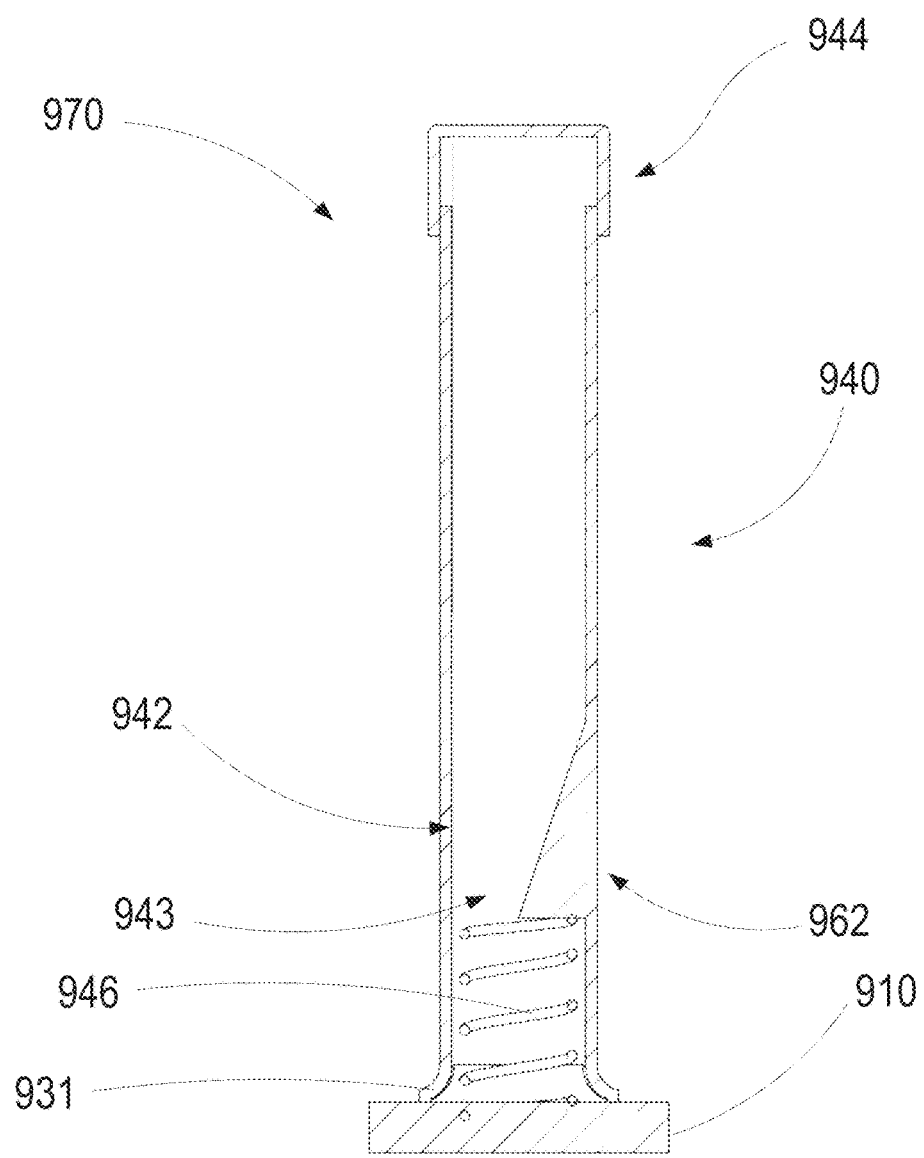

FIGS. 11A and 11B are cross-sectional views of a bleeding treatment system 900 with and without a reservoir 950 shown, respectively. The system 900 can be the same or similar in structure and/or function to any of the delivery or treatment systems described herein. For example, the system 900 can include an applicator device 970, a reservoir 950, and an applicator pad 910. The applicator device 970 can include a grip 940 defining an interior space 943 and having an open distal end, a closed proximal end, and extending along a central longitudinal axis D. The grip has a first portion 942 and a second portion 944, the second portion 944 being movable relative to the first portion 942. The reservoir 950 can be formed as an ampoule having a neck portion 952 and a body portion 954. The neck portion 952 can be narrower than the body portion 954 (e.g., can have a smaller diameter). The reservoir 950 can be disposed within the interior space 943 of the grip 940. The reservoir 950 can be oriented such that the neck portion 952 is distal of the body portion 954 and therefore closer to the open end of the grip 940. The interior space 943 can be at least partially defined by an inner surface of a sidewall of the grip 940, and can be defined by the first portion 942 and/or the second portion 944. The grip 940 (e.g., the inner surface and/or the outer surface) can be formed having a cylindrical shape. In some embodiments, the grip 940 can have any suitable shape, such as is described above with respect to the grip 340.

The first portion 942 can include a plate 931 having a distal or bottom surface extending laterally relative to the central axis D of the grip 940. The applicator pad 910 can be disposed on a distal end of the first portion 942 (e.g., coupled to the distal surface of the plate 931). The first portion 942 can include a ramp portion 962 (also referred to as a first release mechanism portion) extending partially into the interior space 943 of the first portion 942 such that the neck portion 952 can contact the ramp portion 962. The first portion 942 can also include one or more retaining portions (not shown) (e.g., flexible tab or bump portions) extending toward the central axis D of the first portion 942 and configured to contact a shoulder of the body portion 954 of the reservoir 950 to retain the reservoir 950 in an initial proximal position until sufficient force is applied to a proximal end of the reservoir 950 to advance the reservoir 950 relative to the one or more retaining portions. The first portion 942 can also include one or more grip features (not shown) on an exterior surface of a sidewall of the first portion 942 to improve the grip of the user during handling of the grip 940. The grip features can include any suitable surface feature to increase grip or friction, such as one or more ridges, concave and/or convex curvatures, and/or a textured or course surface.

The grip can include a spring portion 946. The first portion 942 and the second portion 944 can be coupled such that the second portion 944 can be advanced relative to the first portion 942 towards a distal end of the first portion 942. For example, the first portion 942 can be coupled to the second portion 944 via any suitable coupling mechanism, such as, for example, threads or a slidable friction fit. The second portion 944 can have a larger inner diameter than an outer diameter of the proximal end of the first portion 942 such that the second portion 944 can be disposed in contact with an outer surface of the first portion 942. The reservoir 950 can be disposed in an initial position within the interior space 943 such that the proximal end of the reservoir is near or adjacent the distally-facing inner surface 964 and can be advanced distally due to the second portion 944 being displaced distally. In some embodiments, the spring portion 946 can be configured to transition from an initial configuration to an expanded or compressed configuration to bring the reservoir 950 into contact with the ramp 962. For example, the spring portion 946 can be activatable to urge the ramp 962 away from the applicator pad 910 and into breaking contact with the neck portion 952. In some embodiments, the spring portion 946 may be activatable to pull or push the reservoir 950 into contact with the ramp 962. The second portion 944 can be engaged with the spring portion 946 such that depression or twisting of the second portion 944 causes the spring portion 946 to activate. Thus, to release liquid within the reservoir 950 such that the liquid flows to the applicator pad 910, the second portion 944 can be twisted or advanced distally relative to the first portion 942 (e.g., via rotating or pressing on a proximal end of the second portion 944) such that the spring portion 946 is released from an initial configuration. The spring portion 946 can then translate the reservoir 950 and/or the ramp 962 such that contact between the neck portion 952 of the reservoir 950 and the ramp 962 causes the neck portion 952 to separate (e.g., break) from a remainder of the reservoir 950 (e.g., the body 954) and allows liquid to flow from the reservoir 950, out of the distal end of the first portion 942, and to the applicator pad 910, resulting in the applicator pad 910 being wetted with the liquid from the reservoir 950.

In some embodiments, the first portion 942 can include a filter to prevent unwanted material (e.g., particles above a certain size and/or glass pieces) from reaching the applicator pad 910. Before or after wetting the applicator pad 910 with the liquid, the distal surface of the applicator pad 910 can be disposed against a wound of the subject. The grip 940 can then be maintained against the applicator pad 910 such that the plate 931 applies distributed pressure to the applicator pad 910 for a period time, as described with respect to the method 200 above. In some embodiments, the first portion 942 and/or the second portion 944 can be deformable (e.g., squeezable) to urge the medication from the reservoir 950. In some embodiments, the bleeding treatment system 900 can be operated with one hand (e.g., the hand of the subject having the wound in need of treatment). For example, the user can place a thumb on the proximal end of the second portion 944 and wrap the remaining fingers of the same hand around the sidewall of the grip 940 (e.g., around the first portion 942). While gripping the grip 940 in this configuration, either before or after pressing the applicator pad 910 against the wound, the user can press the second portion 944 toward the applicator pad 910 with the user's thumb to release liquid from the reservoir 950 as described above.

Figure 12:
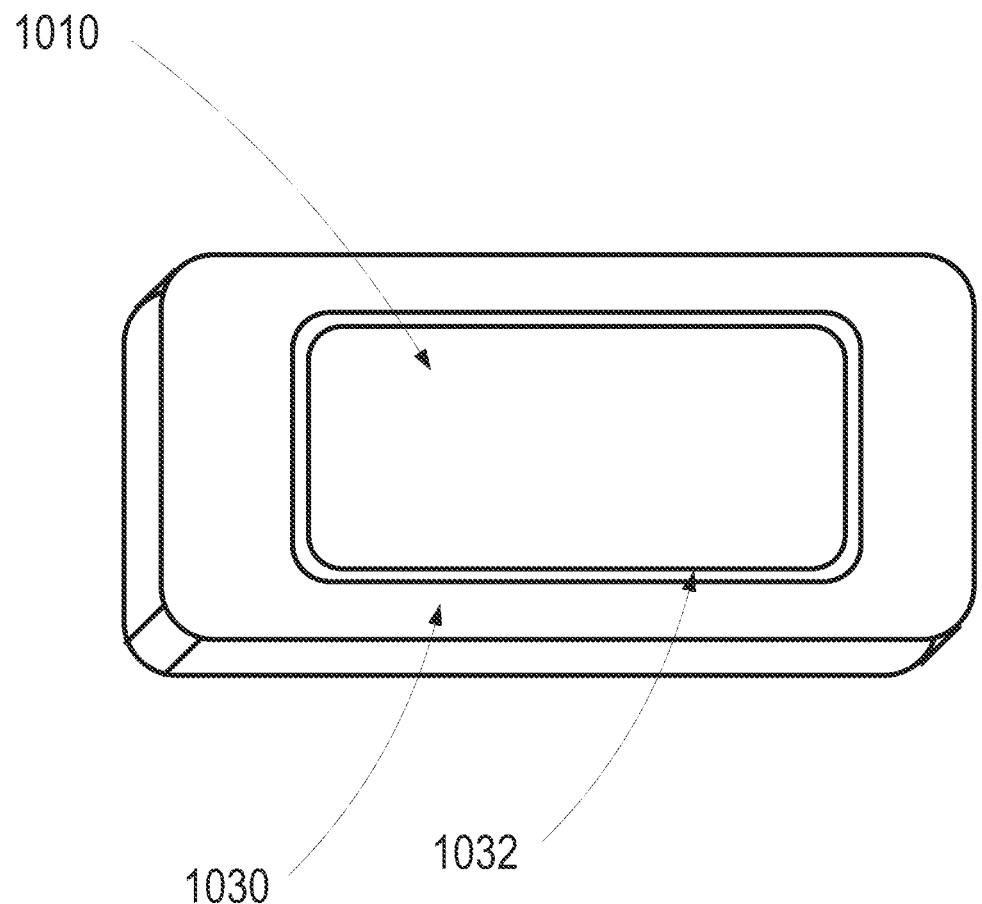
FIG. 12 is a schematic illustration of an applicator pad and a blood absorption pad, according to an embodiment.

FIG. 12 is a schematic illustration of an applicator pad 1010 in combination with a blood absorption pad 1030, which can be the same or similar in structure and/or function to any of the applicator pads and blood absorption pads, respectively, described herein. As shown, the applicator pad 1010 can be surrounded by the blood absorption pad 1030 such that the applicator pad 1010 and the absorption pad 1030 are concentric. Thus, in some embodiments, the applicator pad 1010 can be shaped, sized, and disposed (e.g., relative to a grip) such that only the applicator pad 1010 and not the blood absorption pad 1030 includes or is contacted by liquid (e.g., medication) from a reservoir. In some embodiments, a liquid impermeable divider 1032 can be disposed between the applicator pad 1010 and the blood absorption pad 1030. In some embodiments, rather than surrounding the applicator pad 1010, the blood absorption pad 1030 can only partially surround or be disposed adjacent to the applicator pad 1010. Although the applicator pad 1010 is shown as having a rectangular shape with curved edges, as described above with respect to applicator pad 110, in some embodiments the applicator pad 1010 can have any suitable shape, such as circular, ovular, or square.

Figure 13:
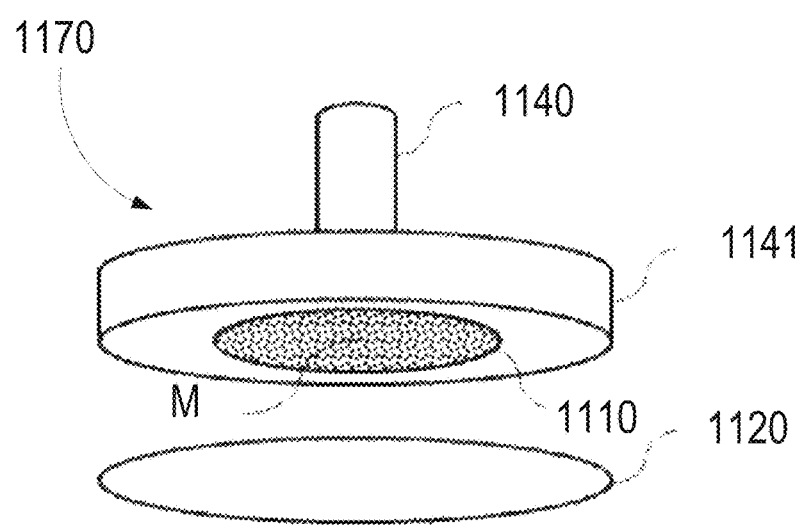
FIG. 13 is a schematic illustration of a bleeding treatment system, according to an embodiment.

In some embodiments, rather than including a reservoir within a grip of an applicator device, an applicator pad, such as any of the applicator pads described herein, can be prefilled with medication. For example, FIG. 13 is a schematic illustration of a bleeding treatment system 1100. The bleeding treatment system 1100 can be the same or similar in structure and/or function to any of the other bleeding treatment systems described herein. For example, the bleeding treatment system 1100 can include an applicator device 1170 having a grip 1140, an applicator pad 1110 (also referred to as a topical applicator pad), and an applicator seal 1120. In some embodiments, the applicator pad 1110 can be a porous applicator (e.g., a sponge type material) configured to retain liquid medication M and only apply the liquid medication M to a wound site on physical contact. The applicator pad 1110 can be prefilled (e.g., presoaked) with liquid or dry medication M. The grip 1140 can include a plate 1141 having a diameter equal to or larger than the applicator pad 1110 such that the grip 1140 can be used to apply distributed pressure to the applicator pad 1110 when the applicator pad 1110 is in contact with a wound. The plate 1141 can be rigid or semi-rigid or have a surface opposite the surface contacting the applicator pad 1110 that is rigid or semi-rigid to apply uniform pressure to the applicator pad 1110. In some embodiments, the plate 1141 can be flexible. The plate 1141 can function as an insulating mechanism configured to isolate a hand applying pressure from the wound site and the medication in the applicator pad 1110. To use the system 1100, the applicator seal 1120 can be removed from the applicator pad 1110 and the grip 1110 can be used to apply the applicator pad 1110 to a wound such that the medication flows to the wound and to maintain pressure against the wound by applying pressure to the applicator pad 1110.

Figure 14:
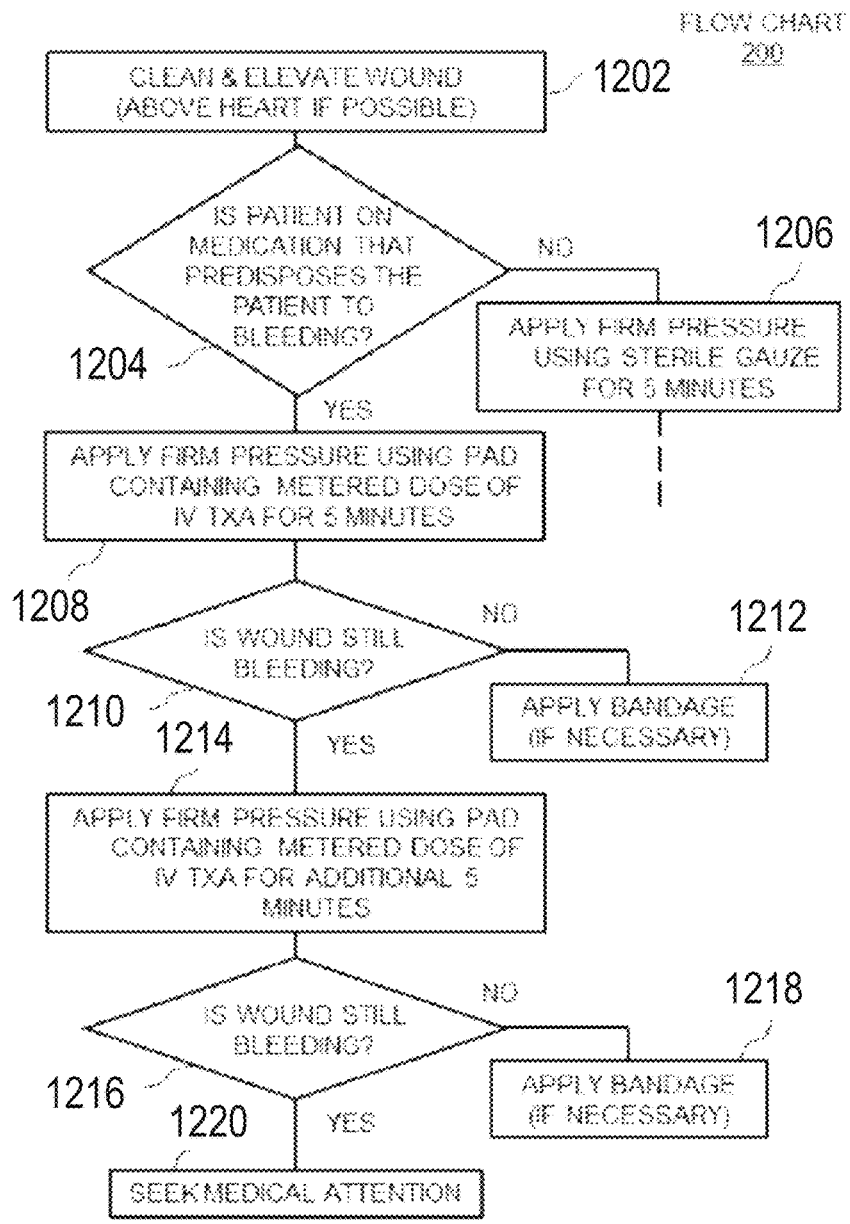
FIG. 14 is a flow chart of a method of using a bleeding treatment system, according to an embodiment.

FIG. 14 is a flow chart of a method 1200 of using a bleeding treatment system, such as any of the bleeding treatment systems described herein. The method 1200 can be for reducing bleeding at a wound site of a subject taking a medication that predisposes the subject to increased and/or prolonged bleeding. In some embodiments, the steps of method 1200 can be implemented by the subject, a caregiver, a healthcare provider, a veterinary care provider, etc. In step 1202, the wound can be cleaned and elevated (e.g., by the subject having the wound and/or by a caregiver or clinician) to reduce bleeding. In some embodiments, the wound is cleaned (e.g., with soap and water). In some embodiments, the wound is elevated above the level of the heart of the patient.

In step 1204, whether the subject (e.g., a patient) is on a medication (e.g., an anticoagulant drug or antiplatelet drug) that predisposes the subject to increased and/or prolonged bleeding can be determined. For example, a caregiver or clinician can check to see if such a medication has been taken by the subject within a relevant time period (e.g., by checking a medical record or asking the subject). In some embodiments, step 1204 can be not included and a user can proceed directly to step 1206 described below. In some embodiments, step 1204 can be performed after step 1206 if the wound is still bleeding, and the steps of the method 1200 can proceed from there.

In step 1206, if the subject is determined not to have taken a medication that predisposes the subject to increased and/or prolonged bleeding within a relevant time period, the firm pressure can be applied to the wound using a sterile gauze pad (e.g., by the subject or a caregiver). In some embodiments, the firm pressure can be applied for a first period of time (e.g., a predetermined period of time). In some embodiments, for example, the first period of time can be about five minutes, between about four minutes and about six minutes, less than about four minutes, greater than about five minutes, greater than about six minutes. After the first period of time, the pressure can be removed. If the wound is no longer bleeding, the subject or a caregiver can apply a bandage to the wound. If the wound is still bleeding, then step 1208 can be performed as described below and/or medical attention may be sought.

In step 1208, if the subject is determined to have taken a medication that predisposes the subject to increased and/or prolonged bleeding within a relevant time period, or if applying firm pressure for the first period of time as described in step 1206 has not caused bleeding to stop, firm pressure can be applied to the wound using a topical applicator pad containing a metered dose of medication (e.g., TXA such as intravenous (IV) TXA) for a second period of time (e.g., a second predetermined period of time) (e.g., five minutes) such that the medication contacts the wound. In some embodiments, the second period of time can be greater than the first period of time. In some embodiments, the second period of time can be less than the first period of time. In some embodiments, the metered dose can be between three and ten mL and/or include between about 300 and about 1000 mg of medication.

In step 1210, the pressure can be removed by the subject or a caregiver (e.g., via removing the applicator pad) and the wound can be checked to see if the wound is still bleeding. In step 1212, if the wound is no longer bleeding, a bandage can be applied to the wound by the subject or a caregiver. In step 1214, if the wound is still bleeding, the subject or a caregiver can reapply firm pressure to the wound using the topical applicator pad for an additional predetermined time period (e.g., for an additional five minutes). In some embodiments, a new topical applicator pad (containing a metered dose or not containing a metered dose of medication) may be used. In step 1216, the pressure can be removed and checked to see if the wound is still bleeding. In step 1218, if the wound is no longer bleeding, a bandage can be applied to the wound if needed. In step 1220, if the wound is still bleeding, the subject can seek medical attention (with the help of a caregiver if needed).

Figure 15A:
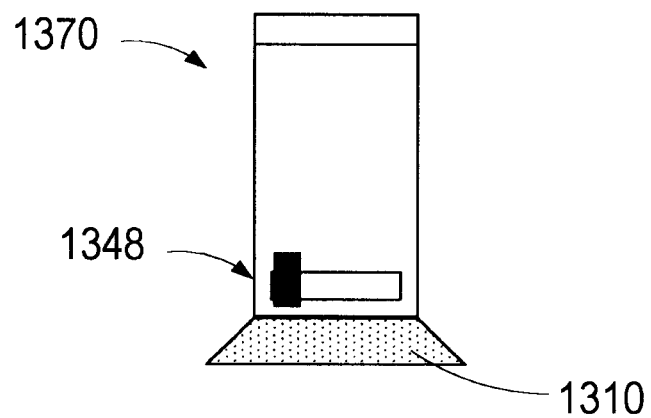
FIGS. 15A-15E are schematic illustrations of a bleeding treatment system in various stages of use, according to an embodiment.
Figure 15B:
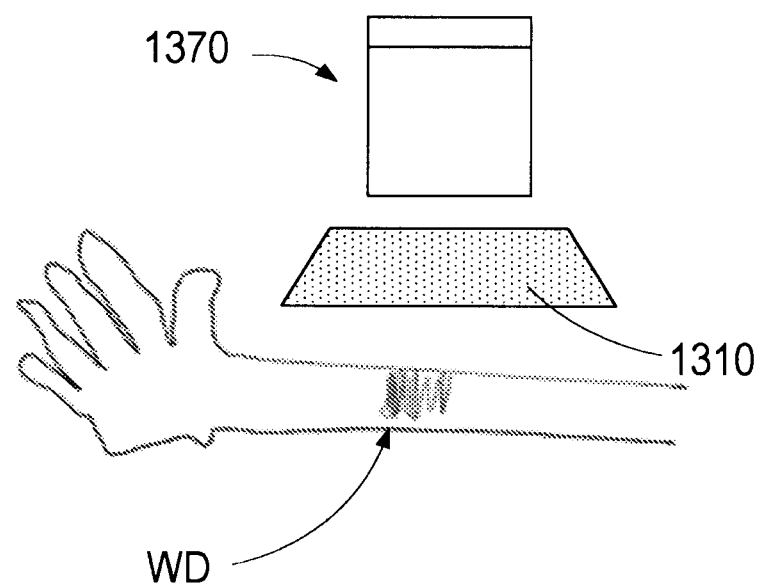
Figure 15C:
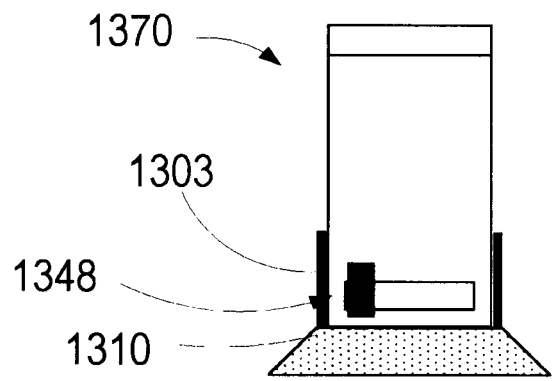

FIGS. 15A-15E are schematic illustrations of a bleeding treatment system 1300 in various stages of use. The system 1300 can be the same or similar in structure and/or function to any of the systems described herein. For example, the system 1300 can include an applicator device 1370, a reservoir (not shown), and an applicator pad 1310. As shown in FIG. 15A, the applicator pad 1310 can be coupled to the applicator device 1370 via a pad connector 1348. The pad connector 1348 can include any suitable coupling mechanism, such as any of the coupling mechanisms and pad connector described herein. For example, the applicator device 1370 can include a sliding mechanism or a latch disengageable with an engagement feature associated with the applicator pad 1310 such that the engagement feature associated with the applicator pad 1310 can be released from the applicator device 1370 before or after being applied to a wound WD, as shown in FIG. 15B.

Figure 15D:
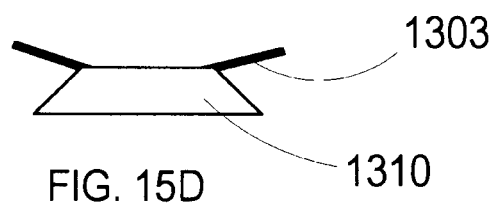
Figure 15E:
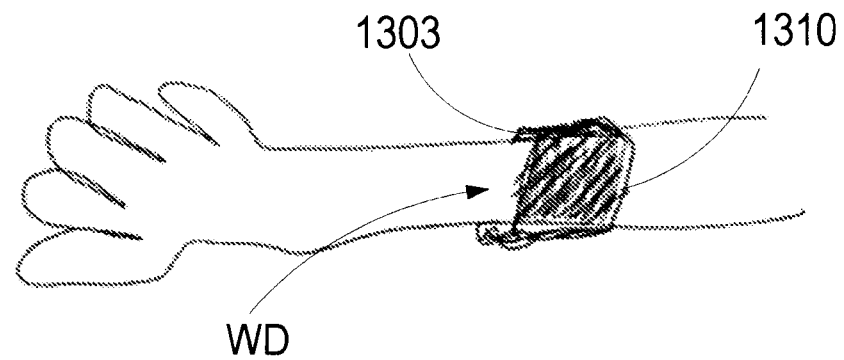

In some embodiments, the applicator pad 1310 can be coupled to the applicator device 1370 via adhesive strips 1303 that are releasable from the applicator device 1370 via, for example, the pad connector 1348 which can operate as a release mechanism to allow the adhesive strips 1303 to contact skin of a patient to secure the pad connector 1348 to a wound WD. Thus, in the first configuration shown in FIG. 15C, the applicator pad 1310 can be coupled to the applicator device 1370. As shown in FIG. 15D, the applicator pad 1310 and the adhesive strips 1303 can be decoupled from the applicator device 1370. The applicator pad 1310 can then be secured to the subject at the location of the wound via the adhesive strips 1303.

Figure 16D:
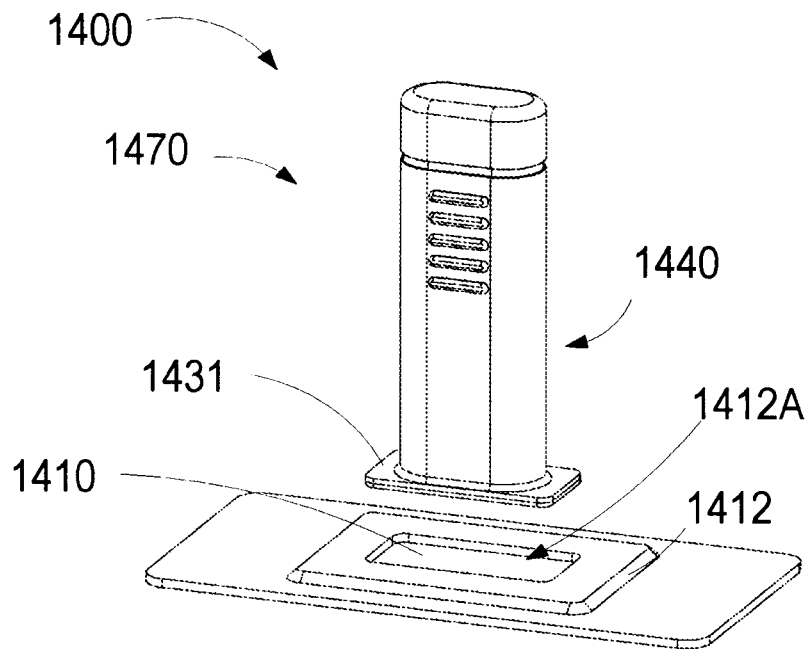
FIGS. 16D-16F are schematic illustrations of the bleeding treatment system of FIGS. 16A-16C in a separated configuration.
Figure 16E:
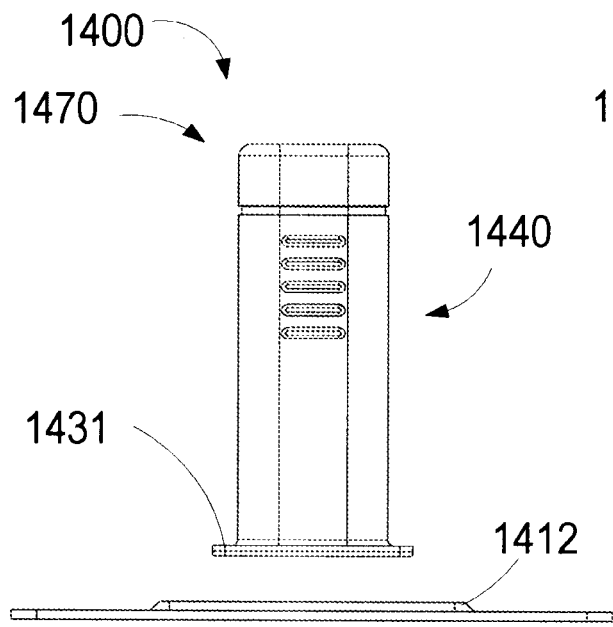
Figure 16F:
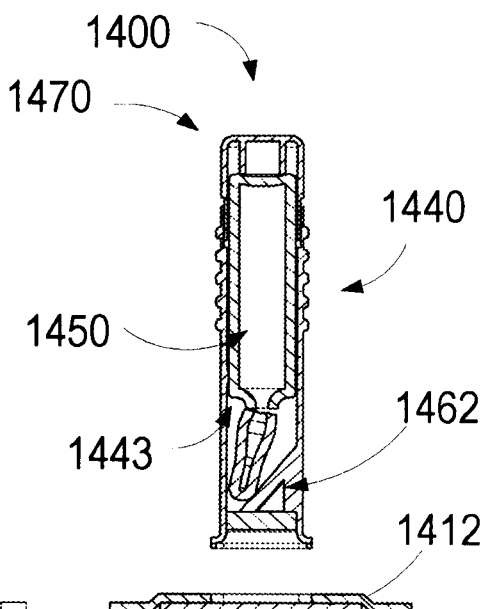

FIGS. 16A-16C are schematic illustrations of a perspective, front, and cross-sectional view, respectively, of a bleeding treatment system 1400 in wetting configuration in which a reservoir 1450 has been broken to release the contents of the reservoir 1450. FIGS. 16D-16F are schematic illustrations of a perspective, front, and cross-sectional view, respectively, of the bleeding treatment system 1400 in a separated configuration in which a grip 1440 of the system 1400 has been decoupled from an applicator pad 1410. The system 1400 can be the same or similar in structure and/or function to any of the delivery or treatment systems described herein, such as, for example, the bleeding treatment system 500. For example, the system 1400 includes an applicator device 1470, the reservoir 1450, and the applicator pad 1410. The applicator device 1470 includes a grip 1440 defining an interior space 1443 and having an open distal end, a closed proximal end, and extending along a central longitudinal axis. The applicator device 1470 includes a filter 1471 (e.g., disposed between a ramp 1462 of the grip 1440 and the distal opening of the grip 1440) to prevent unwanted material (e.g., particles above a certain size and/or glass pieces) from reaching the applicator pad 1410.

As shown in FIGS. 16A-16F, the system 1400 can include a bandage 1412 coupled to a portion of an upper surface of the applicator pad 1410 and extending beyond an outer perimeter of the applicator pad 1410. Although shown as surrounding a periphery of the applicator pad 1410, in some embodiments the bandage can extend beyond opposing portions or sides of the applicator pad 1410 but not in all directions. The bandage 1412 can define one or more openings 1412A adjacent the upper surface of the applicator pad 1450 such that fluid can flow through the openings and into wetting contact with the applicator pad 1450. In some embodiments, the one or more openings 1412A can collectively have a surface area and perimeter equal to or smaller than the surface area and perimeter of the distal opening of the grip 1440. In some embodiments, the bandage 1412 can include a liquid permeable layer or portion covering the one or more openings 1412A. In some embodiments, the bandage 1412 can be adhesively coupled to the upper surface of the applicator pad 1450 via one or more adhesive portions.

The system 1400 can be placed on a surface of a subject with the applicator pad 1410 and the bandage 1412 in contact with the surface, the applicator pad 1410 contacting a wound of the subject and the bandage 1412 surrounding the applicator pad 1410. The applicator device 1470 can be transitioned from an initial configuration to the wetting configuration shown in FIGS. 16A-16C via the same steps as described with respect to the system 500. After the contents of the reservoir 1450 are released from the reservoir 1450 as shown in FIG. 16C, the contents can flow through the filter 1471, through the one or more openings 1412A in the bandage 1412, to the applicator pad 1410, and into contact with the wound. The grip 1440 can be used to apply pressure to the applicator pad 1410 and thus the wound (e.g., before and/or after wetting the applicator pad 1410) by applying a downward pressure to the grip 1440 with the distal end of the grip 1440 and/or the plate 1431 contacting the applicator pad 1410.

In some embodiments, the applicator pad 1410 and the bandage 1412 can be left on the skin of the subject such that the applicator pad 1410 remains in contact with the wound, and the grip 1440 can be decoupled from the applicator pad 1410 and the bandage 1412 such that the applicator pad 1410 is not displaced relative to the wound during the decoupling. As shown in FIGS. 16D-16F, after decoupling the grip 1440 from the applicator pad 1410 and/or the bandage 1412, the grip 1440 can be discarded, leaving the applicator pad 1410 and the bandage 1412 in place on the wound and skin of the subject.

Figure 17A:
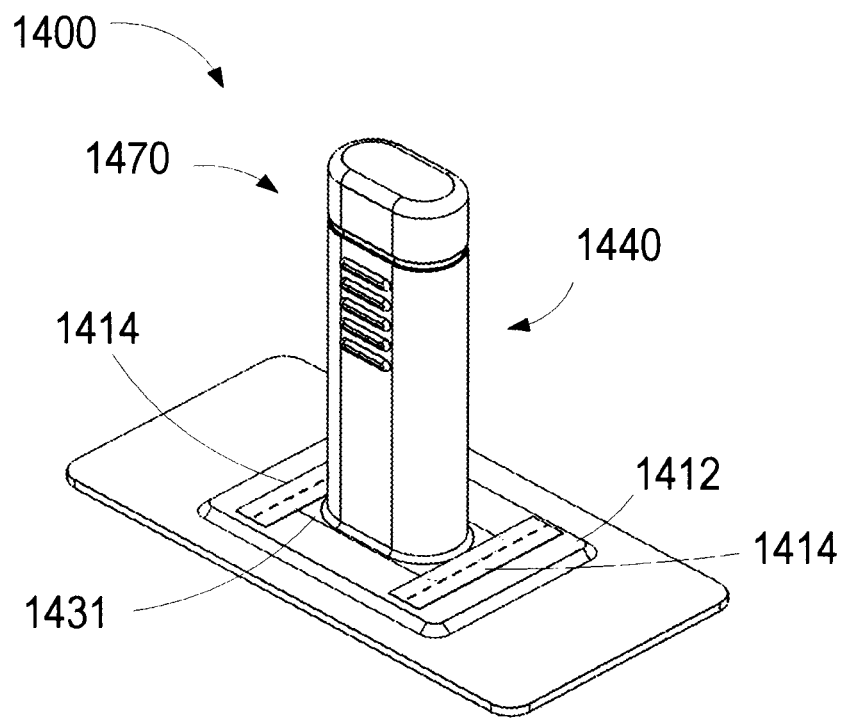
FIGS. 17A and 17B are schematic illustrations of the bleeding treatment system of FIGS. 16A-16C, according to an embodiment.
Figure 17B:
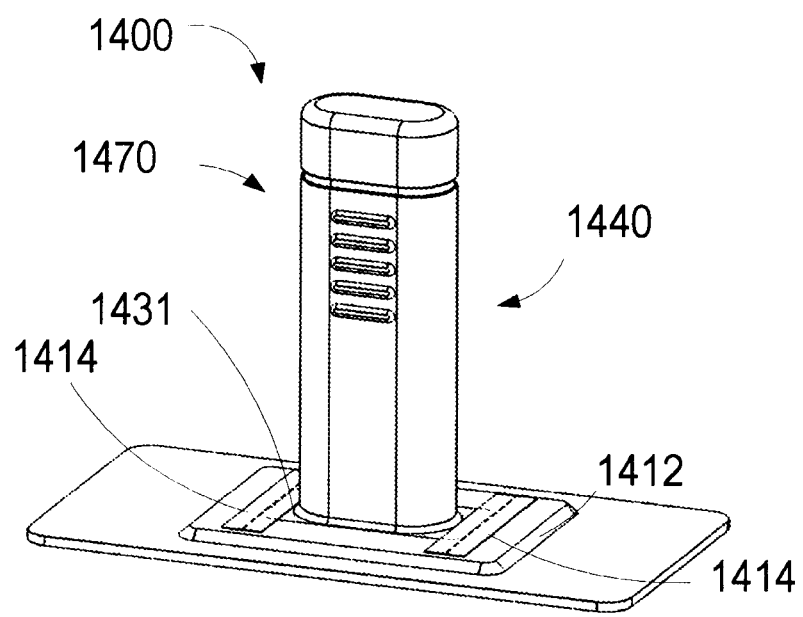

The grip 1440 can be coupled to and/or decoupled from the applicator pad 1410 and/or the bandage 1412 via any suitable decoupling method described herein. For example, as shown in FIGS. 17A and 17B, which are two different perspective views of the system 1400 including two adhesive strips 1414 (also referred to as pad connectors), the applicator device 1470 can be coupled to the bandage 1412 via removable adhesive strips 1414. The adhesive strips 1414 can be disposed in contact with an upper surface of the plate 1431 on either side of the grip 1440 and can each have ends in contact with the bandage 1412 such that the adhesive strips 1414 secure the grip 1440 to the bandage 1412 via the plate 1431. In some embodiments, the adhesive strips 1414 can be flexible but have low or no elasticity. To separate the grip 1440 from the bandage 1412 and the applicator pad 1410, each of the adhesive strips 1414 can be peeled away from the bandage 1412 to release the bandage 1412 from the plate 1431.

Figure 18:
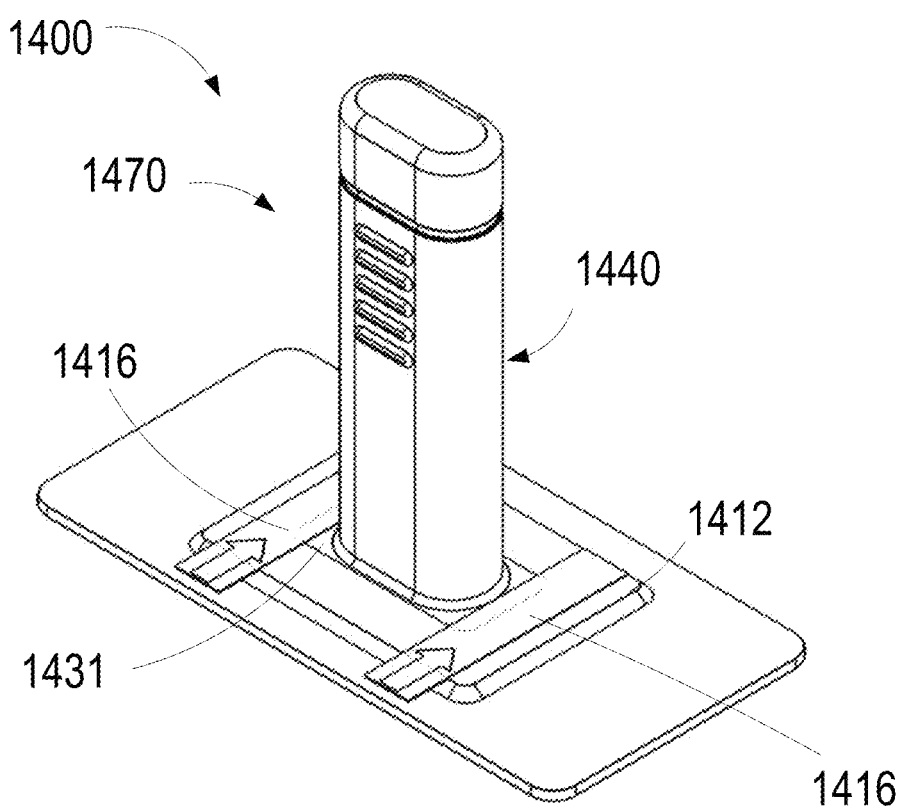
FIG. 18 is a schematic illustration of a bleeding treatment system of FIGS. 17A-17B, according to an embodiment.

In some embodiments, as shown in FIG. 18, rather than including adhesive strips that are peelable and have low or no elasticity, the system 1400 can include adhesive strips 1416 that have high elasticity and can be decoupled from the bandage 1412 and/or the plate 1431 via stretching a free end of each of the adhesive strips 1416 away from but within or near a plane containing the portion of the adhesive strip 1416 (also referred to as pad connectors) adhesively coupled to the bandage 1412 and/or the plate 1431 such that the adhesive strip 1416 is deformed and the adhesive contact between the adhesive strip 1416 and the bandage 1412 and/or the plate 1431 is broken. For example, the adhesive strips 1416 can include a synthetic rubber resin adhesive.

Figure 19A:
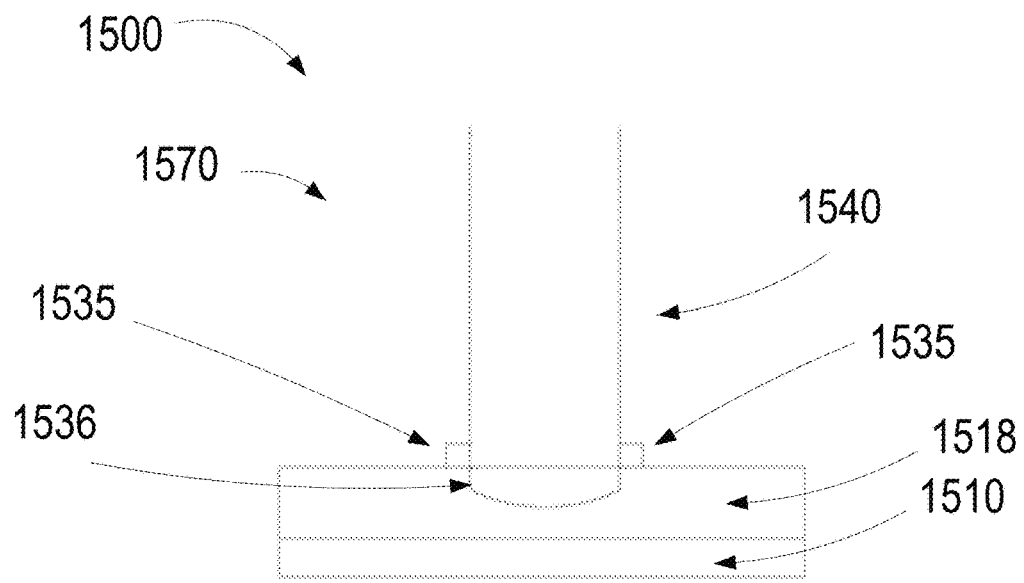
FIG. 19A is a schematic illustration of a bleeding treatment system, according to an embodiment.
Figure 19B:
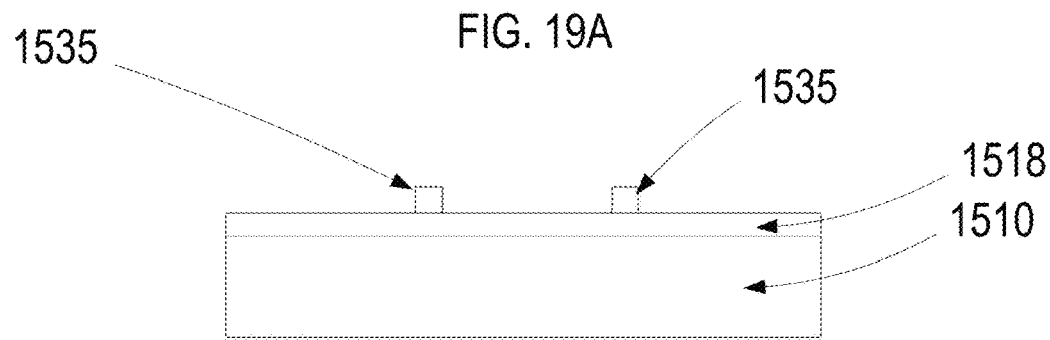
FIG. 19B is a schematic illustration of a portion of the bleeding treatment system of FIG. 19A.

In some embodiments, an applicator pad can include or be coupled to a rigid or semi-rigid backing portion that is configured to be releasably engaged by a portion of an applicator device. For example, FIG. 19A is a schematic illustration of a system 1500 that can be the same or similar in structure and/or function to any of the other systems described herein. The system 1500 can include an applicator device 1570 including a grip 1540, an applicator pad 1510, and a reservoir (not identified) that is included within the applicator pad 1510 and/or within the grip 1540. As shown in FIG. 19B, the applicator pad 1510 can be coupled (e.g., via adhesive) to a backing portion 1518 that can be rigid or more rigid than the applicator pad 1510. The backing portion 1518 can define one or more openings (not shown in FIGS. 19A and 19B) such that fluid can flow from the reservoir within the grip 1540 to the applicator pad 1510 to wet the applicator pad 1510. The backing portion 1518 can include one or more pad retainer portions 1535 configured to be received by or otherwise coupled to complementary pad retainer portions (not shown) of the grip 1540 such that the grip 1540 can be adhered, clipped, latched, frictionally fit, hook-and-loop fastened, buttoned, or otherwise releasably coupled via any suitable coupling mechanism to the backing portion 1518. After applying pressure to the backing portion 1518 to push the applicator pad 1510 against the wound, the grip 1540 can be decoupled from the backing portion 1518 by uncoupling the complementary pad retainer portions. As shown in FIG. 19A, the grip 1540 can include a convex distal surface 1536 configured to apply targeted and increased pressure to the wound when a user presses the grip 1540 into the applicator pad 1510 coupled to the wound. The convex distal surface 1536 can include one or more openings to allow fluid flow through the convex distal surface 1536.

Figure 19C:
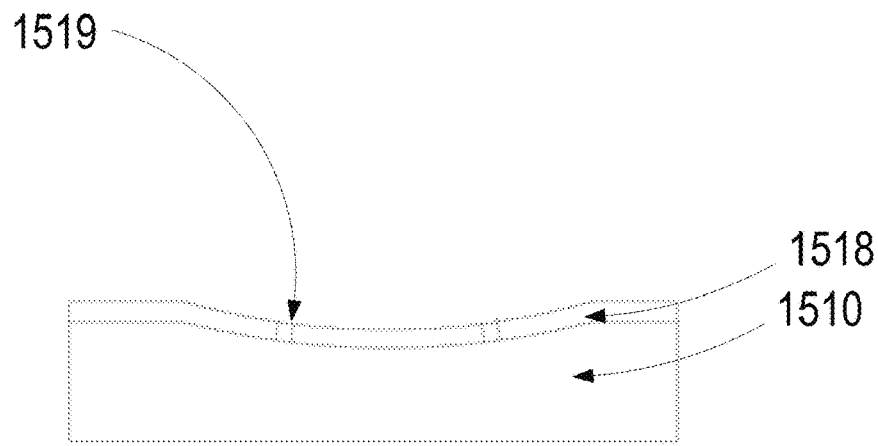
FIG. 19C is a schematic illustration of a portion of the bleeding treatment system of FIG. 19A, according to an embodiment.

As shown in FIG. 19C, in some embodiments, the backing portion 1518 can be curved and rigid such that the convex distal surface 1536 of the grip 1540 can be seated in a concave upper surface of the backing portion 1518 during wetting of the applicator pad 1510 and/or during application of pressure to the applicator pad 1510 and, thus, the wound. As shown in FIG. 19C, the backing portion 1518 can define one or more openings 1519 such that fluid can flow from the reservoir within the grip 1540 to the applicator pad 1510 to wet the applicator pad 1510.

Figure 20:
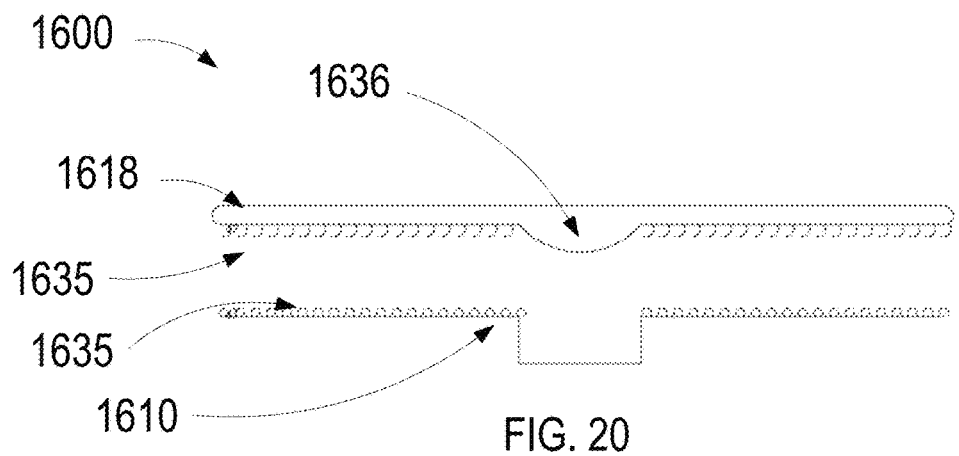
FIG. 20 is a schematic illustration of a bleeding treatment system, according to an embodiment.

As shown in FIG. 20, which is a schematic illustration of a system 1600, in some embodiments a backing portion 1618 can be releasably coupled to an applicator pad 1610 via an attachment such as a hook-and-loop fastener 1635 (e.g., Velcro®) or releasable adhesive (not shown). The backing portion 1618 can include a convex distal surface 1636 configured to apply pressure to the portion of the applicator pad 1610 in contact with a wound when the applicator pad 1610 contacts a wound and the backing portion 1618 is coupled to the applicator pad 1610. After hemostasis occurs, the backing portion 1618 can be removed from the applicator pad 1610, leaving the applicator pad 1610 in place relative to the wound.

Figure 21:
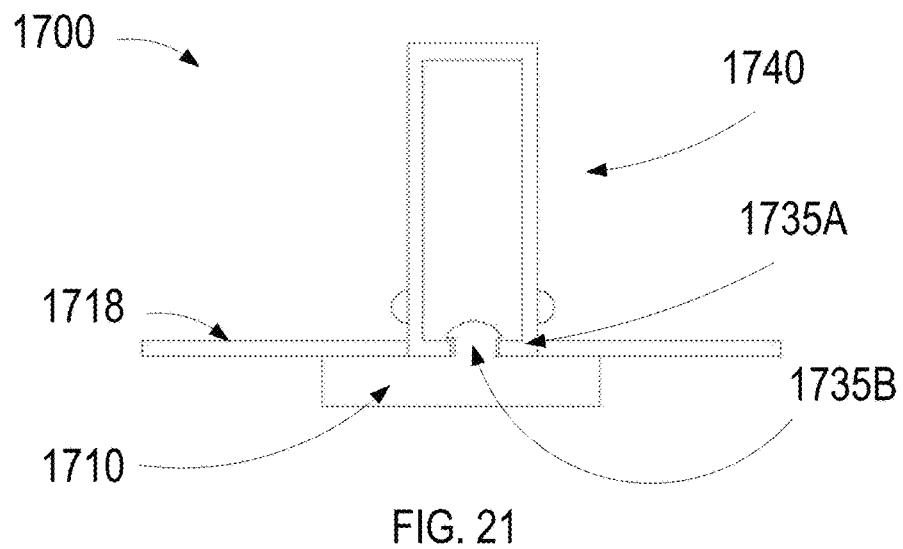
FIG. 21 is a schematic illustration of a bleeding treatment system, according to an embodiment.

FIG. 21 is a schematic illustration of a system 1700. The system 1700 can be the same or similar in structure and/or function to any of the systems described herein. For example, the system 1700 includes a grip 1740 and an applicator pad 1710. The applicator pad 1710 can be coupled to a backing portion 1718 that may be configured as a bandage. The backing portion 1718 can include an adhesive covered by a peel-away adhesive liner disposed on a distal surface of the backing portion. The adhesive liner can be peeled away prior to placing the backing portion 1718 on a subject's skin so that the backing portion 1718 can be adhered to the skin via the adhesive. In some embodiments, the backing portion 1718 can extend laterally from the grip 1740 prior to disposal on the skin as shown in FIG. 21. In some embodiments, the backing portion 1718 can be flush with the grip 1740 (e.g., extending upward along the sidewall of the grip 1740) and then folded down to adhere to the skin. In some embodiments, the backing portion 1718 can fully surround and/or extend circumferentially away from the applicator pad 1710. In some embodiments, the backing portion 1718 can extend along one axis of the applicator pad 1710.

The backing portion 1718 and/or the applicator pad 1710 can include or be coupled to a pad retainer portion 1735B extending away from the applicator pad 1710 and configured to be releasably grasped by a pad retainer portion 1735A of the grip 1740. The pad retainer portion 1735A of the grip 1740 can include, for example, flexible arms configured to engage with a recess of the pad retainer portion 1735B such that the grip 1740 and the applicator pad 1710 are coupled (e.g., during wetting and/or applying pressure to the wound). To separate the grip 1740 from the applicator pad 1710, the flexible arms can be pulled away from the recess of the pad retainer portion 1735B (e.g., via pulling on tabs extending from an outer surface of the grip 1740 or by squeezing engagement mechanisms (e.g., semicircular buttons) near or adjacent to the distal end of the grip 1740 to activate a release mechanism such that the pad retainer portion 1735B is released) and the grip 1740 can be removed from the pad retainer portion 1735B.

Figure 22A:
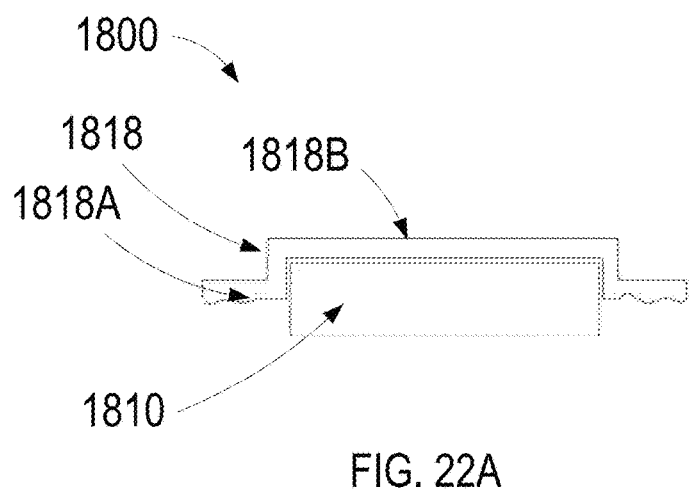
FIGS. 22A and 22B are schematic illustrations of cross-sectional and top views of a bleeding treatment system, according to an embodiment.
Figure 22B:
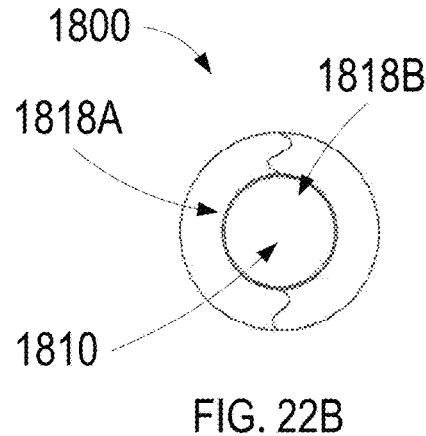

FIGS. 22A and 22B are cross-sectional and top views of a schematic illustration of a system 1800. The system 1800 can be the same or similar in structure and/or function to any of the systems described herein. For example, the system 1800 includes a semi-rigid backing portion 1818 that may be configured as a bandage and an applicator pad 1810. As shown, the semi-rigid backing portion 1818 can include a foam ring 1818A surrounding the applicator pad 1810 and a backing layer 1818B disposed against the upper surface of the applicator pad 1810 and coupled to the foam ring 1818A. The foam ring 1818A can adhesively couple the backing portion 1818 and the applicator pad 1810 to the surface of the skin of the subject and apply compressive pressure to the applicator pad 1810 to urge the applicator pad 1810 against a wound. In some embodiments, the pressure applied to the applicator pad 1810 can activated release of medication(s) from the applicator pad 1810.

Figure 23A:
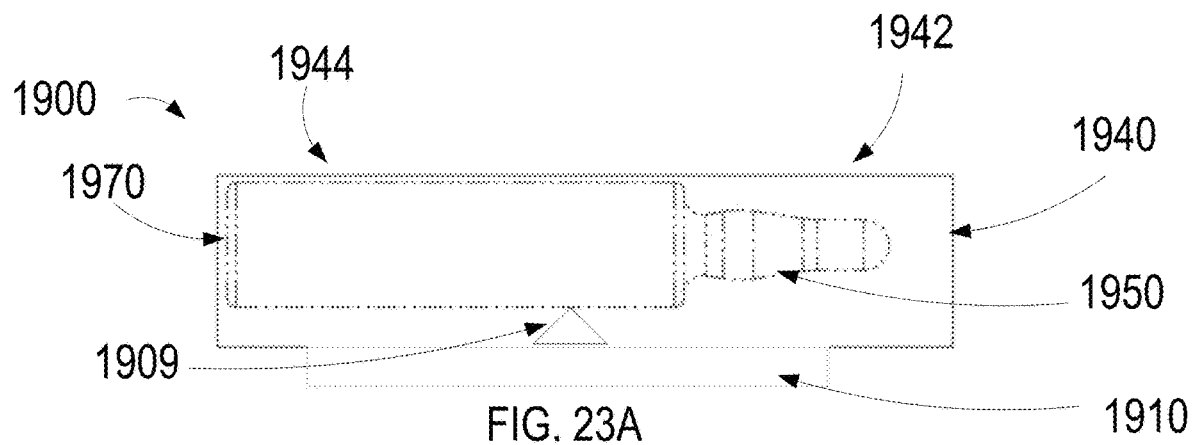
FIGS. 23A-C are schematic illustrations of a bleeding treatment system, according to an embodiment.
Figure 23B:
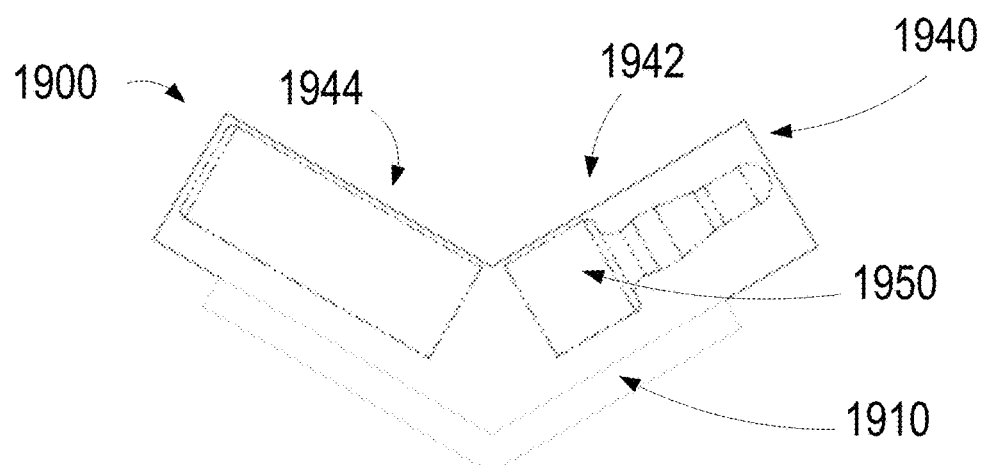
Figure 23C:
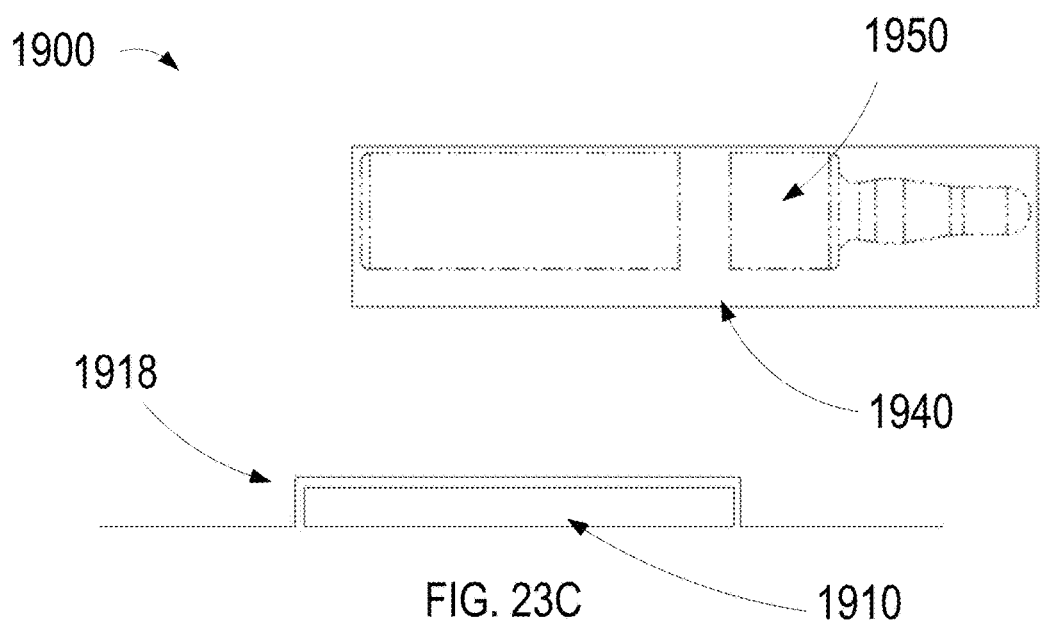

In some embodiments, the contents of a reservoir can be configured to flow from the reservoir to an applicator pad through a sidewall of a grip containing the reservoir. For example, FIGS. 23A-23C are schematic illustrations of a system 1900 in various stages of operation. The system 1900 can be the same or similar in structure and/or function to any of the systems described herein. For example, the system 1900 includes an applicator device 1970, a reservoir 1950, and an applicator pad 1910. The applicator device 1970 can include a grip 1940 defining an interior space within which the reservoir 1950 can be disposed. As shown, the grip 1940 can be disposed horizontally such that the applicator pad 1910 is coupled to a sidewall of the grip 1940 and the grip 1940 and/or the reservoir 1950 are elongated along a longitudinal axis disposed substantially parallel to the applicator pad 1910 in the initial configuration shown in FIG. 23A.

The grip 1940 can include a first portion 1942 and a second portion 1944 collectively defining the interior space within which the reservoir 1950 is disposed. The first portion 1942 can be configured to be bent relative to the second portion 1944 as shown in FIG. 23B to cause the reservoir 1950 to break and the contents of the reservoir 1950 to flow from the reservoir 1950 to the applicator pad 1910. For example, the grip 1940 can be bendable such that a first end of the grip 1940 can be rotated relative to a second end of the grip 1940, causing an inner surface of the grip 1940 to apply pressure to the reservoir 1950 to snap, crush, or otherwise break the reservoir 1950. In some embodiments, the grip 1940 can include a bendable hinge or notched feature near a midpoint of the grip 1940 such that the first portion 1942 can be rotated relative to the second portion 1944 about the hinge or notch to cause the reservoir 1950 to break. In some embodiments, the grip 1940 can include a force concentrating component 1909 such as a tipped projection or a steel ball that can project from an inner surface of the grip 1940 such that bending the grip 1940 pushes the force concentrating component 1909 into breaking contact with a portion of the reservoir 1950, causing the reservoir 1950 to break. In some embodiments, the force concentrating component 1909 can be aligned with a weakened or pre-scored portion of the reservoir such that the reservoir will be preferentially broken by the force concentrating component 1909 at the weakened or pre-scored portion. In some embodiments, a subject or caregiver can use two hands to bend the first portion 1942 relative to the second portion 1944 to break the reservoir 1950. In some embodiments, a subject or caregiver can place the system 1900 on a hard surface (e.g., a table) and apply a downward orthogonal force against the grip 1940 such that the reservoir 1950 is urged into breaking contact with the force concentrating component 1909 and the contents of the reservoir 1950 are released. In some embodiments, a subject or caregiver can place the system 1900 directly against the wound with the applicator pad 1910 against the wound, and can apply a force orthogonal to the wound to the grip 1940 such that the reservoir 1950 is urged into breaking contact with the force concentrating component 1909 and the contents of the reservoir 1950 are released. Thus, in some embodiments, a user can apply pressure to the grip 1940 using a palm of the user's hand, and that pressure can be concentrated to a particular location on the reservoir 1950 by the force concentrating component 1909 to break the reservoir 1950.

After the reservoir 1950 is broken, the contents of the reservoir 1950 can flow from the reservoir 1950 to the applicator pad 1910 through a sidewall of the grip 1940. For example, the grip 1940 can define one or more openings through which fluid can flow to the applicator pad 1910, which may be coupled or releasably coupled to a sidewall of the grip 1940 and aligned with the openings. In some embodiments, the grip 1940 can include a filter (not shown) disposed between the reservoir 1950 and the applicator pad 1910 to prevent unwanted material (e.g., particles above a certain size and/or glass pieces) from reaching the applicator pad 1910. For example, the filter can be disposed within or adjacent to the one or more openings defined by the grip 1940.

In some embodiments, the grip 1940 can be releasably coupled to the applicator pad 1910 using any of the releasable coupling mechanism described herein such that, as shown in FIG. 23C, the grip 1940 can be decoupled from the applicator pad 1910 after wetting the applicator pad 1910. For example, before or after breaking the reservoir 1950 to wet the applicator pad 1910, the applicator pad 1910 can be disposed in contact with a target wound. After applying pressure to the grip 1940 to break the reservoir 1950 and wet the applicator pad 1910, the grip 1940 can be pressed against the applicator pad 1910 to apply pressure to the wound. After a period of time, the grip 1940 can be decoupled from the applicator pad 1910, leaving the applicator pad 1910 disposed in contact with the wound. In some embodiments, the applicator pad 1910 can include an adhesive portion on a skin-contacting surface of the applicator pad 1910 (e.g., adjacent to a perimeter of the skin-contacting surface) to retain the applicator pad 1910 in place relative to the wound. In some embodiments, adhesive tabs can be applied to the applicator pad 1910 and the skin of the subject to retain the applicator pad 1910 in place relative to the wound. In some embodiments, as shown in FIG. 23C, a backing portion 1918, which may be the same or similar as any of the backing portions or bandages described herein, can be placed over the top of the applicator pad 1910 to apply compressive pressure to the applicator pad 1910 and, thus, the wound, and/or to maintain the applicator pad 1910 in place relative to the wound.

Figure 24:
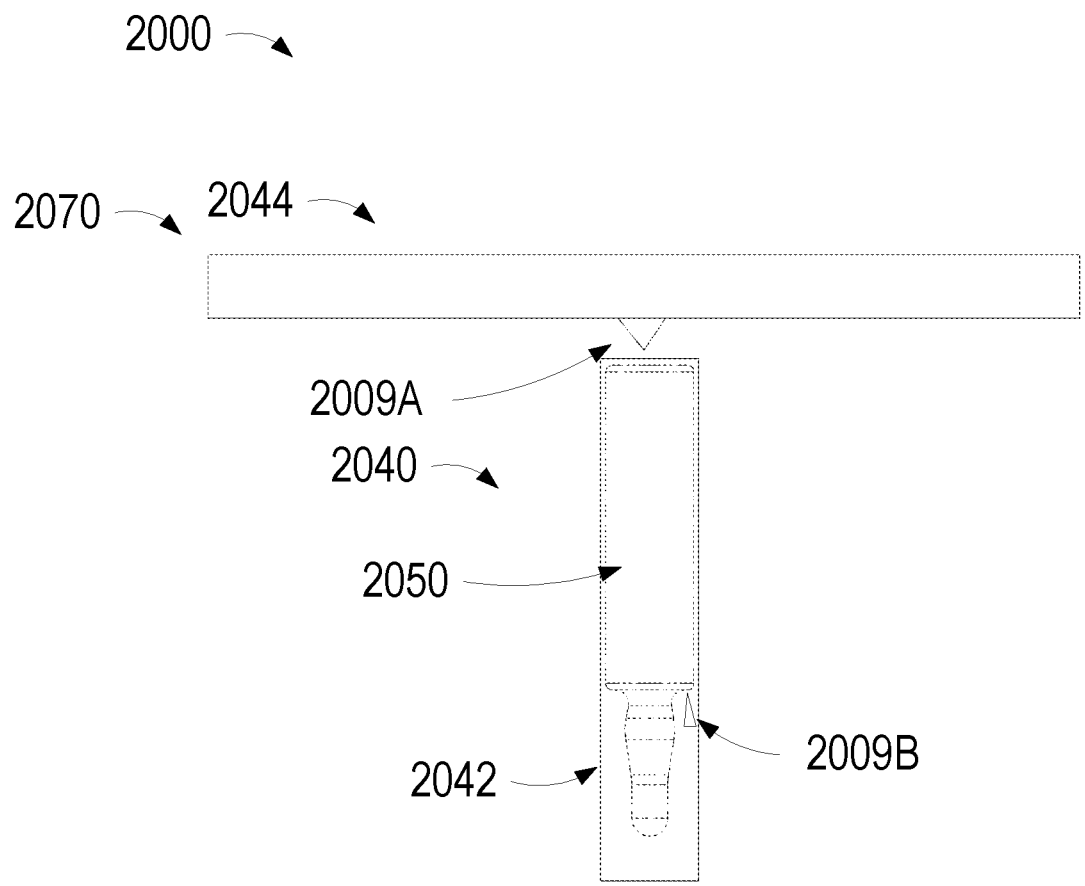
FIG. 24 is a schematic illustration of a bleeding treatment system, according to an embodiment.

In some embodiments, a force concentrating component can be disposed on a first portion or a second portion of a grip and the second portion of the grip can be moved (e.g., rotated and/or translated) relative to a first portion of the grip containing a reservoir to break the reservoir due to contact between the reservoir and the force concentrating component. For example, FIG. 24 is a schematic illustration of a system 2000. The system 2000 can be the same or similar in structure and/or function to any of the systems described herein. For example, the system 2000 includes a reservoir 2050, an applicator device 2070, and an applicator pad (not shown). The applicator device 2070 includes a grip 2040 including a first portion 2042 and a second portion 2044. The first portion 2042 can define an interior space within which the reservoir 2050 can be disposed. The second portion 2044 can be configured to rotate and advance relative to the first portion 2042. For example, the second portion 2044 can be coupled to the first portion 2042 via a threaded connection. A first force concentrating component 2009A can be disposed on a reservoir-facing surface of the second portion 2044 and/or a second force concentrating component 2009B can be disposed on a reservoir-facing surface of the first portion 2042 (e.g., on a sidewall or a ramp or projection extending from the sidewall). In some embodiments, rotation of the second portion 2044 can cause the second portion 2044 to advance toward the reservoir and apply pressure to the reservoir 2050 with the first force concentrating component 2009A until the reservoir 2050 breaks. In some embodiments, rotation of the second portion 2044 can cause the second portion 2044 to advance toward the reservoir and/or advance the reservoir such that the reservoir 2050 is urged against the second force concentrating component 2009B until the reservoir 2050 breaks. In some embodiments, the second force concentrating component 2009B can be disposed such that the second force concentrating component 2009B will contact a shoulder of the reservoir 2050 and break the reservoir 2050 at the shoulder. In some embodiments, an air vent (not shown) can be included to facilitate fluid travel from the reservoir 2050 toward the applicator pad (not shown).

In some embodiments, an applicator pad can be prepared (e.g., wetted) in a tray included in a kit prior to being applied to a target wound of a subject. For example, FIGS. 25A-25C are schematic illustrations of a sequence of steps performed using a kit 2100. The kit 2100 can include any of the systems used according to any of the methods described herein. For example, the kit 2100 can include an applicator pad 2110 and a reservoir 2150 containing fluid. As shown in FIG. 25A, the kit 2100 can include a tray 2101 housing the applicator pad 2110 and the reservoir 2150. The fluid in the reservoir 2150 can include a medication and/or a medication activating agent such as saline. As shown in FIG. 25A, the applicator pad 2110 can optionally include or be coupled to adhesive strips 2103 configured to attach the applicator pad 2110 to skin of a subject. As shown in FIG. 25B, the fluid can be transferred from the reservoir 2150 to the applicator pad 2110 to transfer medication to the applicator pad 2110 and/or to combine with dry medication predisposed in the applicator pad 2110. The reservoir 2150 can be similar to any of the reservoirs described herein. Furthermore, the fluid can be transferred from the reservoir 2150 using any of the applicator devices described herein. As shown in FIG. 25C, a backing portion 2118 (e.g., a bandage) can be coupled to the applicator pad 2110 (e.g., via adhesive). The backing portion 2118 can include a convex distal surface 2136 configured to be coupled to the applicator pad 2110 to apply targeted and increased pressure to the wound via the applicator pad 2110. The applicator pad 2110 can then be disposed in contact with the wound with the backing portion 2118 being coupled to the skin surrounding the wound. In some embodiments, the backing portion 2118 can be removed after a predetermined period of time (e.g., four, five, six, or ten minutes).

In some embodiments, an applicator device such as any of the applicator devices described herein can be included in the kit 2100 can used to release the contents of the reservoir. The applicator device can then be used to apply the applicator pad 2110 to the wound and to apply pressure to the wound, or the applicator pad 2110 can optionally be separated from the applicator device (e.g., in the tray 2101) and the applicator pad 2110 can be applied to the wound and pressed against the wound using fingers and/or a palm of the subject or caregiver. Optionally, the backing portion 2118 can be applied to the applicator pad 2110 before or after applying the applicator pad 2110 to the wound.

Figure 26A:
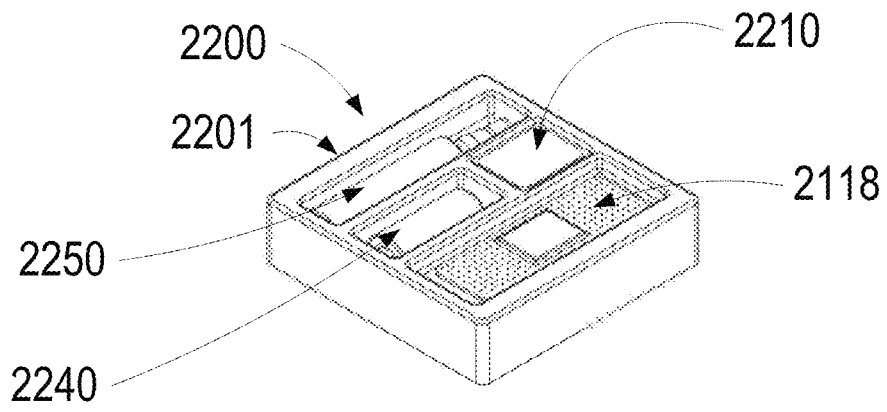
FIGS. 26A-26C are schematic illustrations of a sequence of steps performed using a kit, according to an embodiment.
Figure 26B:
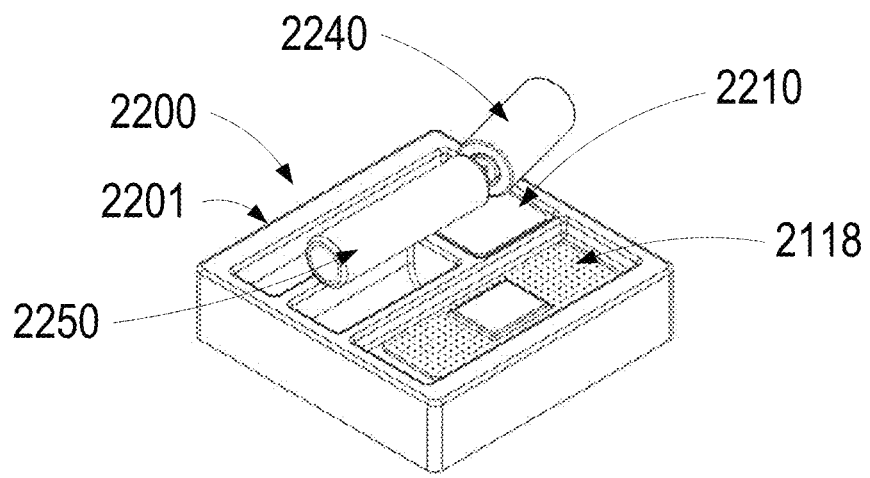
Figure 26C:
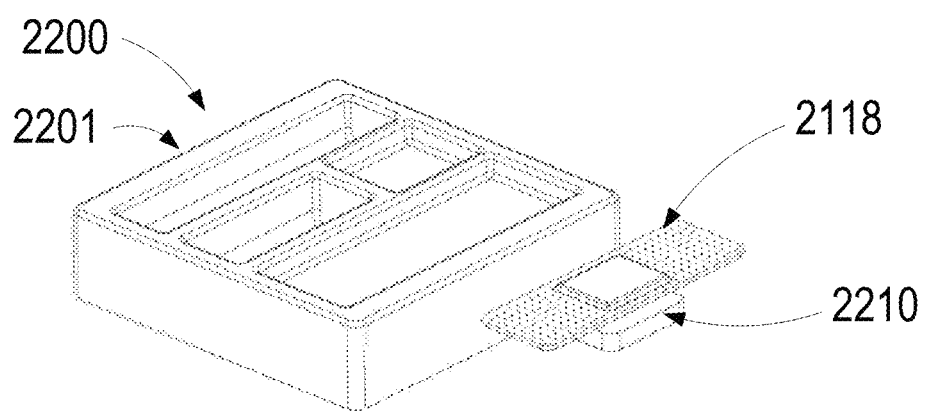

FIGS. 26A-26C are schematic illustrations of a sequence of steps performed using a kit 2200. The kit 2200 can include any of the systems used according to any of the methods described herein. For example, the kit 2200 can include an applicator pad 2210 and a reservoir 2250 containing fluid. As shown in FIG. 26A, the kit 2200 can include a tray 2201 housing the applicator pad 2210 and the reservoir 2250. The fluid in the reservoir 2250 can include a medication and/or a medication activating agent such as saline. As shown in FIG. 26B, the fluid can be transferred from the reservoir 2250 to the applicator pad 2210 to transfer medication to the applicator pad 2210 and/or to combine with dry medication predisposed in the applicator pad 2210. The reservoir 2250 can be similar to any of the reservoirs described herein. Furthermore, the fluid can be transferred from the reservoir 2250 using any of the applicator devices described herein. As shown, for example, the kit 2200 can include a grip 2240 that can be disposed over at least a portion (e.g., a neck portion or a half portion) of the reservoir 2250 as shown in FIG. 26B and rotated away from a central axis of the reservoir 2250 such that a portion of the reservoir 2250 disposed within the grip 2240 is broken (e.g., separated from a remainder of the reservoir 2250 outside of the grip 2240) and fluid is released.

As shown in FIG. 26C, a backing portion 2118 (e.g., a bandage) can be coupled to the applicator pad 2210 (e.g., via adhesive). The backing portion 2218 can include a convex distal surface configured to be coupled to the applicator pad 2210 to apply targeted and increased pressure to the wound via the applicator pad 2210. The applicator pad 2210 can then be disposed in contact with the wound with the backing portion 2218 being coupled to the skin surrounding the wound. In some embodiments, the backing portion 2218 can be removed after a predetermined period of time (e.g., four, five, six, or ten minutes).

In some embodiments, an applicator device such as any of the applicator devices described herein can be included in the kit 2200 can used to release the contents of the reservoir. The applicator device can then be used to apply the applicator pad 2210 to the wound and to apply pressure to the wound, or the applicator pad 2210 can optionally be separated from the applicator device (e.g., in the tray 2201) and the applicator pad 2210 can be applied to the wound and pressed against the wound using fingers and/or a palm of the subject or caregiver. Optionally, the backing portion 2218 can be applied to the applicator pad 2210 before or after applying the applicator pad 2210 to the wound.

While various embodiments have been described herein, textually and/or graphically, it should be understood that they have been presented by way of example only, and not limitation. Likewise, it should be understood that the specific terminology used herein is for the purpose of describing particular embodiments and/or features or components thereof and is not intended to be limiting. Various modifications, changes, enhancements, and/or variations in form and/or detail may be made without departing from the scope of the disclosure and/or without altering the function and/or advantages thereof unless expressly stated otherwise. Functionally equivalent embodiments, implementations, and/or methods, in addition to those enumerated herein, will be apparent to those skilled in the art from the foregoing descriptions and are intended to fall within the scope of the disclosure.

Where schematics, embodiments, and/or implementations described above indicate certain components arranged and/or configured in certain orientations or positions, the arrangement of components may be modified, adjusted, optimized, etc. The specific size and/or specific shape of the various components can be different from the embodiments shown and/or can be otherwise modified, while still providing the functions as described herein. More specifically, the size and shape of the various components can be specifically selected for a desired or intended usage. Thus, it should be understood that the size, shape, and/or arrangement of the embodiments and/or components thereof can be adapted for a given use unless the context explicitly states otherwise. By way of example, in some implementations, a treatment device intended to provide treatment to an adult user may have a first size and/or shape, while a treatment device intended to provide treatment to a pediatric user may have a second size and/or shape smaller than the first size and/or shape. Moreover, the smaller size and/or shape of, for example, a pediatric treatment device may result in certain components being moved, reoriented, and/or rearranged while maintaining the desired function of the device.

Although various embodiments have been described as having particular characteristics, functions, components, elements, and/or features, other embodiments are possible having any combination and/or sub-combination of the characteristics, functions, components, elements, and/or features from any of the embodiments described herein, except mutually exclusive combinations or when clearly stated otherwise. Moreover, unless otherwise clearly indicated herein, any particular combination of components, functions, features, elements, etc. can be separated and/or segregated into independent components, functions, features, elements, etc. or can integrated into a single or unitary component, function, feature, element, etc.

Where methods described above indicate certain events occurring in certain order, the ordering of certain events may be modified. Additionally, certain of the events may be performed concurrently in a parallel process when possible, as well as performed sequentially as described above. While methods have been described as having particular steps and/or combinations of steps, other methods are possible having a combination of any steps from any of methods described herein, except mutually exclusive combinations and/or unless the context clearly states otherwise.

The invention claimed is:

1. A system, comprising:
an applicator pad;
a grip releasably couplable to the applicator pad and configured to dispose the applicator pad against a wound of a subject such that pressure can be transferred to the wound via the applicator pad to enhance hemostasis, the grip including a convex distal surface configured to contact a proximal surface of the applicator pad and urge at least a portion of the applicator pad toward the wound;
a reservoir configured to contain medication to be released to the wound via the applicator pad; and
a release mechanism coupled to the reservoir and configured to transition from a closed condition to an open condition to allow medication to flow from the reservoir and to the applicator pad via a fluid coupling in response to a pressure above a threshold pressure within the reservoir.

2. The system of claim 1, wherein the reservoir is a first reservoir included in the applicator pad, further comprising a second reservoir and a fluid coupling configured such that liquid can flow from the second reservoir to the applicator pad via the fluid coupling.

3. The system of claim 1, wherein the applicator pad includes a pad retainer configured to maintain the applicator pad in contact with the wound after the grip is decoupled from the applicator pad.

4. The system of claim 1, wherein the grip includes a first portion and a second portion, the second portion configured to be moved relative to the first portion to cause liquid to be released from the reservoir to the applicator pad.

5. The system of claim 1, wherein the reservoir contains the medication.

6. The system of claim 5, wherein the medication includes at least one of an antifibrinolytic, a vasoconstrictor, an antibiotic, an anti-infectant, or a steroid.

7. The system of claim 5, wherein the medication is tranexamic acid (TXA).

8. The system of claim 7, wherein the applicator pad includes a material that is non-reactive with TXA.

9. The system of claim 7, wherein the applicator pad includes a foamed polymer.

10. The system of claim 7, wherein the applicator pad includes a natural fiber.

11. The system of claim 1, wherein the medication includes an antifibrinolytic.

12. The system of claim 1, wherein the grip includes a plate disposed on a distal end of the grip and configured to apply a distributed, uniform force to the applicator pad when pressed toward the wound with a force orthogonal to the skin.

13. The system of claim 1, wherein the grip includes a force concentrating component projecting from an interior surface of the grip and configured to be urged toward the reservoir to break a sidewall of the reservoir and release the medication to the applicator pad.

14. The system of claim 1, wherein the applicator pad contains the reservoir and is pre-soaked with the medication to a saturation within a range of about 25% to about 50% of the saturation point of the applicator pad.

15. The system of claim 1, wherein a sidewall portion of the grip is configured to be urged toward the reservoir to transition the reservoir from a closed condition to an open condition.

16. The system of claim 1, wherein the applicator pad is configured to expand in response to absorbing blood from the wound.

17. The system of claim 1, wherein the applicator pad includes a backing having a convex distal surface such that the applicator pad has a convex distal surface, the backing being more rigid than a distal portion of the applicator pad coupled to the backing.

18. The system of claim 1, further comprising a bandage couplable to a proximal surface of the applicator pad, the bandage having a convex distal surface configured to contact a proximal surface of the applicator pad and urge at least a portion of the applicator pad toward the wound.

19. A system, comprising:
an applicator pad;
a backing having a convex distal surface coupled to the applicator pad such that the applicator pad has a convex distal surface, the backing being more rigid than the applicator pad;
a grip releasably couplable to the applicator pad and configured to dispose the applicator pad against a wound of a subject such that pressure can be transferred to the wound via the applicator pad to enhance hemostasis; and
a reservoir configured to contain medication to be released to the wound via the applicator pad.

20. A system, comprising:
an applicator pad;
a grip releasably couplable to the applicator pad and configured to dispose the applicator pad against a wound of a subject such that pressure can be transferred to the wound via the applicator pad to enhance hemostasis, the grip including:
a first portion including an elongated body and a plate disposed on a distal end of the elongated body, the elongated body having a central axis that is perpendicular to a distal surface of the applicator pad, the plate configured to distribute uniformly to the applicator pad force applied to the grip and to compress the applicator pad against the wound when the elongated body is pressed toward the wound with a force directed orthogonally to a distal surface of the applicator pad and coaxial with the elongated body, the plate having a central axis that is coaxial with a central axis of the applicator pad, the plate having an outer perimeter larger than an outer perimeter of the applicator pad,
a second portion coupled to the first portion, the first portion and the second portion collectively defining an interior space, and
a set of release mechanisms; and
a set of reservoirs disposed within the interior space and configured to contain a medication, the second portion configured to be translated relative to the first portion along the central axis of the elongated body to urge each release mechanism of the set of release mechanisms into engagement with a respective reservoir of the set of reservoirs such that a portion of each reservoir of the set of reservoirs is ruptured by the respective release mechanism to allow the medication to flow from the set of reservoirs and to the applicator pad to partially saturate the applicator pad, the medication having a volume and the applicator pad having an absorbent capacity such that the applicator pad can absorb blood from the wound and receive the medication from the reservoir.

21. The system of claim 20, further comprising a backing coupled to a proximal surface of the applicator pad, the backing defining a set of openings, the system configured such that the medication can flow from the set of reservoirs, through the set of openings in the backing, and to the applicator pad.

22. The system of claim 21, further comprising a release mechanism including a release button disposed on the grip, the release mechanism configured to release the applicator pad and the backing from the grip in response to depression of the release button.

23. The system of claim 20, wherein each reservoir of the set of reservoirs includes a barrel and a plunger.

24. The system of claim 20, further comprising a spring configured to transition from an initial configuration to an activated configuration in response to the second portion of the grip being translated relative to the first portion of the grip, the spring configured to apply pressure to the set of reservoirs in the activated configuration such that the medication flows from the set of reservoirs.

25. The system of claim 20, wherein, when the medication is allowed to flow from the set of reservoirs to the applicator pad to partially saturate the applicator pad, the applicator pad is saturated to a saturation within a range of about 25% to about 50% of the absorbent capacity of the applicator pad.

26. The system of claim 20, further comprising the medication, the medication including tranexamic acid (TXA).

27. A system, comprising:
an applicator pad;
a grip releasably couplable to the applicator pad and configured to dispose the applicator pad against a wound of a subject such that pressure can be transferred to the wound via the applicator pad to enhance hemostasis, the grip including a convex distal surface configured to contact a proximal surface of the applicator pad and urge at least a portion of the applicator pad toward the wound;

a first reservoir included in the applicator pad and configured to contain medication to be released to the wound via the applicator pad;

a second reservoir; and a fluid coupling configured such that liquid can flow from the second reservoir to the applicator pad via the fluid coupling.

28. A system, comprising:

an applicator pad;

a grip releasably couplable to the applicator pad and configured to dispose the applicator pad against a wound of a subject such that pressure can be transferred to the wound via the applicator pad to enhance hemostasis, the grip including a convex distal surface configured to contact a proximal surface of the applicator pad and urge at least a portion of the applicator pad toward the wound; and a reservoir configured to contain medication to be released to the wound via the applicator pad, a sidewall portion of the grip configured to be urged toward the reservoir to transition the reservoir from a closed condition to an open condition.

* * * * *